(12) United States Patent
Roe

(10) Patent No.: US 7,592,370 B2
(45) Date of Patent: *Sep. 22, 2009

(54) FATTY ACID TREATMENT FOR CARDIAC PATIENTS

(75) Inventor: Charles R. Roe, Rockwall, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/748,495

(22) Filed: Dec. 30, 2003

(65) Prior Publication Data

US 2004/0152776 A1 Aug. 5, 2004

Related U.S. Application Data

(62) Division of application No. 10/371,685, filed on Feb. 21, 2003, now abandoned, which is a division of application No. 09/890,559, filed as application No. PCT/US00/03022 on Feb. 3, 2000, now Pat. No. 6,740,679.

(60) Provisional application No. 60/119,038, filed on Feb. 5, 1999.

(51) Int. Cl.
*A61K 31/17* (2006.01)
*A61K 31/20* (2006.01)

(52) U.S. Cl. ........................... 514/547; 514/558

(58) Field of Classification Search .............. 514/547, 514/558
See application file for complete search history.

(56) References Cited

U.S. PATENT DOCUMENTS

| 3,697,563 | A | * | 10/1972 | Garzia | 554/111 |
| 4,753,963 | A | | 6/1988 | Jandacek et al. | |
| 5,153,221 | A | | 10/1992 | Revici | 514/557 |
| 5,968,982 | A | | 10/1999 | Voss et al. | 514/558 |
| 6,225,347 | B1 | * | 5/2001 | Buchmann et al. | 514/530 |

FOREIGN PATENT DOCUMENTS

| EP | 0530861 | 3/1993 |
| EP | 0861657 | 9/1998 |
| JP | 52015834 | 2/1977 |
| JP | 52015834 | 5/1977 |
| WO | WO 9615784 | 5/1996 |

OTHER PUBLICATIONS

Roe et al., "Treatment of cardiomyopathy and rhabdomyolysis in long-chain fat oxidation disordes using an anaplerotic odd-cain triglyceride", The Journal of Clinical Investigation vol. 110(2) pp. 259-269 (2002).*
Salzer et al., Pediatric Card 10:17-23, (1989).*
Rice et al., Neurology vol. 9 part 2, 1-15, (2005).*
Iwama et al., Internal Medicine, vol. 36(9) 1997, 613-617.*
Jones et al. British Med. J. 1961, 1276-1278.*
Niezen-Koning J. Inher. Metab. Dis 18, 1995, 230-232.*
Bach et al. (Am. J. Clin. Nutri. 1982;950-962).*
Anderson, et al. 1975. "Glucogenic and ketogenic capacities of lard, safflower oil, and triundecanoin in fasting rats," *J Nutr* 105:185-189.
Bohles, et al. 1987. "The influence of intravenous medium-and long-chain triglycerides and carnitine on the excretion of dicarboxylic acids," *J Par Ent Nut* 11:46-48.
Boyer, et al. 1970. "Hepatic metabolism of 1-$^{14}$C octanoic and 1-$^{14}$C margaric acids," *Lipids* 4:615-617.
van Itallie, TB and Khachadurian, AK. 1969. "Rats enriched with odd-carbon fatty acids: maintenance of liver glycogen during starvation, " *Science* 165:811-813.
van Kempen, T and Odle, J. 1993. "Medium-chain fatty acid oxidation in colostrum-deprived newborn piglets: stimulative effect of L-carnitine supplementation," *J Nutr* 123:1531-1537.
Lin, et al. 1996. "Acetate represents a major product of heptanoate and octanoate beta-oxidation in hepatocytes isolated from neonatal piglets," *Biochem J* 318:235-240.
Linseisen, J and Wolfram, G. 1993. "Odd-numbered medium-chain triglycerides (trinonanoin) in total parenteral nutrition: effects on parameters of fat metabolism in rabbits," *J Par and Ent Nutr* 17:522-528.
Odle, et al. 1989. "Utilization of medium-chain triglycerides by neonatal piglets: II Effects of even- and odd-chain triglyceride consumption over the first 2 days of life on blood metabolites and urinary nitrogen excretion," *J Animal Sci* 67:3340-3351.
Odle, et al. 1991. "Utilization of medium-chain triglycerides by neonatal piglets: chain length of even- and odd-carbon fatty acids and apparent digestion/absorption and hepatic metabolism," *J Nutr* 121:605-614.
Odle, et al. 1992. "Evaluation of [1-$^{14}$C]-medium-chain fatty acid oxidation by neonatal piglets using continuous-infusion radiotracer kinetic methodology," *J Nutr* 122:2183-2189.
Odle, et al. 1994. "Emulsification and fatty acid chain length affect the kinetics of [$^{14}$C]-medium-chain length triacylglycerol utilization by neonatal piglets," *J Nutri* 124:84-93.

(Continued)

Primary Examiner—Michael G Hartley
Assistant Examiner—Shirley V Gembeh
(74) Attorney, Agent, or Firm—Chainey P. Singleton; Edwin S. Flores; Chalker Flores, LLP

(57) ABSTRACT

A method of treating patients in need of treatment for a cardiac disorder has been found which comprises administering to the patient a seven carbon fatty acid compound or derivative thereof, wherein the compound or derivative thereof is able to readily enter the mitochondrion without special transport enzymes. A dietary formulation suitable for treatment of heart tissue in cardiac or surgical patients has been found which comprises a seven-carbon fatty acid chain, wherein the seven-carbon fatty acid chain is characterized by the ability to transverse the inner mitochondrial membrane by a transport mechanism which does not require carnitine palmitoyltransferase I, carnitine palmitoyltransferase II, or carnitine/acylcarnitine translocase and the ability to undergo mitochondrial β-oxidation, and wherein the compound is selected from the group consisting of n-heptanoic acid or a derivative thereof, a triglyceride comprising n-heptanoic acid or a derivative thereof, and triheptanoin or a derivative thereof.

22 Claims, 54 Drawing Sheets

OTHER PUBLICATIONS

Odle, J. 1997. "New insights into the utilization of medium-chain triglycerides by the neonate: observations from a piglet model," *J Nutr* 127: 1061-1067.

Pi-Sunyer, FX. 1971. "Rats enriched with odd-carbon fatty acids: effect of prolonged starvation on liver glycogen and serum lipids, glucose and insulin," *Diabetes* 20:200-205.

Roe, et al. 2002. "Treatment of caridopathy and rhabdomyolysis in long-chain fat oxidation disorders usng an anaplerotic odd-chain triglyceride," *J Clin Invest* 110:259-269.

Sugden, et al. 1984. "Odd-carbon fatty acid metabolism in hepatocytes from starved rats," *Biochem Int'l* 8:61-67.

Yang, et al. 1998. "Identification of four novel mutations in patients with carnitine palmitoyltransferase II (CPT II) deficiency," *Mol Gen Metab* 64:229-236.

Kerner, J., et al., "Genetic Disorders of Carnitine Metabolism and Their Nutritional Management," Annu Rev Nutr (1998), 18:179-206.

Miller, E. R., et al., "The Pig as a Model for Human Nutrition," Ann Rev Nutr (1987), 7:361-382.

\* cited by examiner

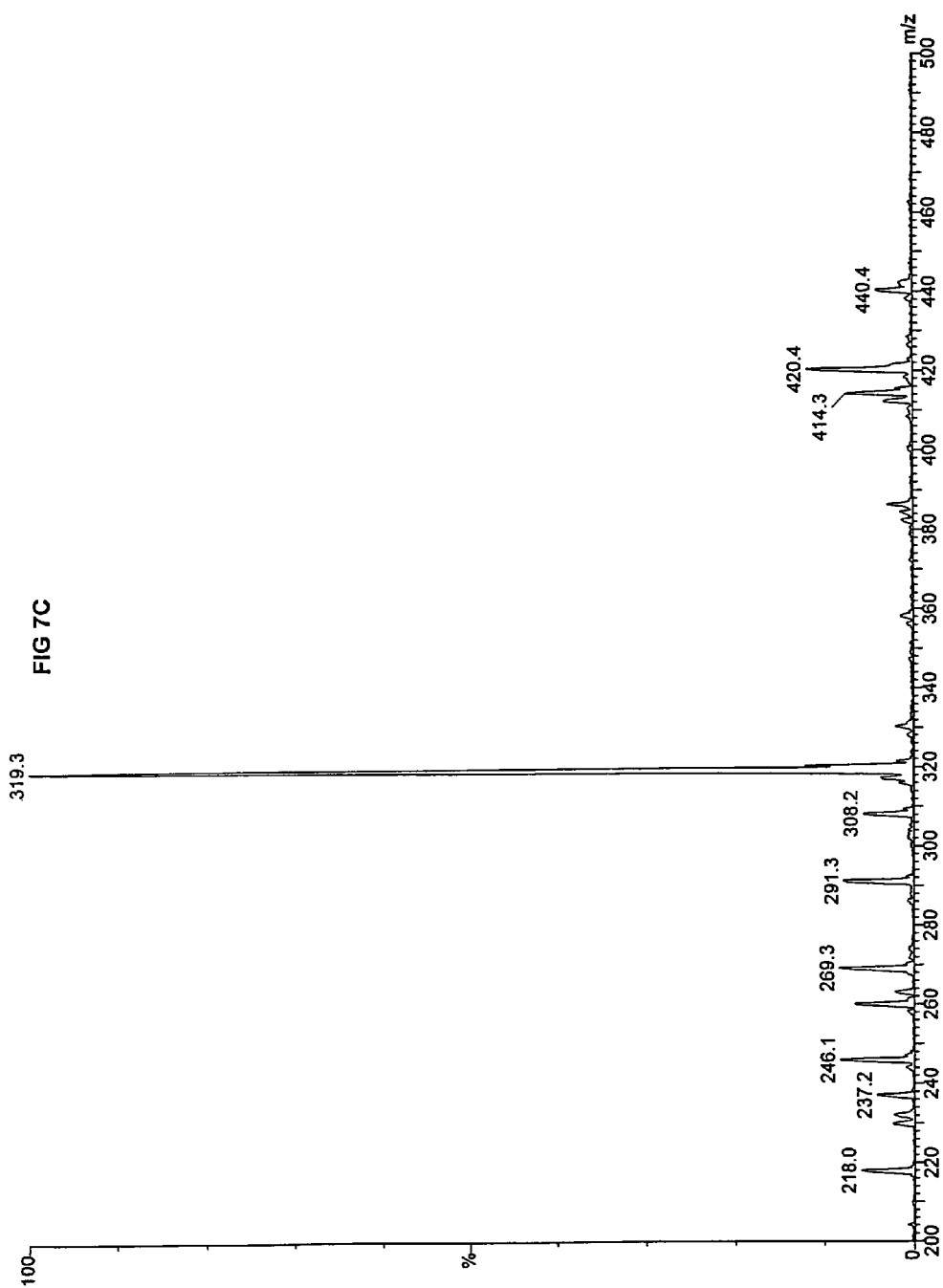

FATTY ACID TREATMENT FOR CARDIAC PATIENTS

CROSS REFERENCES TO RELATED APPLICATIONS

This application is a divisional of U.S. application Ser. No. 10/371,685 filed on 21 Feb. 2003 now abandoned which is a divisional of U.S. application Ser. No. 09/890,559 filed on 1 Aug. 2001 now U.S. Pat. No. 6,740,679 which was the National Stage of International Application No. PCT/US00/03022 filed on 3 Feb. 2000 which claims the benefit of U.S. Provisional Application No. 60/119,038 which was filed on 5 Feb. 1999

TECHNICAL FIELD OF THE INVENTION

The invention relates to a nutritional or dietetic composition or supplement.

BACKGROUND OF THE INVENTION

Fatty acid oxidation plays a major role in the production of energy, and is essential during periods of fasting. Serious disorders in fatty acid metabolism can arise which range from skeletal and/or cardiac muscle weakness to episodes of metabolic apnea to death resembling sudden infant death syndrome. These disorders manifest with severe cardiomyopathy, hypoglycemia, myopathy, microvesicular fat deposition in affected organs, and/or fulminant hepatic failure. Patients suffering from inborn genetic errors in fatty acid metabolism often experience fatal or repeated severely debilitating episodes upon failure to generate energy via fatty acid metabolism. Premature infants require a maintenance of a high blood sugar level. Often, their routine diet does not provide sufficient amounts of carbohydrate energy sources and their fat metabolism enzymes are not efficient at birth. Elderly patients also experience difficulty in the regulation of blood sugar levels due to decreased appetite and inefficient metabolism.

Saturated fatty acids are represented by the following structure

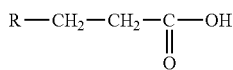

where R represents an alkyl group. Naturally occurring fatty acids derived from higher plant and animal lipids include both saturated and unsaturated even-numbered carbon chains. The most abundant naturally occurring saturated fatty acids are palmitic acid (16 carbons; $C_{16}$) and stearic acid (18 carbons; $C_{18}$). Shorter-chain fatty acids (12-14 carbons; $C_{12}$ to $C_{14}$) and longer-chain fatty acids (up to 28 carbons; $C_{28}$) naturally occur in small quantities. Fatty acids of less than 10 carbons are rarely present in animal lipids, with the exception of milk fat comprising about 32% oleic acid (unsaturated $C_{18}$), about 15% palmitic acid ($C_{16}$), about 20% myristic acid ($C_{14}$), about 15% stearic acid ($C_{18}$), about 6% lauric acid ($C_{12}$), and about 10% fatty acids of 4-10 carbons ($C_4$-$C_{10}$).

Fatty acids are generally categorized by the length of the carbon chain attached to the carboxyl group: short-chain for 4 to 6 carbons ($C_4$-$C_6$), medium-chain for 8 to 14 carbons ($C_8$-$C_{14}$), long-chain for 16 to 18 carbons ($C_{16}$-$C_{18}$), and very long-chains for 20 to 28 carbons ($C_{20}$-$C_{28}$).

The process by which fatty acids are metabolized involves mitochondrial β-oxidation in the mitochondria of the cell. As illustrated in FIG. 1, fatty acid oxidation of a long-chain fatty acid such as palmitic acid begins transport of the fatty acid through the plasma membrane via a plasma membrane carnitine transporter. As the fatty acid passes through the outer mitochondrial membrane, the fatty acid is converted in the presence of Coenzyme A (CoASH) and acyl-CoA synthetase into a fatty acid ester of Coenzyme A (fatty acyl-CoA) at the expense of ATP. The fatty acyl-CoA is converted into fatty acylcarnitine in the presence of carnitine and carnitine palmitoyltransferase I (CPT I). The fatty acylcarnitine then passes the inner membrane of the mitochondria, a step which is catalyzed by the carnitine/acylcarnitine translocase enzyme. Once inside the mitochondria, the fatty acylcarnitine is then converted back into fatty acyl-CoA in the presence of carnitine palmitoyltransferase II (CPT II). In the oxidation cycle within the mitochondria, the fatty acyl-CoA is dehydrogenated by removal of a pair of hydrogen atoms from the α and β carbon atoms via a chain-specific acyl-CoA dehydrogenase to yield the α, β-unsaturated acyl-CoA, or 2-trans-enoyl-CoA. The appropriate acyl-CoA dehydrogenase is determined by the carbon chain length of the fatty acyl-CoA, i.e., long-chain acyl-CoA dehydrogenase (LCAD; $C_{12}$ to $C_{18}$), medium-chain acyl-CoA dehydrogenase (MCAD; $C_4$ to $C_{12}$), short-chain acyl-CoA dehydrogenase (SCAD; $C_4$ to $C_6$), or very long-chain acyl-CoA dehydrogenase (VLCAD; $C_{14}$ to $C_{20}$). The α, β-unsaturated acyl-CoA is then enzymatically hydrated via 2-enoyl-CoA hydratase to form L-3-hydroxyacyl-CoA, which in turn is dehydrogenated in an NAD-linked reaction catalyzed by a chain-specific L-3-hydroxyacyl-CoA dehydrogenase to form β-ketoacyl-CoA. The appropriate L-3-hydroxyacyl-CoA dehydrogenase is determined by the carbon chain length of the L-3-hydroxyacyl-CoA, i.e., long-chain L-3-hydroxyacyl-CoA dehydrogenase (LCHAD; $C_{12}$ to $C_{18}$) or short-chain L-3-hydroxyacyl-CoA dehydrogenase (SCHAD; $C_4$ to $C_{16}$ with decreasing activity with increasing chain length). The β-ketoacyl CoA ester undergoes enzymatic cleavage by attack of the thiol group of a second molecule of CoA in the presence of 3-ketoacyl-CoA thiolase, to form fatty acyl-CoA and acetyl-CoA derived from the α carboxyl and the β carbon atoms of the original fatty acid chain. The other product, a long-chain saturated fatty acyl-CoA having two fewer carbon atoms than the starting fatty acid, now becomes the substrate for another round of reactions, beginning with the first dehydrogenation step, until a second two-carbon fragment is removed as acetyl-CoA. At each passage through this spiral process, the fatty acid chain loses a two-carbon fragment as acetyl-CoA and two pairs of hydrogen atoms to specific acceptors.

Each step of the fatty acid oxidation process is catalyzed by enzymes with overlapping carbon chain-length specificities. Inherited disorders of fatty acid oxidation have been identified in association with the loss of catalytic action by these enzymes. These include defects of plasma membrane carnitine transport; CPT I and II; carnitine/acylcarnitine translocase; very-long-chain, medium-chain, and short-chain acyl-CoA dehydrogenases (i.e., VLCAD, MCAD, and SCAD, respectively); 2,4-dienoyl-CoA reductase; long-chain 3-hydroxyacyl-CoA dehydrogenase acyl-CoA (LCHAD), and mitochondrial trifunctional protein (MTP) deficiency. To date, treatment for medium chain dehydrogenase (MCAD) deficiency has been found. However, the remaining defects often are fatal to patients within the first year of life, and no known effective treatment has been made available. In particular, patients suffering from severe carnitine/acylcarnitine translocase deficiency routinely die, there are no known survivors, and no known treatment has been found.

Attempts to treat these disorders have centered around providing food sources which circumvent the loss of catalytic action by the defective enzyme. For example, the long-chain fatty acid metabolic deficiency caused by a defective carnitine/acylcarnitine translocase enzyme (referred hereinafter as "translocase deficiency") often leads to death in the neonatal period. Providing carnitine, a high carbohydrate diet, and medium-chain triglycerides to one translocase-deficient patient failed to overcome the fatty acid metabolic deficiency. It was believed that the metabolism of medium-chain fatty acids would not require the carnitine/acylcarnitine translocase enzyme, since medium-chain fatty acids are expected to freely enter the mitochondria. Thus, infant formulas were developed comprising even-carbon number medium-chain triglycerides (MCT) (e.g., 84% $C_8$, 8% $C_6$ and 8% $C_{10}$) which were expected to by-pass the translocase defect. Fatalities continue to occur despite treatment attempts with these formulas.

With the exception of pelargonic acid (saturated fatty acid with 9 carbons; $C_9$), odd-carbon number fatty acids are rare in higher plant and animal lipids. Certain synthetic odd-carbon number triglycerides have been tested for use in food products as potential fatty acid sources and in the manufacture of food products. The oxidation rates of odd-chain fatty acids from $C_7$ and $C_9$ triglycerides have been examined in vitro in isolated piglet hepatocytes. (Odle, et al. 1991. "Utilization of medium-chain triglycerides by neonatal piglets: chain length of even- and odd-carbon fatty acids and apparent digestion/absorption and hepatic metabolism," *J Nutr* 121:605-614; Lin, X, et al. 1996. "Acetate represents a major product of heptanoate and octanoate beta-oxidation in hepatocytes isolated from neonatal piglets," *Biochem J* 318:235-240; and Odle, J. 1997. "New insights into the utilization of medium-chain triglycerides by the neonate: observations from a piglet model," *J Nutr* 127:1061-1067). The importance of odd-chain fatty acids propionate ($C_3$), valerate ($C_5$), and nonanoate ($C_9$) as gluconeogenic precursors was evaluated in hepatocytes from starved rats. (Sugden, et al. 1984. "Odd-carbon fatty acid metabolism in hepatocytes from starved rats," *Biochem Int'l* 8:61-67). The oxidation of radiolabeled margarate ($C_{17}$) was examined in rat liver slices. (Boyer, et al. 1970. "Hepatic metabolism of 1-$^{14}$C octanoic and 1-$^{14}$C margaric acids," Lipids 4:615-617).

In vivo studies utilizing $C_3$, $C_5$, $C_7$, $C_9$, $C_{11}$, and $C_{17}$ have also been carried out in vivo in guinea pigs, rabbits, and rats. In vivo oxidation rates of systematically infused medium-chain fatty acids from $C_7$ and $C_9$ triglycerides, and a $C_7/C_9$ triglyceride mixture have been examined in neonatal pigs. (Odle, et al. 1992. "Evaluation of [1-14C]-medium-chain fatty acid oxidation by neonatal piglets using continuous-infusion radiotracer kinetic methodology," *J Nutr* 122:2183-2189; and Odle, et al. 1989. "Utilization of medium-chain triglycerides by neonatal piglets: II. Effects of even-and odd-chain triglyceride consumption over the first 2 days of life on blood metabolites and urinary nitrogen excretion," *J Anima Sci* 67:3340-3351). Rats fed triundecanoin (saturated $C_{11}$) were observed to maintain nonfasting blood glucose levels during prolonged fasting. (Anderson, et al. 1975. "Glucogenic and ketogenic capacities of lard, safflower oil, and triundecanoin in fasting rats," *J Nutr* 105:185-189.) An emulsion of trinonanoin ($C_9$) and long-chain triglycerides was infused into rabbits for evaluation as long-term total parenteral nutrition. (Linseisen, et al. 1993. "Odd-numbered medium-chain triglycerides (trinonanoin) in total parenteral nutrition: effects on parameters of fat metabolism in rabbits," *J Parenteral and Enteral Nutr* 17:522-528). The triglyceride triheptanoin containing the saturated 7-carbon fatty n-heptanoic acid ($C_7$) has also been reportedly used in Europe in agricultural feed, as a tracer molecule in the manufacture of butter, and as a releasing agent in the manufacture of chocolates and other confectioneries. However, there has been no indication heretofore that a seven-carbon fatty acid is safe for consumption by humans or has any particular nutritional benefit to humans.

It has now been found that acquired metabolic derangements and inherited metabolic disorders, especially fatty acid metabolic defects, can be overcome using a nutritional composition comprising a seven-carbon fatty acid ($C_7$) such as n-heptanoic acid. Patients experiencing defective or reduced fatty acid metabolism can be treated with a nutritional composition comprising a seven-carbon fatty acid such as n-heptanoic acid and/or its triglyceride triheptanoin as a very efficient energy source. Patients needing rapid energy may also benefit from consumption of the seven-carbon fatty acid or its triglyceride.

SUMMARY OF THE INVENTION

In one aspect, the present invention is a method of treating patients in need of treatment for a cardiac disorder, comprising administering to the patient a seven carbon fatty acid compound or derivative thereof, wherein the compound or derivative thereof is able to readily enter the mitochondrion without special transport enzymes. In a preferred method, the seven carbon fatty acid compound comprises n-heptanoic acid. In another preferred method, the seven carbon fatty acid compound comprises a triglyceride comprising n-heptanoic acid, for example, triheptanoin. In a preferred method, the derivative is a five carbon fatty acid chain. In another preferred method, the derivative is selected from the group consisting of 4-methylhexanoate, 4-methylhexenoate, 3-hydroxy-4-methylhexanoate, 5-methylhexanoate, 5-methylhexenoate and 3-hydroxy-5-methylhexanoate. In a preferred method, the compound or derivative thereof is capable of being broken down by normal β-oxidation in humans to methylbutyric acid. In another preferred method, the compound or derivative thereof is capable of being broken down by normal β-oxidation in humans to isovaleric acid. In another preferred method, the compound or derivative is capable of being broken down by normal β-oxidation in humans to n-valeryl-CoA. In yet another preferred method, the compound or derivative is capable of being broken down by normal β-oxidation in humans to propionyl-CoA in one or more oxidative procedures. Preferably, the compound or derivative thereof is provided to the patient in an amount comprising at least about 25% of the dietary caloric requirement for the patient. Preferably, the compound or derivative is provided parenterally or orally. This method is suitable for treating cardiac disorders such as cardiac myopathy. It is also suitable for treatment of the aftermath of heart surgery, wherein the compound or derivative is utilized for direct fueling of heart muscle.

In another aspect, the present invention is a dietary formulation suitable for treatment of heart tissue in cardiac or surgical patients comprising a seven-carbon fatty acid chain, wherein the seven-carbon fatty acid chain is characterized by the ability to transverse the inner mitochondrial membrane by a transport mechanism which does not require carnitine palmitoyltransferase I, carnitine palmitoyltransferase II, or carnitine/acylcarnitine translocase and the ability to undergo mitochondrial β-oxidation, and wherein the compound is selected from the group consisting of n-heptanoic acid or a derivative thereof, a triglyceride comprising n-heptanoic acid or a derivative thereof, and triheptanoin or a derivative thereof.

In another aspect, the present invention is a dietary formulation suitable for treatment of heart tissue in cardiac or surgical patients comprising a seven carbon fatty acid compound or derivative thereof, wherein the compound or derivative thereof is able to readily enter the mitochondrion without special transport enzymes. In a preferred dietary formulation, the seven carbon fatty acid compound comprises n-heptanoic acid. In another preferred dietary formulation, the seven carbon fatty acid compound comprises a triglyceride comprising n-heptanoic acid, for example, triheptanoin. In a preferred dietary formulation, the derivative is a five carbon fatty acid chain. In another preferred dietary formulation, the derivative is selected from the group consisting of 4-methylhexanoate, 4-methylhexenoate, 3-hydroxy-4-methylhexanoate, 5-methylhexanoate, 5-methylhexenoate and 3-hydroxy-5-methylhexanoate. In a preferred dietary formulation, the compound or derivative thereof is capable of being broken down by normal β-oxidation in humans to methylbutyric acid. In another preferred dietary formulation, the compound or derivative thereof is capable of being broken down by normal β-oxidation in humans to isovaleric acid. In another preferred dietary formulation, the compound or derivative is capable of being broken down by normal β-oxidation in humans to n-valeryl-CoA. In yet another preferred dietary formulation, the compound or derivative is capable of being broken down by normal β-oxidation in humans to propionyl-CoA in one or more oxidative procedures.

($^2H_9$-isovaleric-C5), and m/z237.2 ($^2H_5$-propionate-C3). The peak at m/z291 represents D3-C7 (7-$^2H_3$-heptanoate). The peak at m/z235.1 represents D3-C3 (3-$^2H_3$-propionate), the end point of odd-carbon degradation.

Figure 5A:
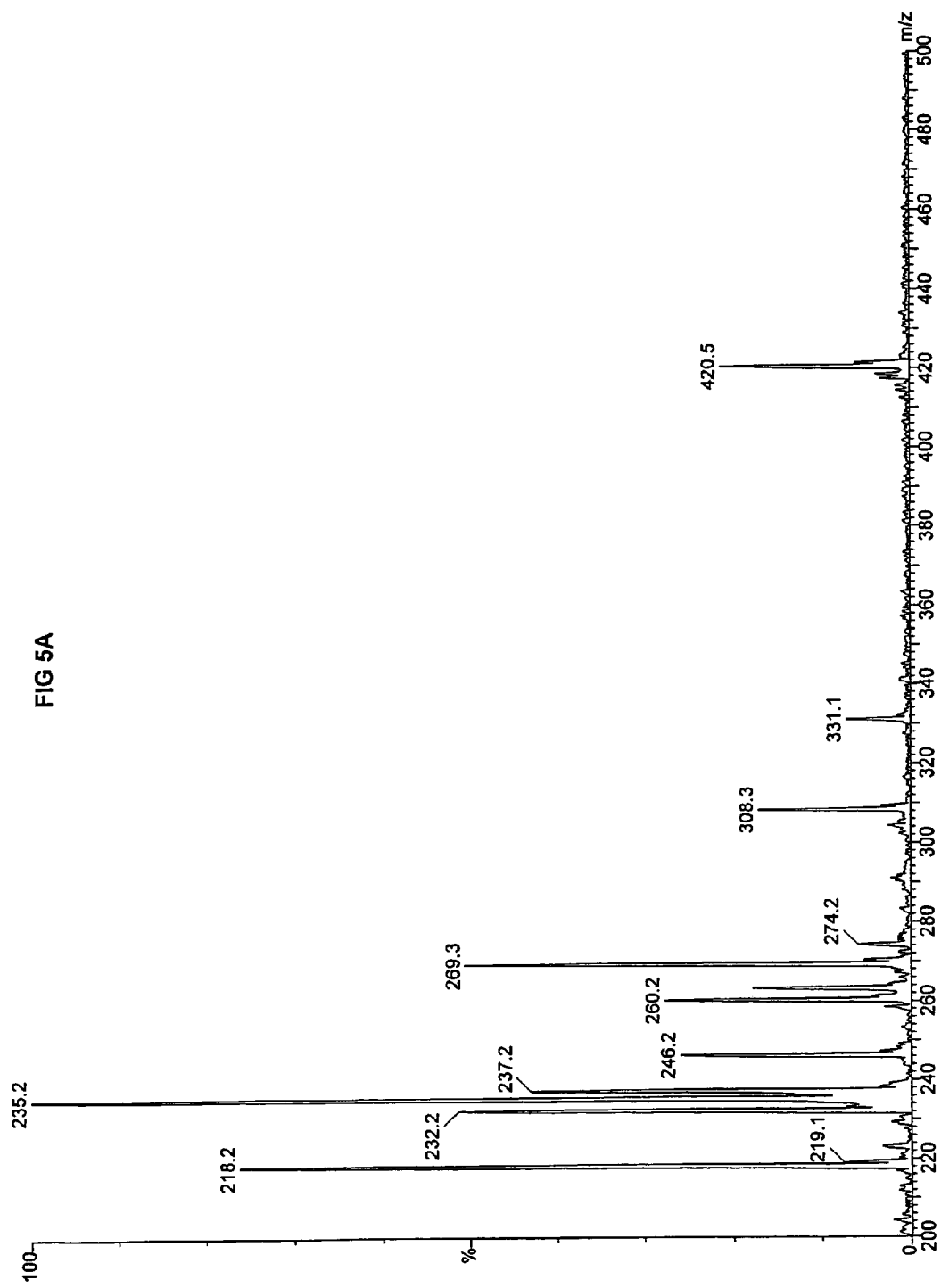
FIG. 5A is a graph depicting a tandem mass spectrometry profile for normal fibroblasts treated with D3-C7 (7-$^2$H$_3$-heptanoate). Test parameters were: parents of 99FB (fast atom bombardment) and MCA acquisition. Internal standards for the profiles in FIGS. 5A-5C are located at m/z420.3 ($^2$H$_6$-palmitate-C16), m/z308.2 ($^2$H$_6$-octanoate-C8), m/z269.1 ($^2$H$_9$-isovaleric-C5), and m/z237.0 ($^2$H$_5$-propionate-C3), wherein m/z is the mass:charge ratio. The peak at m/z291 represents D3-C7 (7-$^2$H$_3$-heptanoate). The peak at m/z235 represents D3-C3 (3-$^2$H$_3$-propionate), the end point of odd-carbon degradation.
Figure 5B:
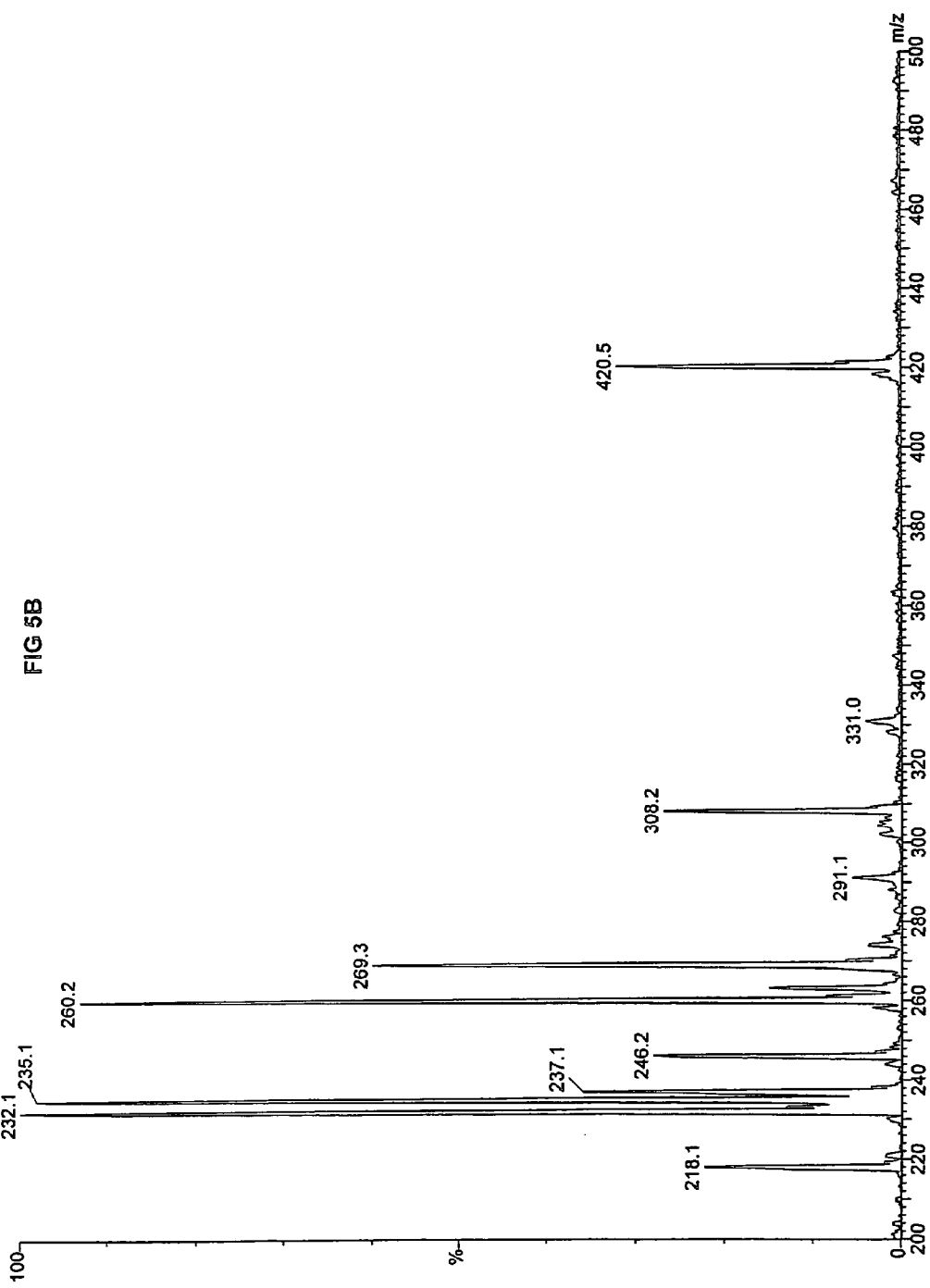
FIG. 5B is a graph depicting a tandem mass spectrometry profile for fibroblasts treated with D3-C7 (7-$^2$H$_3$-heptanoate). The fibroblasts were obtained from a child who suffered from carnitine palmitoyltransferase I (CPT I) deficiency. Test parameters were: parents of 99FB (fast atom bombardment) and MCA acquisition. The peak at m/z291 represents D3-C7 (7-$^2$H$_3$-heptanoate). The peak at m/z235.0 represents D3-C3 (3-$^2$H$_3$-propionate), the end point of odd-carbon degradation.
Figure 5C:
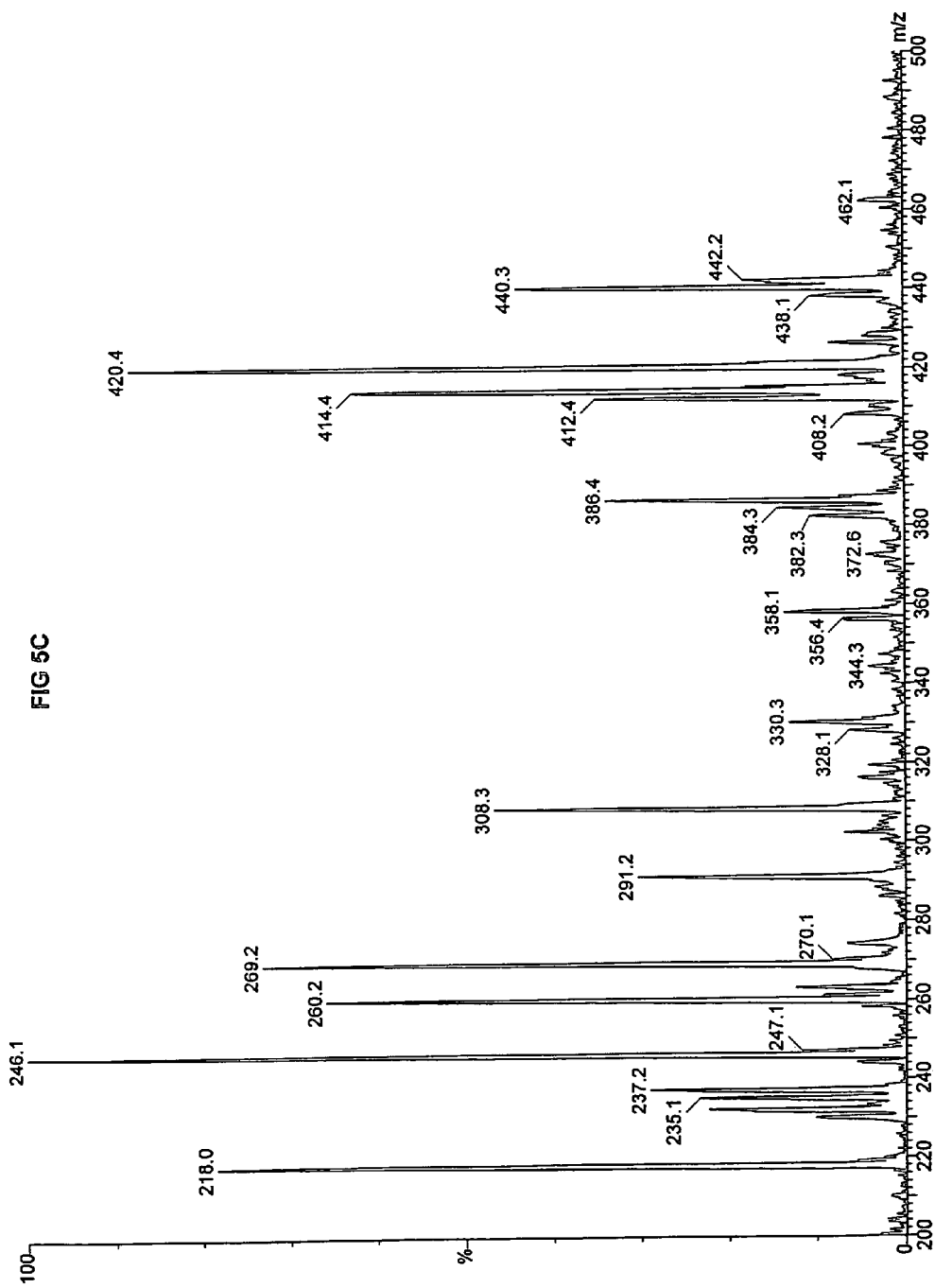
FIG. 5C is a graph depicting a tandem mass spectrometry profile for fibroblasts treated with D3-C7 (7-$^2$H$_3$-heptanoate). The fibroblasts were obtained from a child who suffered from translocase deficiency. Test parameters were: parents of 99FB (fast atom bombardment) and MCA acquisition. The peak at m/z291.3 represents D3-C7 (7-$^2$H$_3$-heptanoate). The peak at m/z235 represents D3-C3 (3-$^2$H$_3$-propionate), the end point of odd-carbon degradation.
Figure 5D:
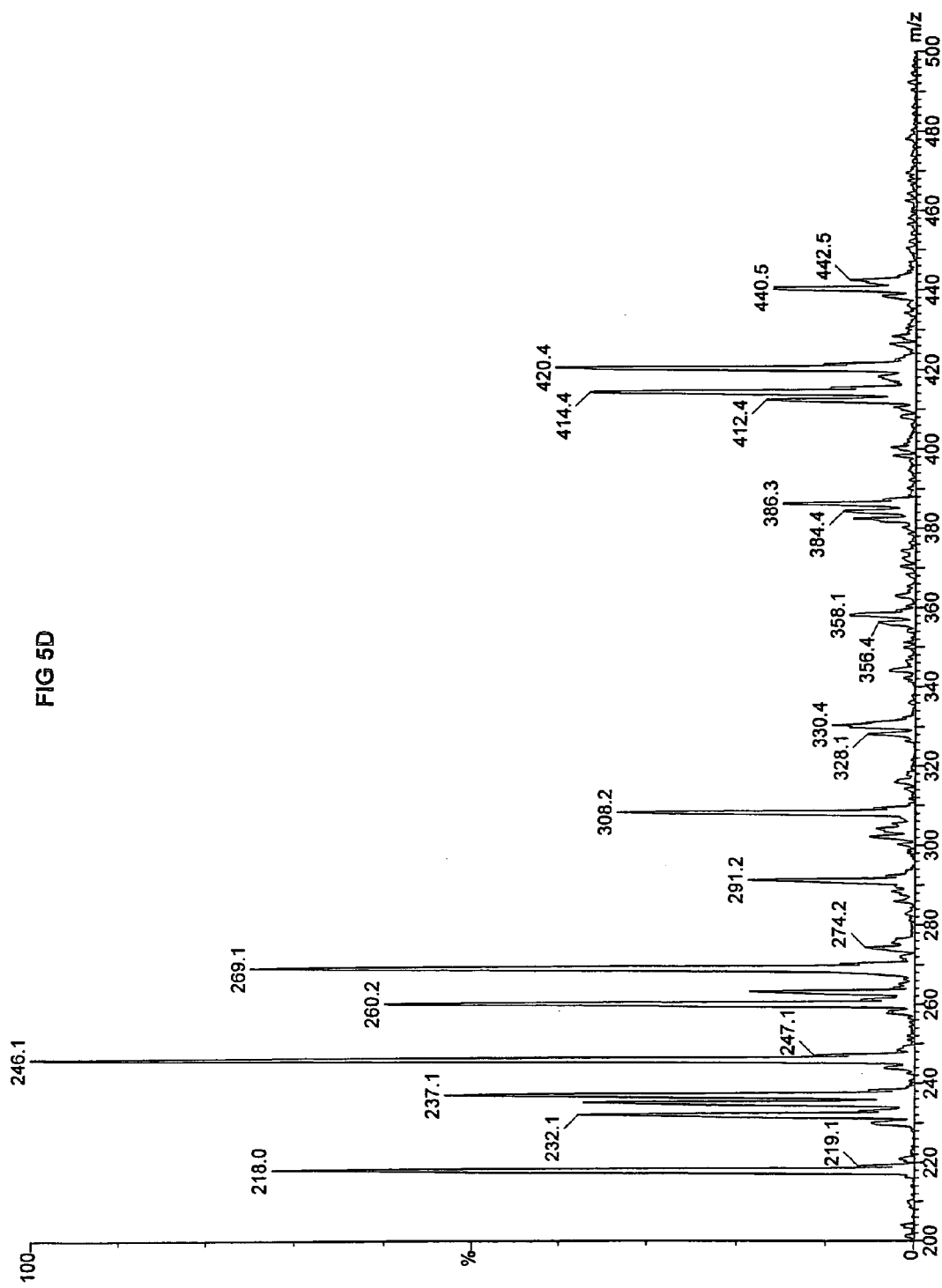
FIG. 5D is a graph depicting a tandem mass spectrometry profile for fibroblasts treated with D3-C7 (7-$^2$H$_3$-heptanoate). The fibroblasts were obtained from a child who suffered from carnitine palmitoyltransferase II (CPT II) deficiency. Test parameters were: parents of 99FB (fast atom bombardment) and MCA acquisition. Internal standards for the profiles in FIGS. 5D-5F are located at m/z420.4 ($^2$H$_6$-palmitate-C16), m/z308.3 ($^2$H$_6$-octanoate-C8), m/z269.2 ($^2$H$_9$-isovaleric-C5), and m/z237.1 ($^2$H$_5$-propionate-C3). The peak at m/z291.1 represents D3-C7 (7-$^2$H$_3$-heptanoate). The peak at m/z235 represents D3-C3 (3-$^2$H$_3$-propionate), the end point of odd-carbon degradation.
Figure 5E:
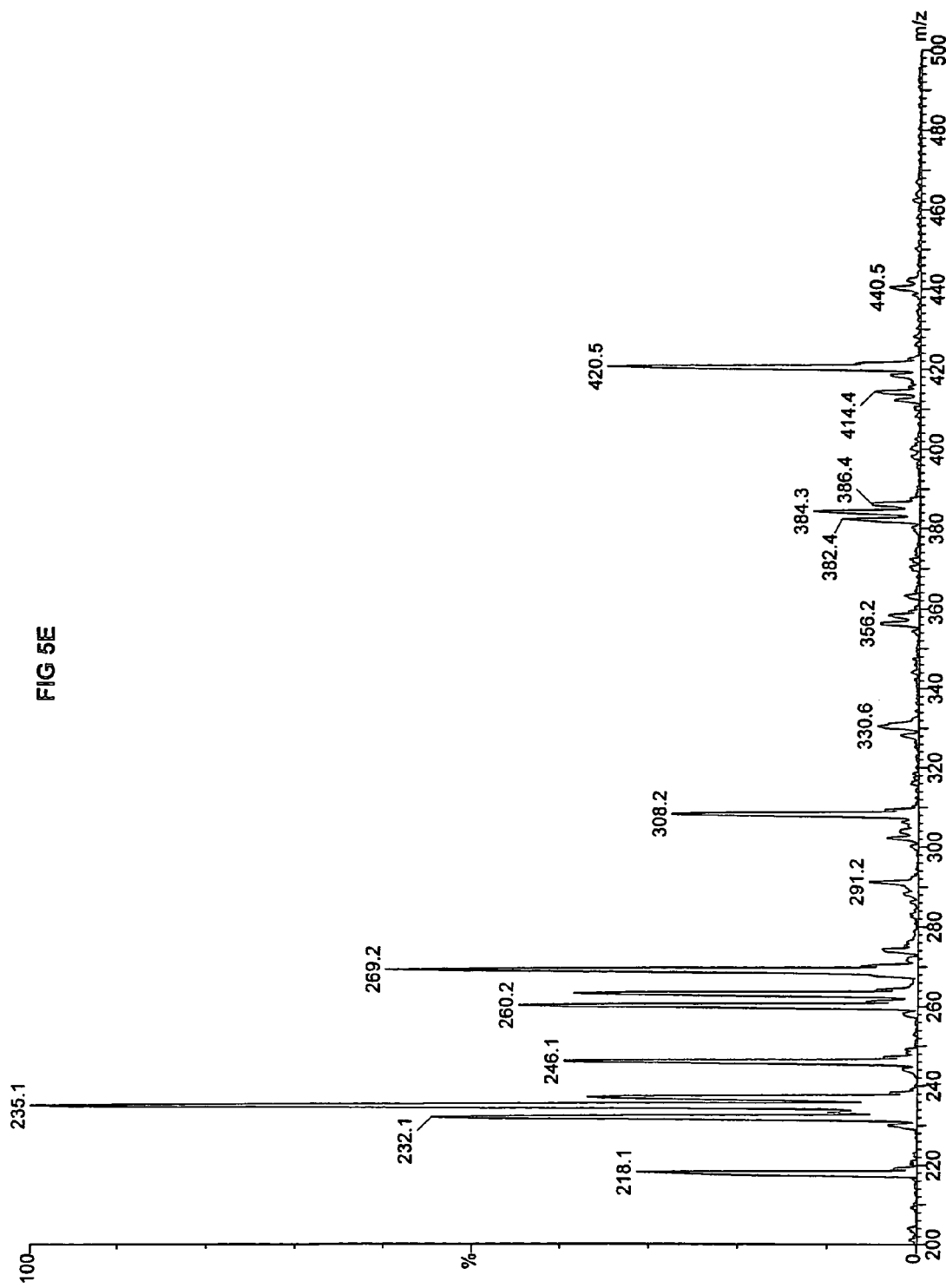
FIG. 5E is a graph depicting a tandem mass spectrometry profile for fibroblasts treated with D3-C7 (7-$^2$H$_3$-heptanoate). The fibroblasts were obtained from a child who suffered from the "cardiac" form of very-long-chain acyl-CoA dehydrogenase (VLCAD-C) deficiency. Test parameters were: parents of 99FB (fast atom bombardment) and MCA acquisition. The peak at m/z291 represents D3-C7 (7-$^2$H$_3$-heptanoate). The peak at m/z235.1 represents D3-C3 (3-$^2$H$_3$-propionate), the end point of odd-carbon degradation.
Figure 5F:
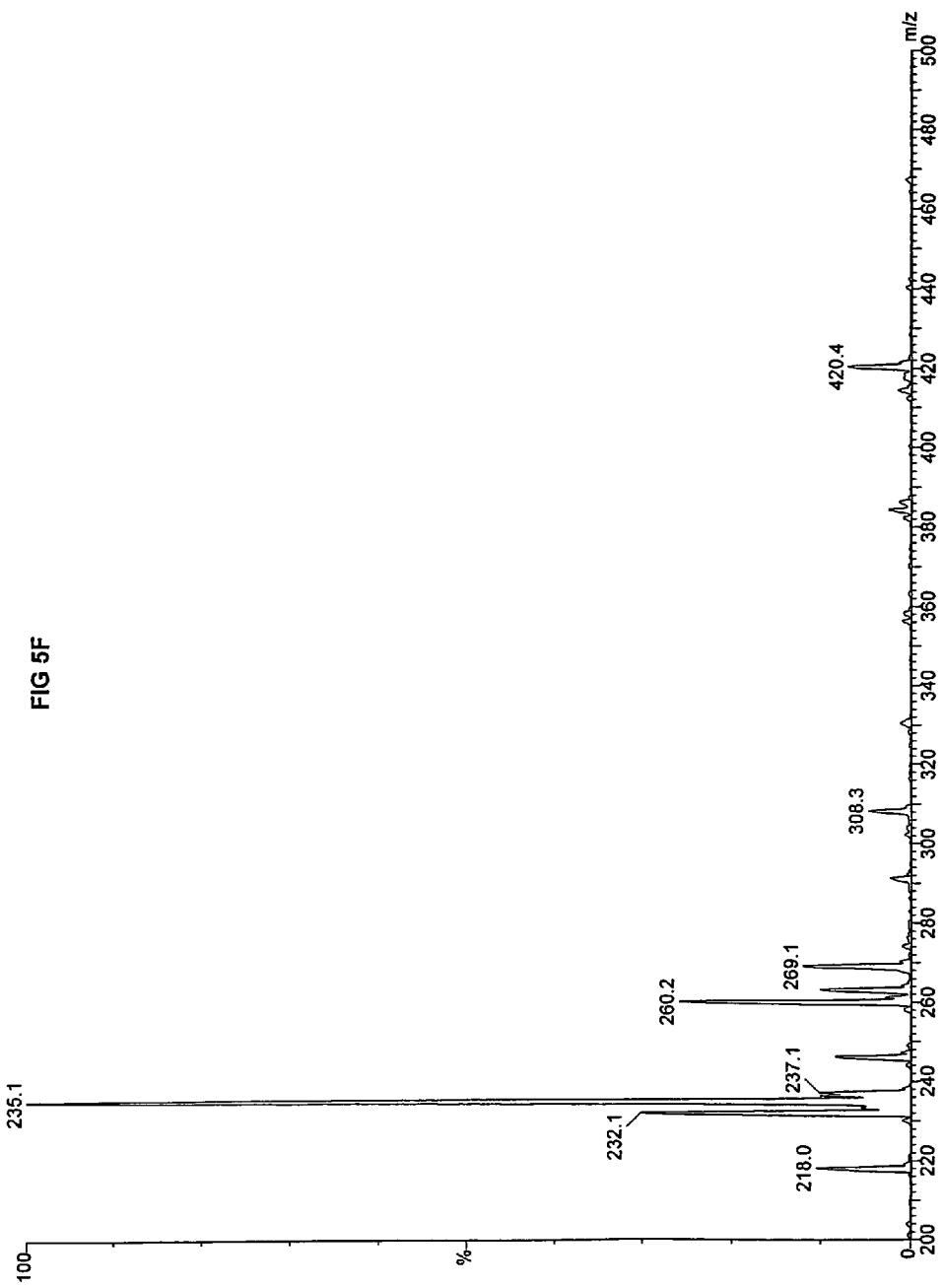
FIG. 5F is a graph depicting a tandem mass spectrometry profile for fibroblasts treated with D3-C7 (7-$^2$H$_3$-heptanoate). The fibroblasts were obtained from a child who suffered from the "hypoglycemic" form of very-long-chain acyl-CoA dehydrogenase (VLCAD-H) deficiency. Test parameters were: parents of 99FB (fast atom bombardment) and MCA acquisition. The peak at m/z291.4 represents D3-C7 (7-$^2$H$_3$-heptanoate). The peak at m/z235.1 represents D3-C3 (3-$^2$H$_3$-propionate), the end point of odd-carbon degradation.
Figure 5G:
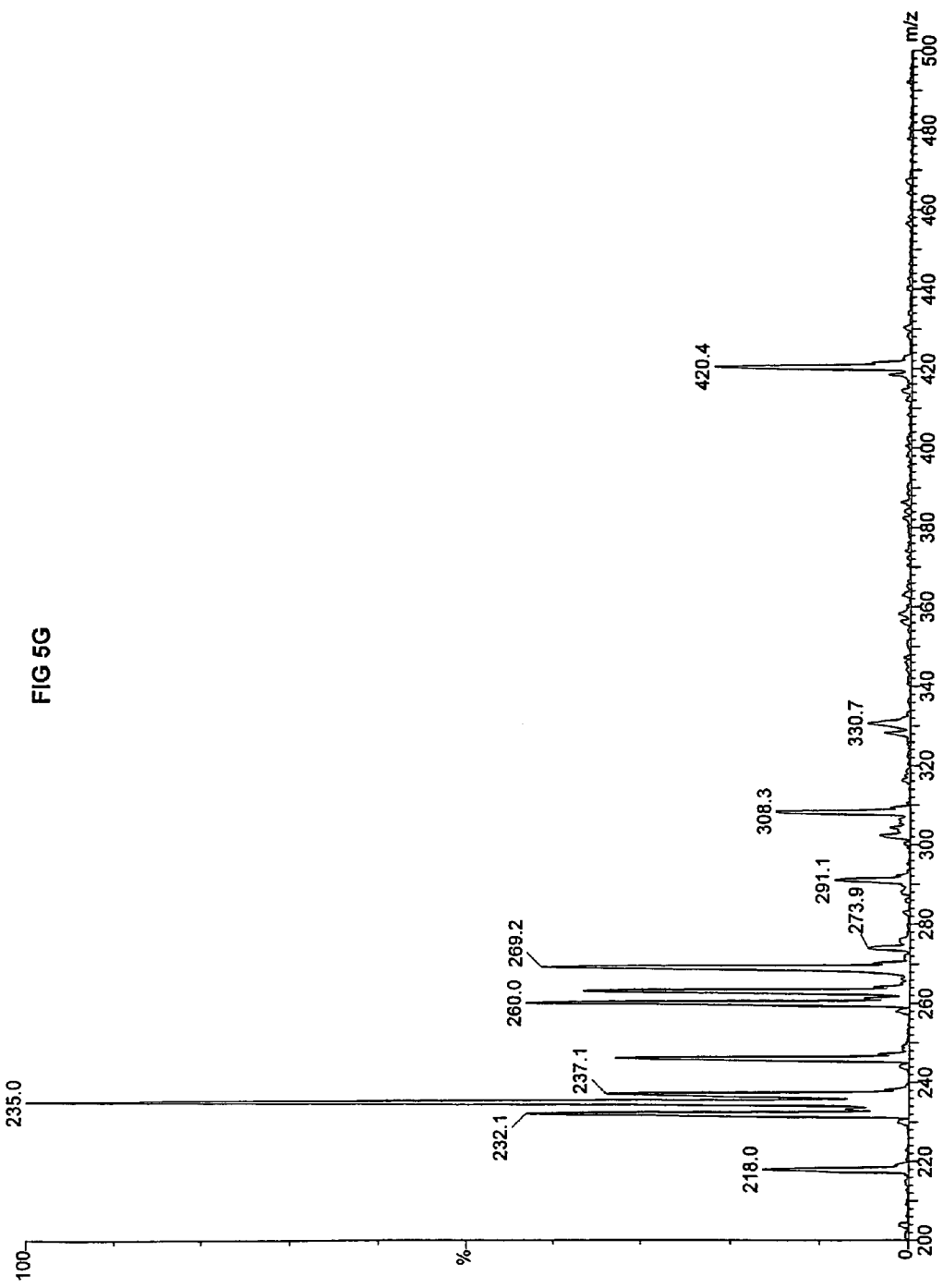
FIG. 5G is a graph depicting a tandem mass spectrometry profile for fibroblasts treated with D3-C7 (7-$^2$H$_3$-heptanoate). The fibroblasts were obtained from a child who suffered from mitochondrial trifunctional protein (TRIFUNCTIONAL) deficiency. Test parameters were: parents of 99FB (fast atom bombardment) and MCA acquisition. Internal standards for the profiles in FIGS. 5G-5I are located at m/z420.3 ($^2$H$_6$-palmitate-C16), m/z308.1 ($^2$H$_6$-octanoate-C8), m/z269.0
Figure 5H:
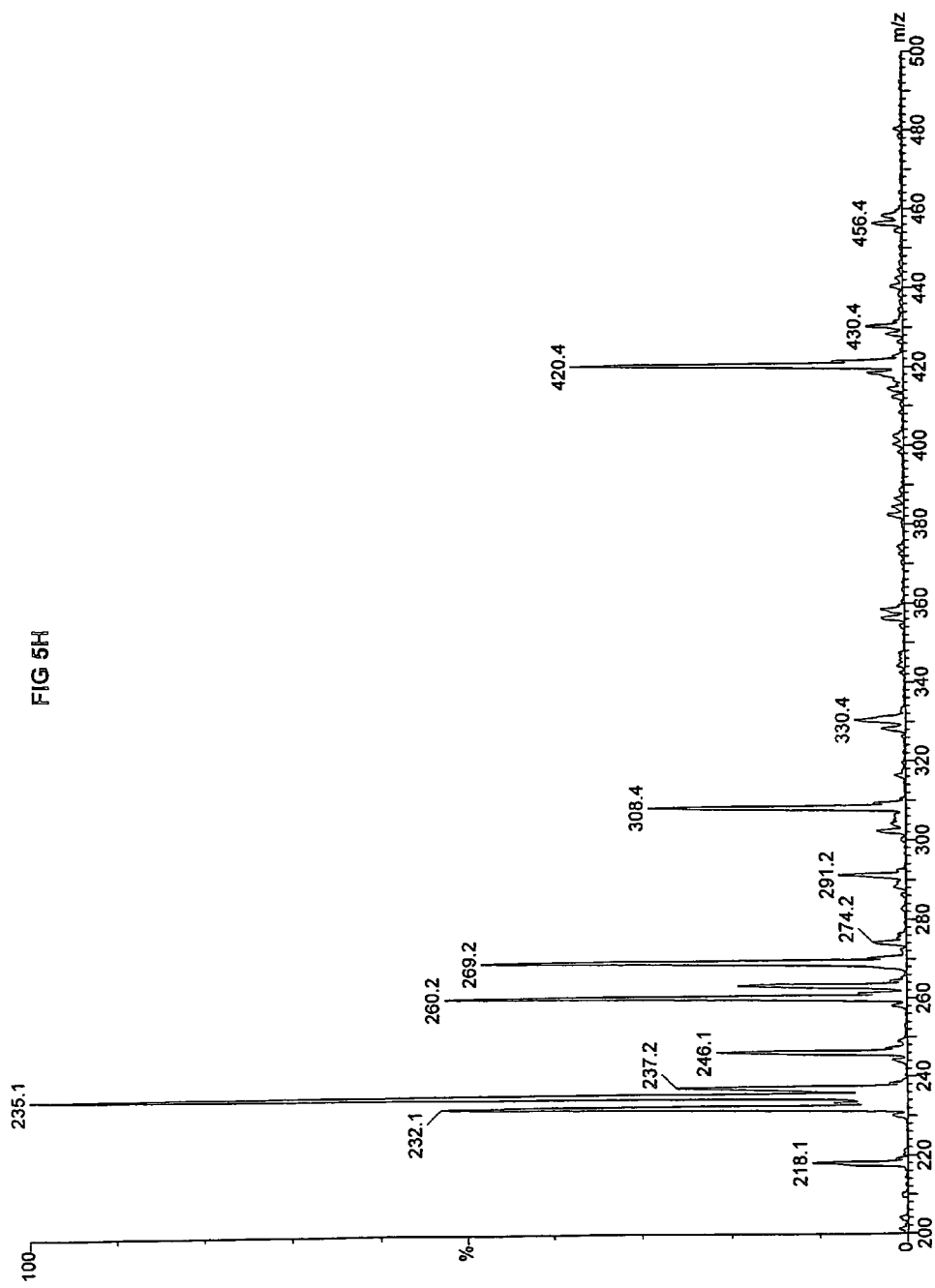

FIG. 5H is a graph depicting a tandem mass spectrometry profile for fibroblasts treated with D3-C7 (7-$^2H_3$-heptanoate). The fibroblasts were obtained from a child who suffered from long-chain L-3-hydroxy-acyl-CoA dehydrogenase (LCHAD) deficiency. Test parameters were: parents of 99FB (fast atom bombardment) and MCA acquisition. The peak at m/z291.1 represents D3-C7 (7-$^2H_3$-heptanoate). The peak at m/z235.1 represents D3-C3 (3-$^2H_3$-propionate), the end point of odd-carbon degradation.

Figure 5I:
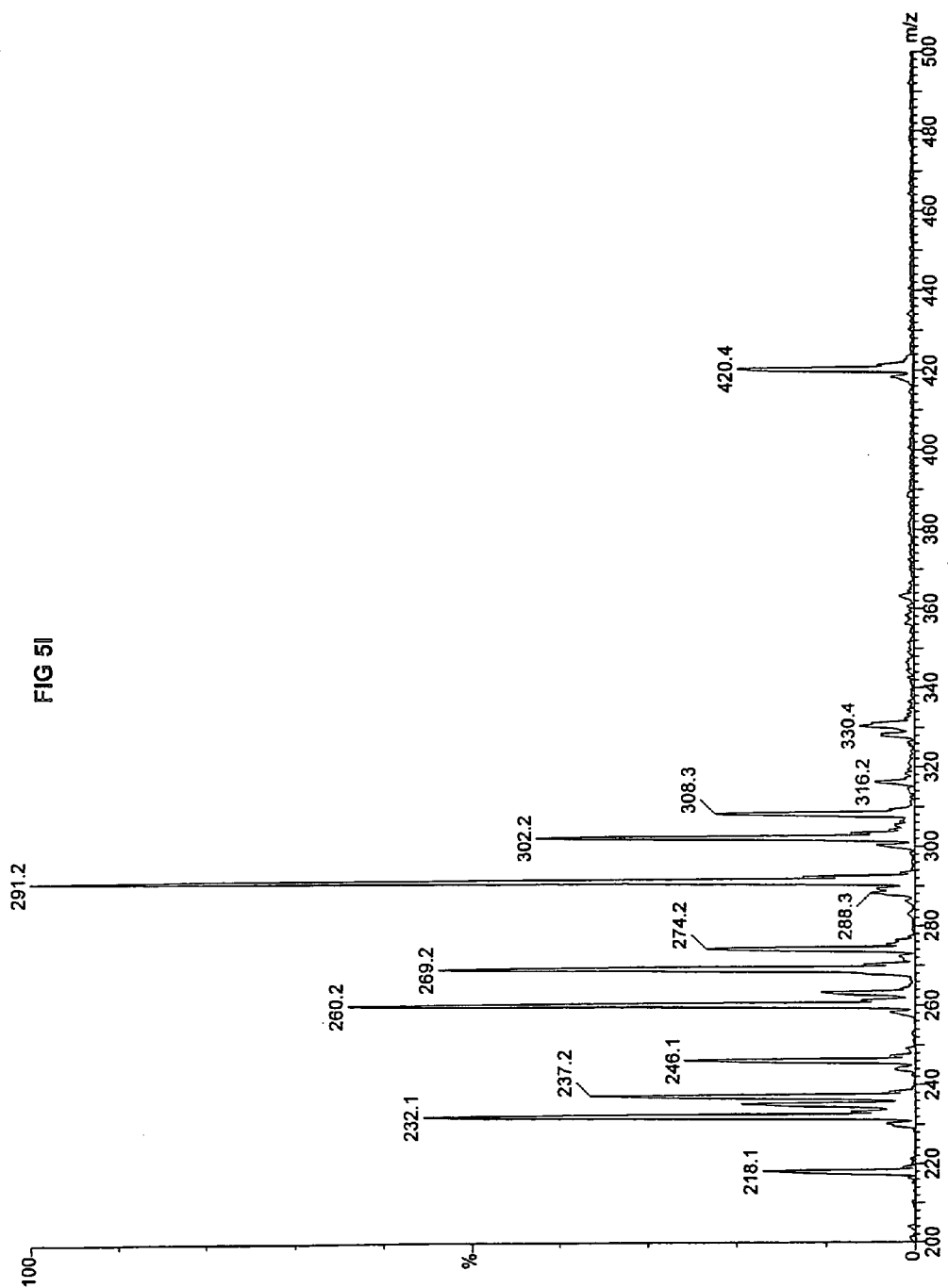

FIG. 5I is a graph depicting a tandem mass spectrometry profile for fibroblasts treated with D3-C7 (7-$^2H_3$-heptanoate). The fibroblasts were obtained from a child who suffered from medium-chain acyl-CoA dehydrogenase (MCAD) deficiency. Test parameters were: parents of 99FB (fast atom bombardment) and MCA acquisition. The peak at m/z291.2 represents D3-C7 (7-$^2H_3$-heptanoate). The peak at m/z235 represents D3-C3 (3-$^2H_3$-propionate), the end point of odd-carbon degradation.

Figure 5J:
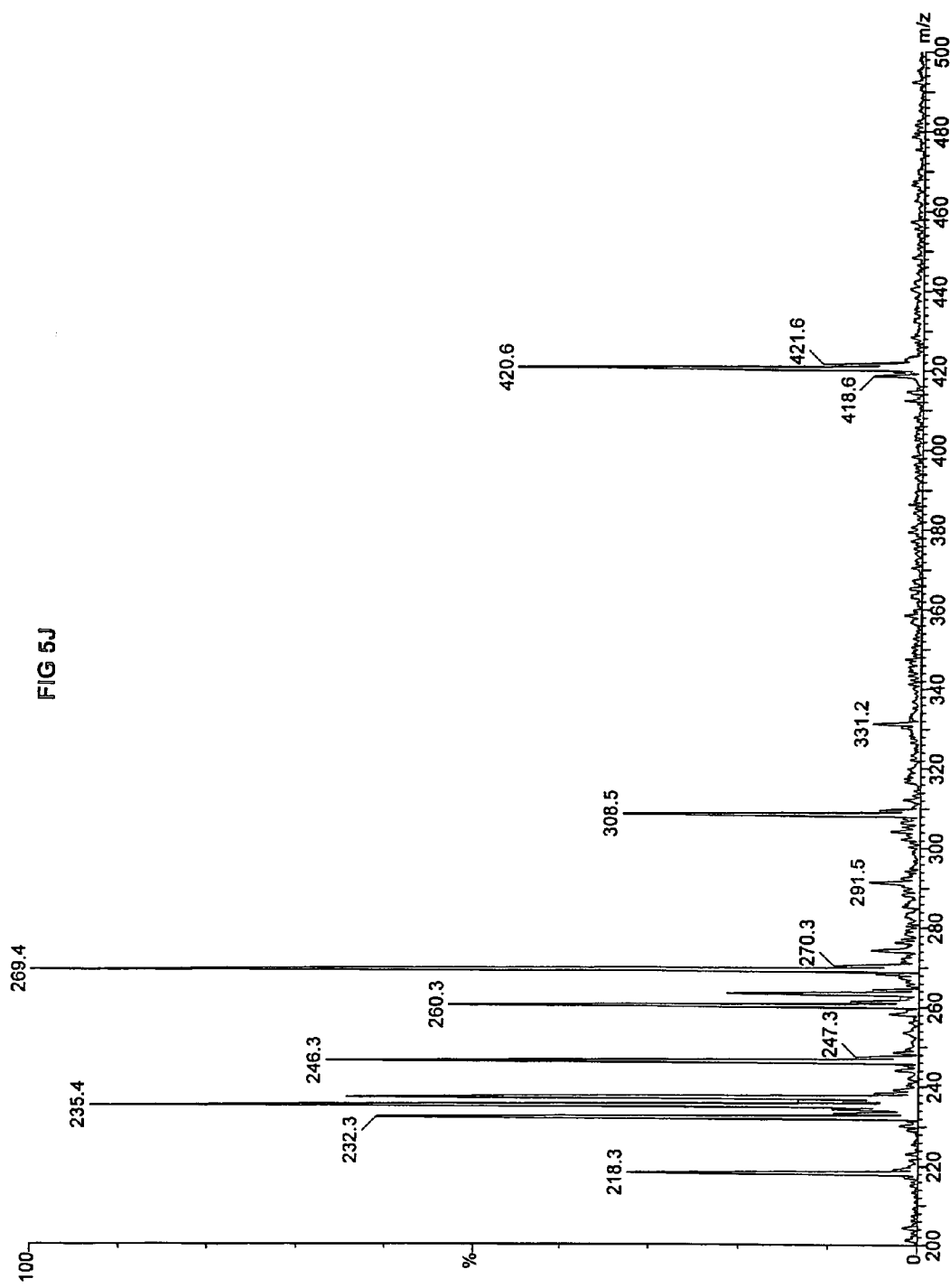
Figure 5K:
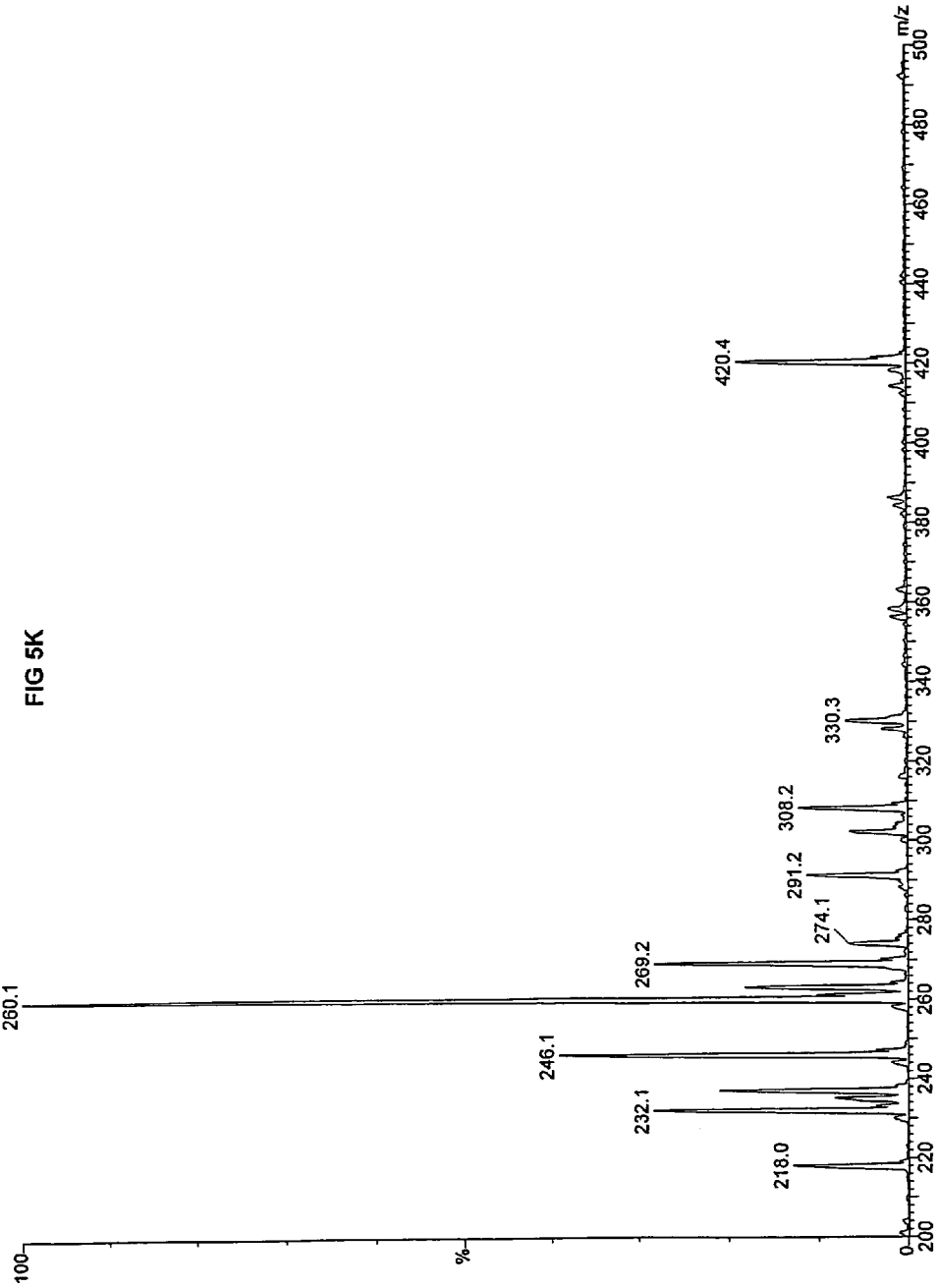
Figure 5L:
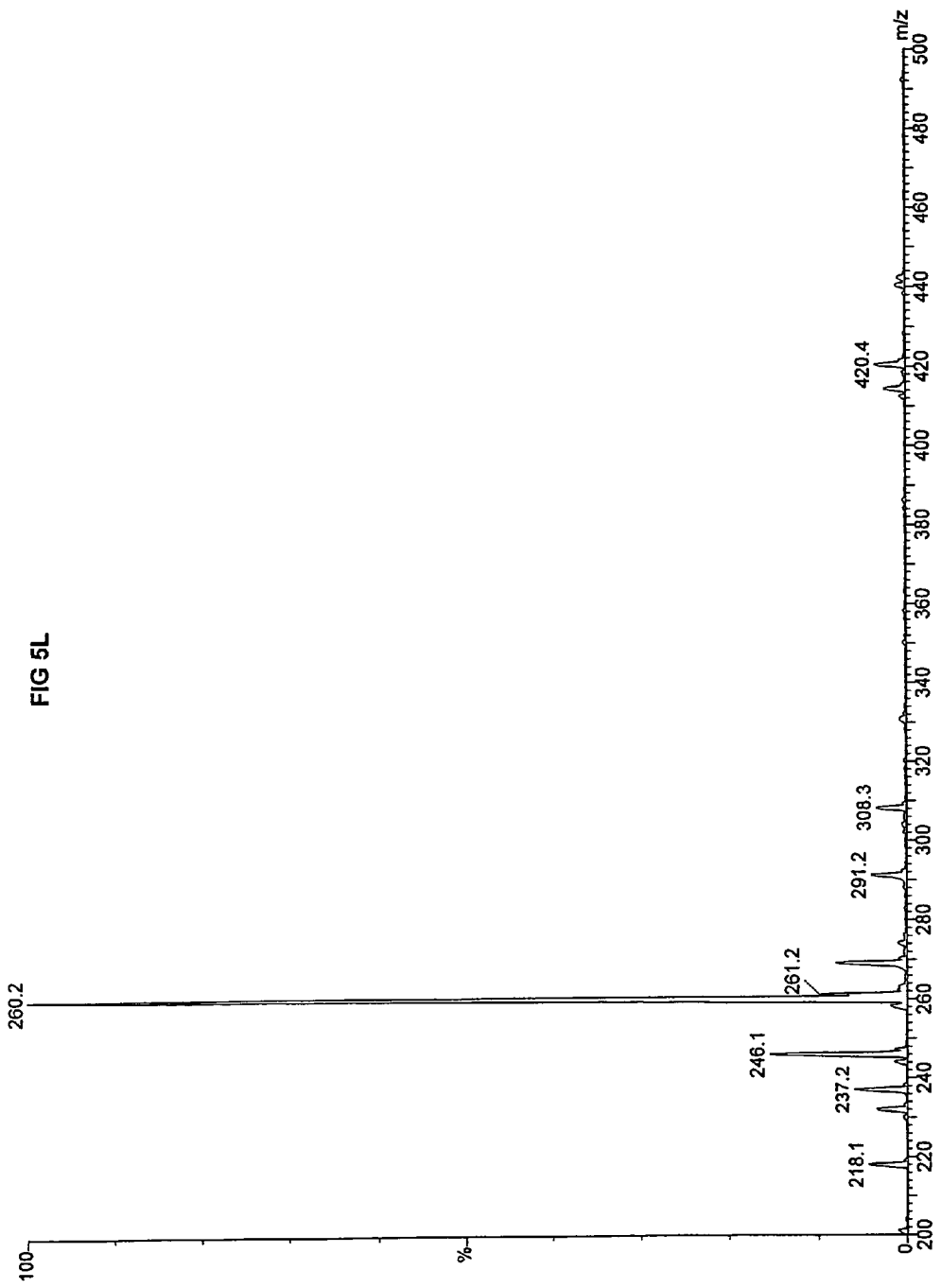

FIG. 5J is a graph depicting a tandem mass spectrometry profile for fibroblasts treated with D3-C7 (7-$^2H_3$-heptanoate). The fibroblasts were obtained from a child who suffered from short-chain acyl-CoA dehydrogenase (SCAD) deficiency. Test parameters were: parents of 99FB (fast atom bombardment) and MCA acquisition. Internal standards for the profiles in FIGS. 5J-5L are located at m/z420.4 ($^2H_6$-palmitate-C16), m/z308.0 ($^2H_6$-octanoate-C8), m/z269.2 ($^2H_9$-isovaleric-C5), and m/z237 ($^2H_5$-propionate-C3). The peak at m/z291.1 represents D3-C7 (7-$^2H_3$-heptanoate). The peak at m/z235.1 represents D3-C3 (3-$^2$H3-propionate), the end point of odd-carbon degradation.

FIG. 5K is a graph depicting a tandem mass spectrometry profile for fibroblasts treated with D3-C7 (7-$^2H_3$-heptanoate). The fibroblasts were obtained from a child who suffered from electron transfer flavoprotein QO dehydrogenase-mild (ETF-DH mild) deficiency. Test parameters were: parents of 99FB (fast atom bombardment) and MCA acquisition. The peak at m/z291.3 represents D3-C7 (7-$^2H_3$-heptanoate).

FIG. 5L is a graph depicting a tandem mass spectrometry profile for fibroblasts treated with D3-C7 (7-$^2H_3$-heptanoate). The fibroblasts were obtained from a child who suffered from electron transfer flavoprotein QO dehydrogenase-severe (ETF-DH severe) deficiency. Test parameters were: parents of 99FB (fast atom bombardment) and MCA acquisition. The peak at m/z291 represents D3-C7 (7-$^2H_3$-heptanoate).

Figure 6A:
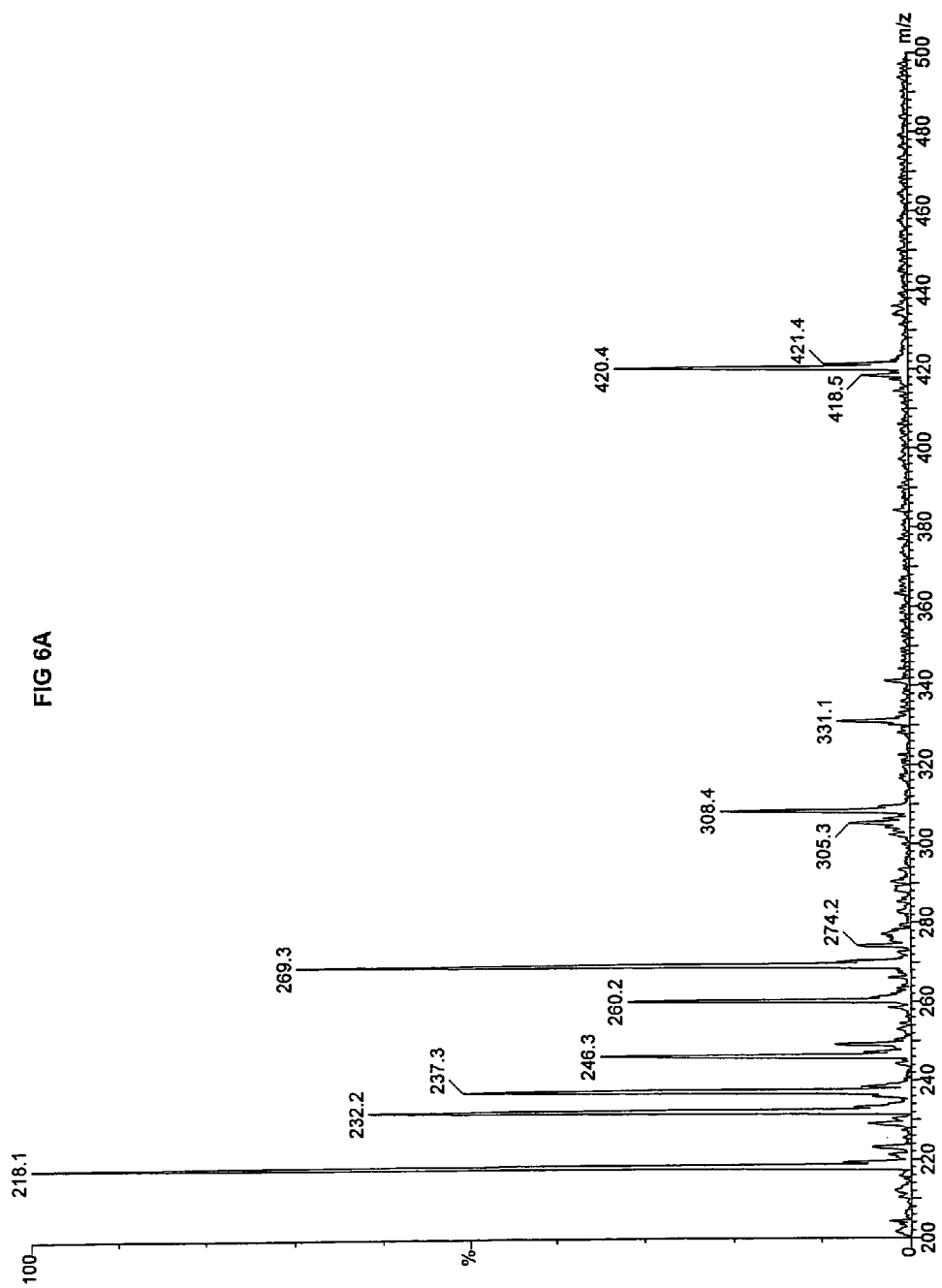
Figure 6B:
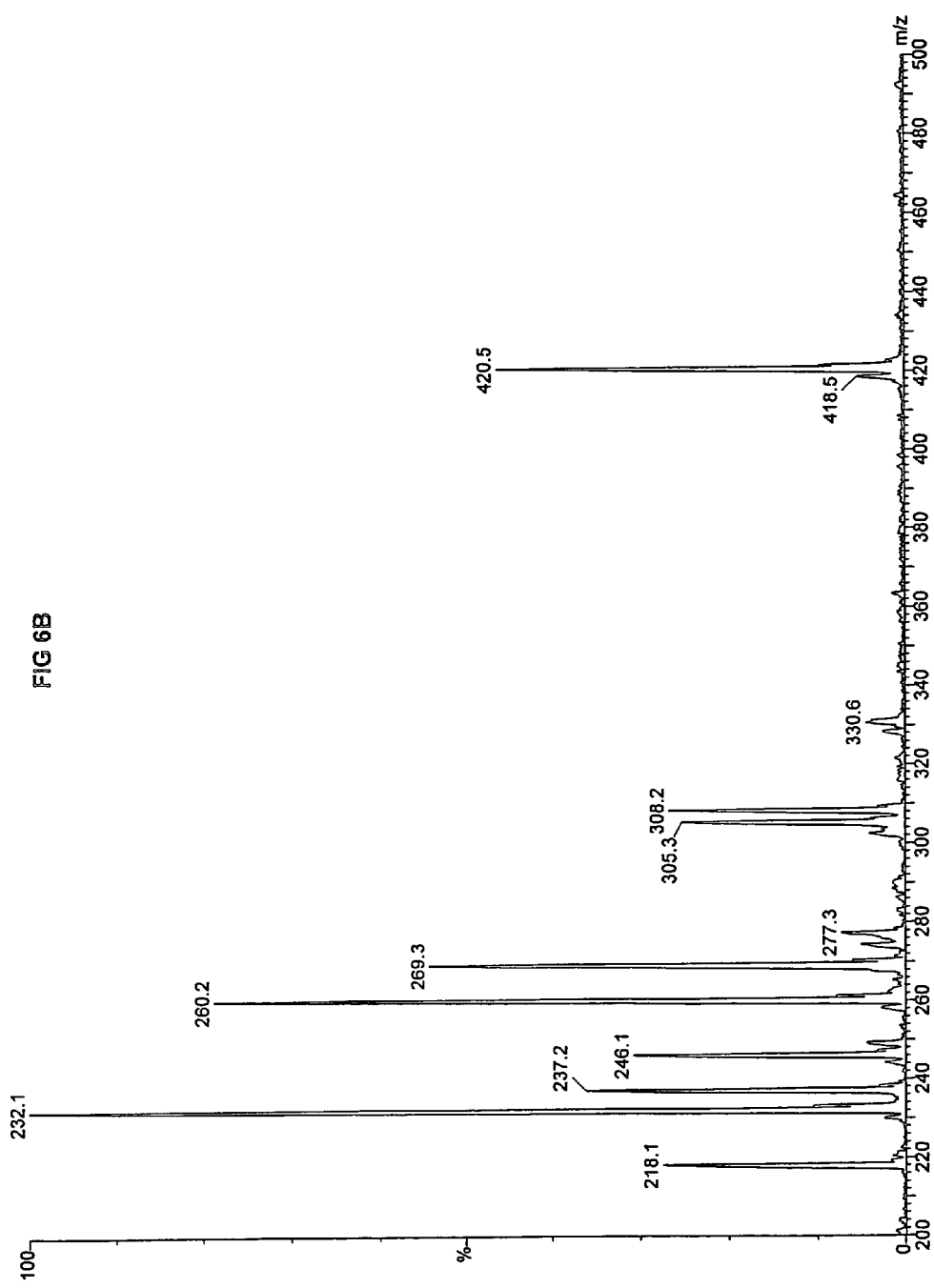
Figure 6C:
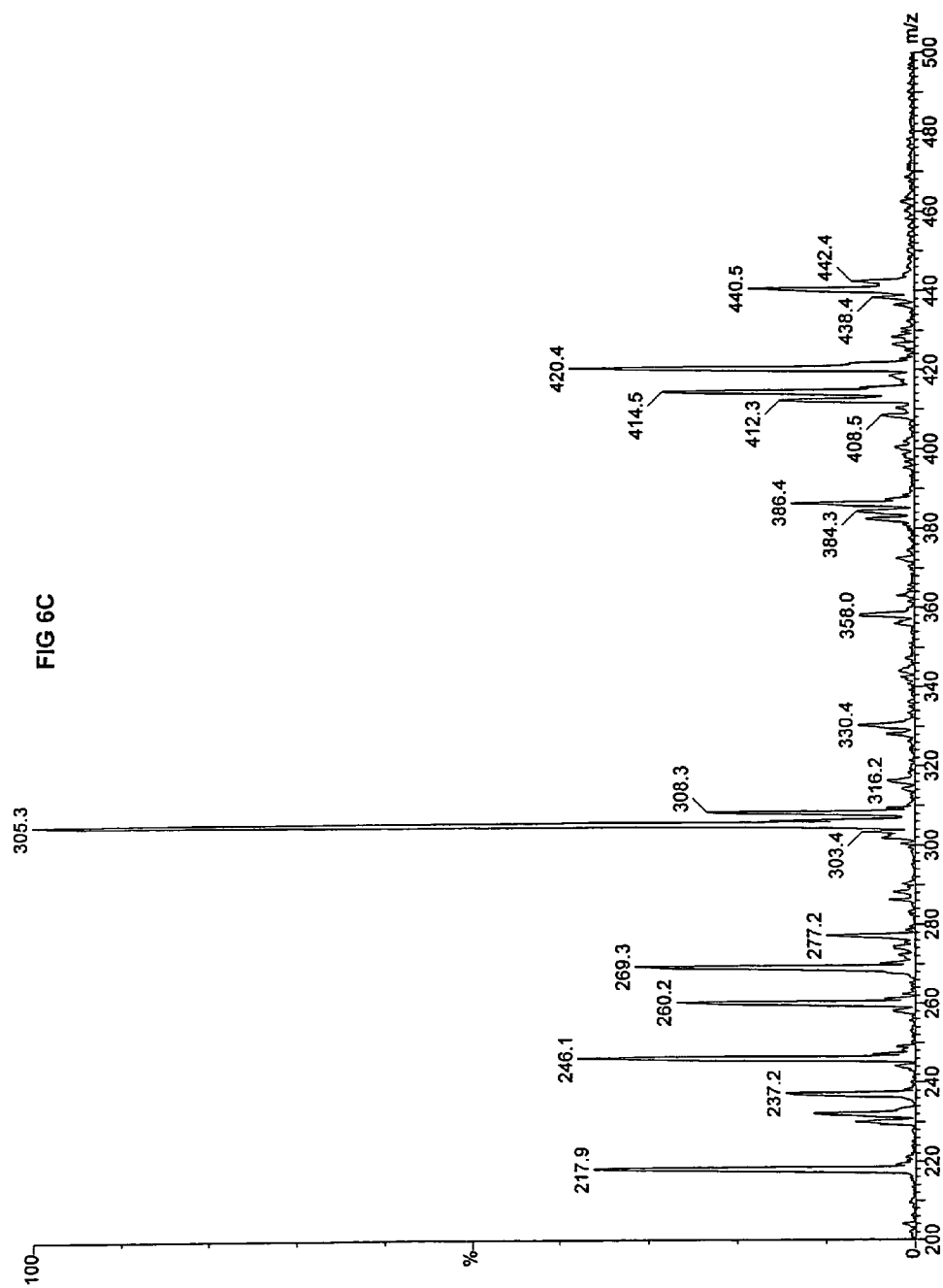

FIG. 6A is a graph depicting a tandem mass spectrometry profile for normal fibroblasts treated with D3-C8 (8-$^2H_3$-octanoate). Test parameters were: parents of 99FB (fast atom bombardment) and MCA acquisition. Internal standards for the profiles in FIGS. 6A-6C are located at m/z420.4 ($^2H_6$-palmitate-C16), m/z308.3 ($^2H_6$-octanoate-C8), m/z269.2 ($^2H_9$-isovaleric-C5), and m/z237.1 ($^2H_5$-propionate-C3). The peak at m/z305.3 represents D3-C8 (8-$^2H_3$-octanoate).

FIG. 6B is a graph depicting a tandem mass spectrometry profile for fibroblasts treated with D3-C8 (8-$^2H_3$-octanoate). The fibroblasts were obtained from a child who suffered from carnitine palmitoyltransferase I (CPT I) deficiency. Test parameters were: parents of 99FB (fast atom bombardment) and MCA acquisition. The peak at m/z305.0 represents D3-C8 (8-$^2H_3$-octanoate).

FIG. 6C is a graph depicting a tandem mass spectrometry profile for fibroblasts treated with D3-C8 (8-$^2H_3$-octanoate). The fibroblasts were obtained from a child who suffered from translocase deficiency. Test parameters were: parents of 99FB (fast atom bombardment) and MCA acquisition. The peak at m/z305.3 represents D3-C8 (8-$^2H_3$-octanoate).

Figure 6D:
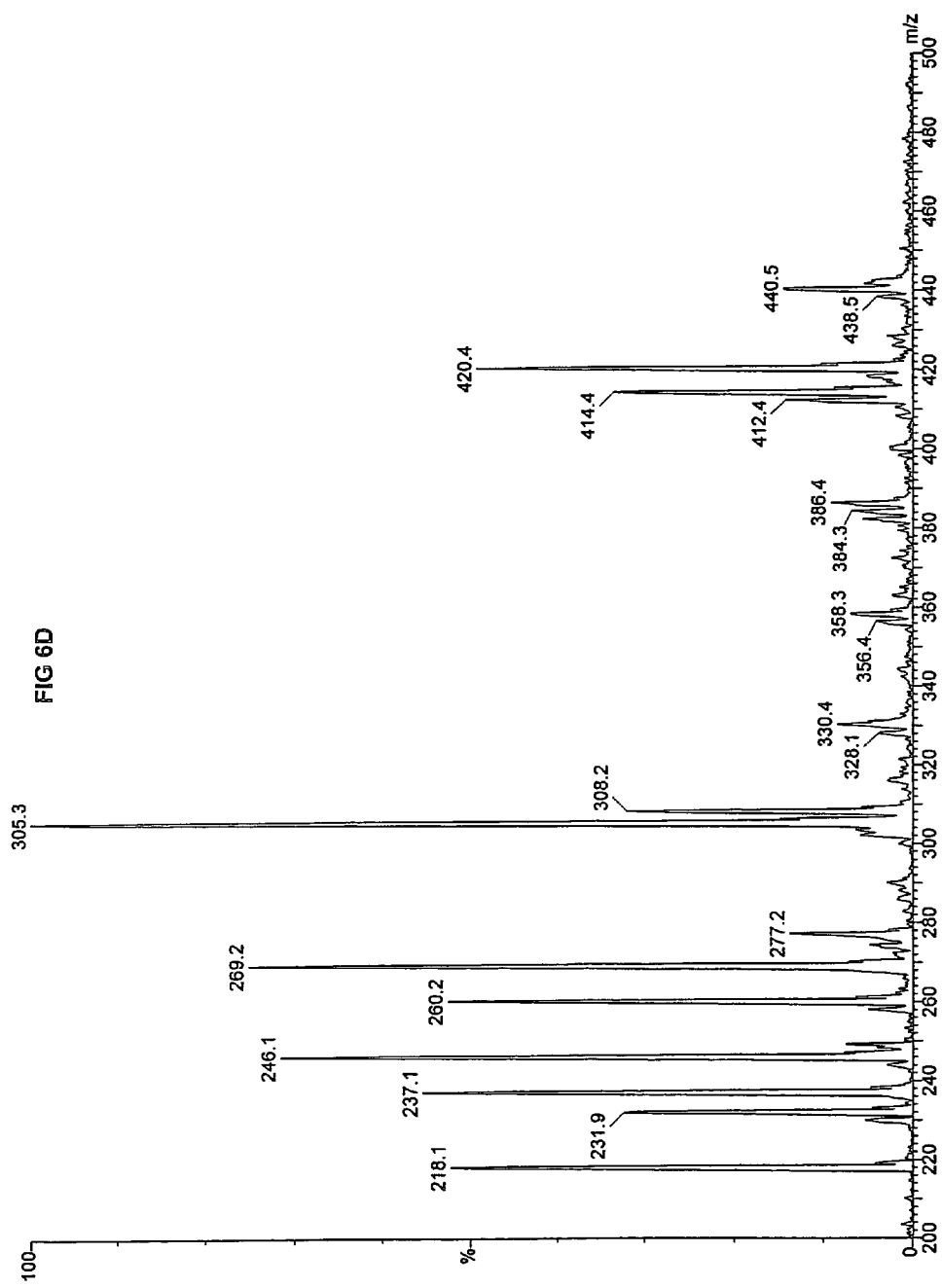
Figure 6E:
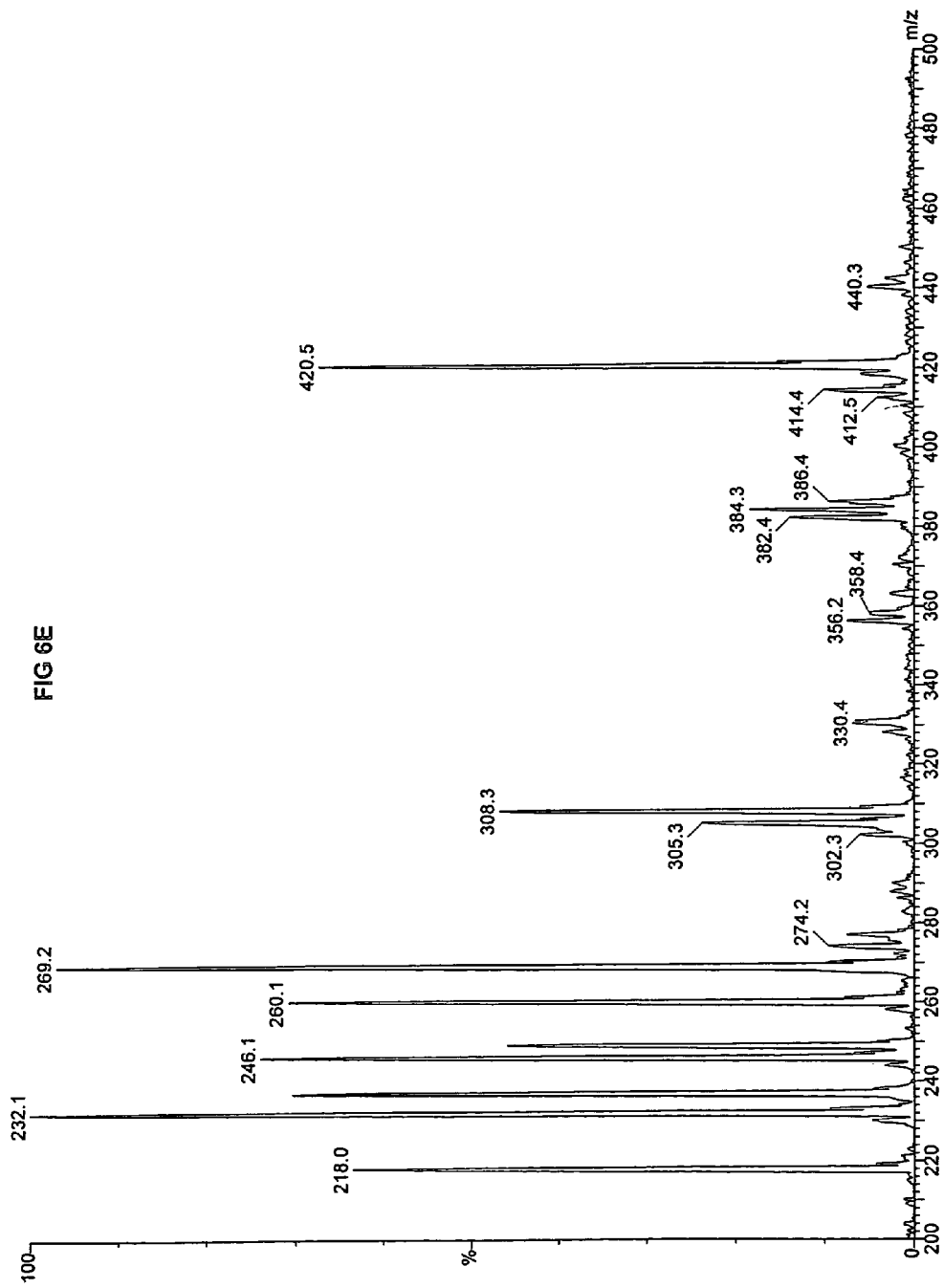
Figure 6F:
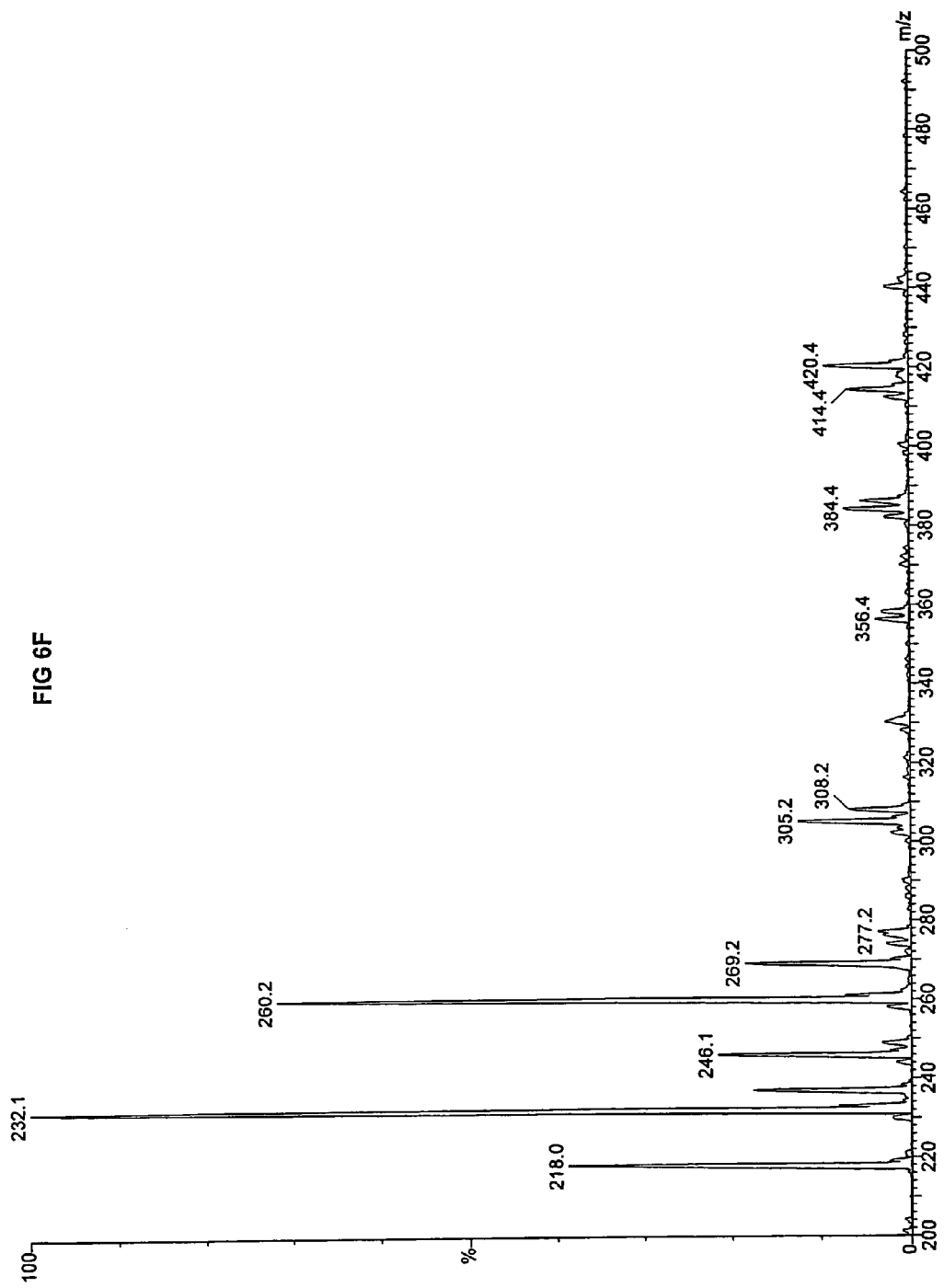

FIG. 6D is a graph depicting a tandem mass spectrometry profile for fibroblasts treated with D3-C8 (8-$^2H_3$-octanoate). The fibroblasts were obtained from a child who suffered from carnitine palmitoyltransferase II (CPT II) deficiency. Test parameters were: parents of 99FB (fast atom bombardment) and MCA acquisition. Internal standards for the profiles in FIGS. 6D-6F are located at m/z420.3 ($^2H_6$-palmitate-C16), m/z308.3 ($^2H_6$-octanoate-C8), m/z269.2 ($^2H_9$-isovaleric-C5), and m/z237.2 ($^2H_5$-propionate-C3). The peak at m/z305.3 represents D3-C8 (8-$^2H_3$-octanoate).

FIG. 6E is a graph depicting a tandem mass spectrometry profile for fibroblasts treated with D3-C8 (8-$^2H_3$-octanoate). The fibroblasts were obtained from a child who suffered from the "cardiac" form of very-long-chain acyl-CoA dehydrogenase (VLCAD-C) deficiency. Test parameters were: parents of 99FB (fast atom bombardment) and MCA acquisition. The peak at m/z305.3 represents D3-C8 (8-$^2H_3$-octanoate).

FIG. 6F is a graph depicting a tandem mass spectrometry profile for fibroblasts treated with D3-C8 (8-$^2H_3$-octanoate). The fibroblasts were obtained from a child who suffered from the "hypoglycemic" form of very-long-chain acyl-CoA dehydrogenase (VLCAD-H) deficiency. Test parameters were: parents of 99FB (fast atom bombardment) and MCA acquisition. The peak at m/z305.2 represents D3-C8 (8-$^2H_3$-octanoate).

Figure 6G:
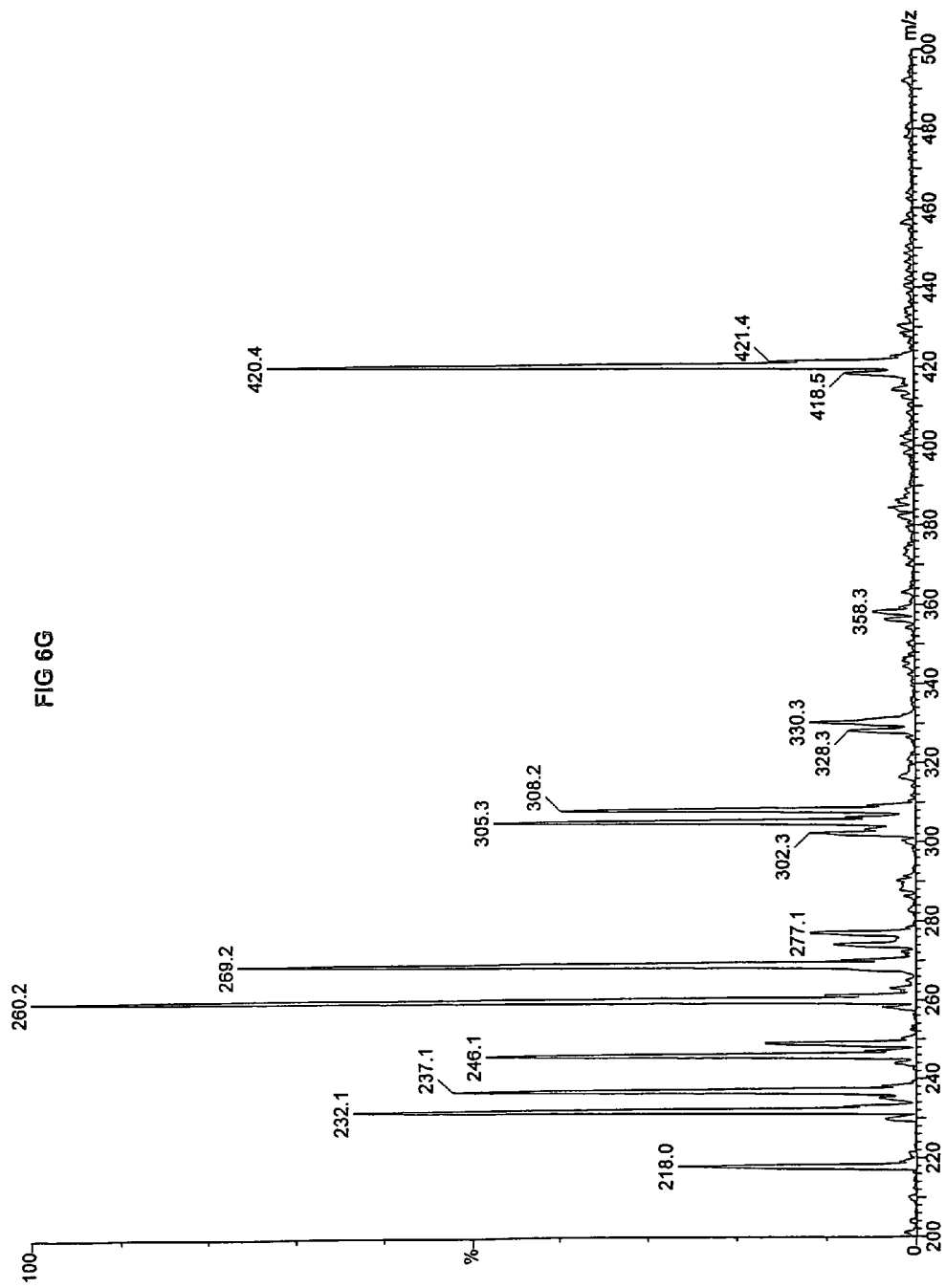
Figure 6H:
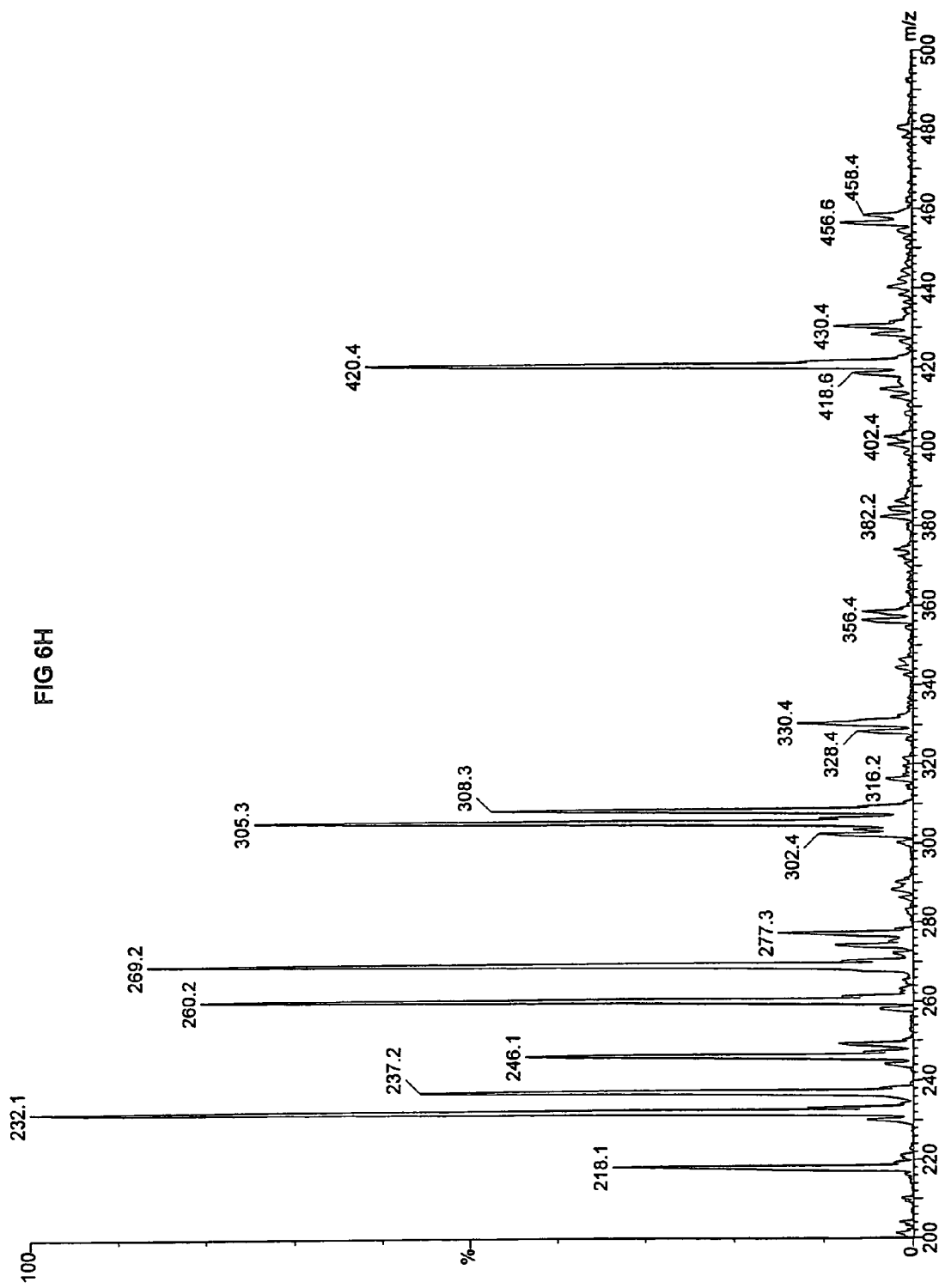
Figure 6I:
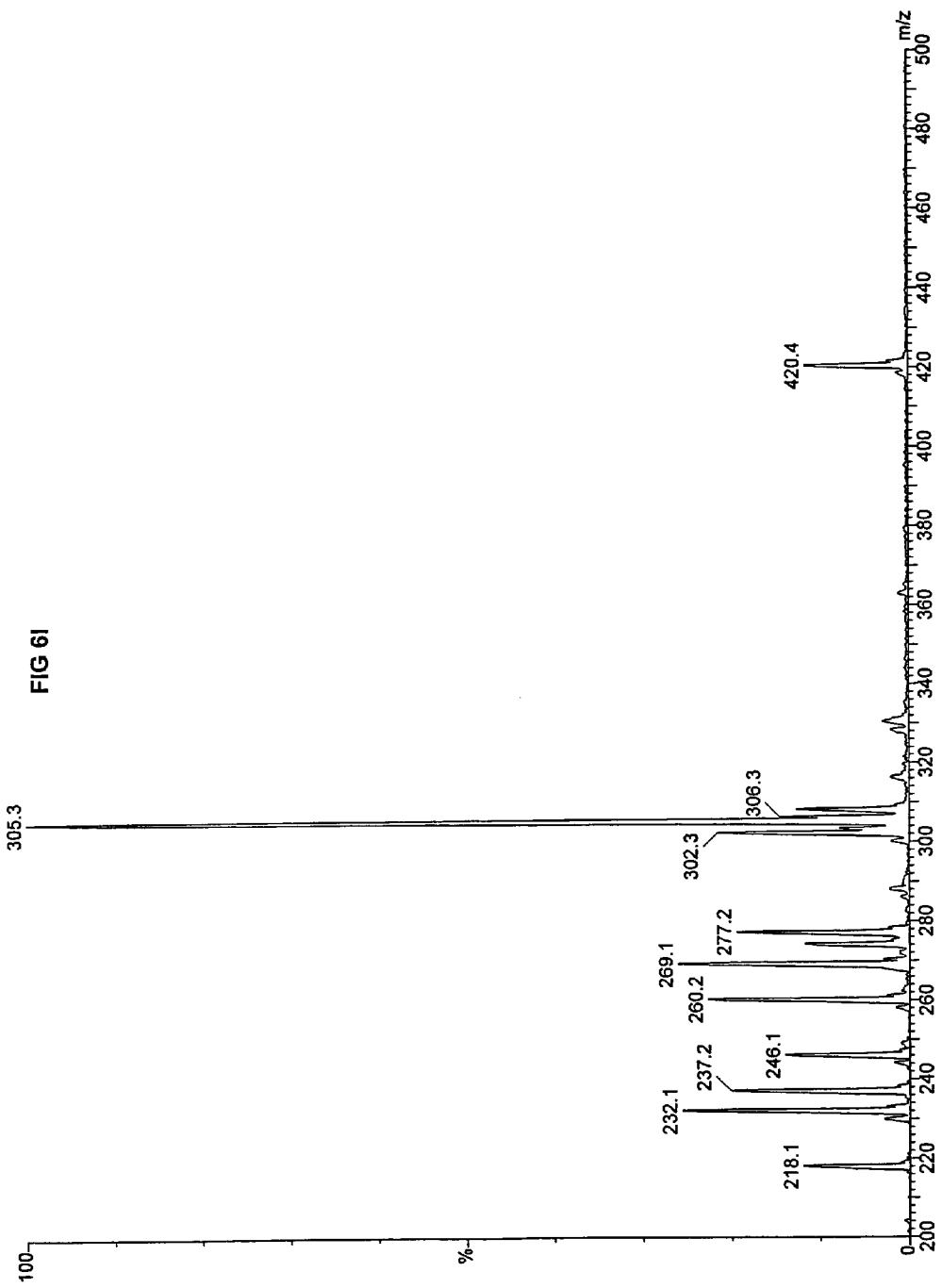

FIG. 6G is a graph depicting a tandem mass spectrometry profile for fibroblasts treated with D3-C8 (8-$^2H_3$-octanoate). The fibroblasts were obtained from a child who suffered from mitchodrial trifunctional protein (TRIFUNCTIONAL) deficiency. Test parameters were: parents of 99FB (fast atom bombardment) and MCA acquisition. Internal standards for the profiles in FIGS. 6G-6I are located at m/z420.5 (2H-palmitate-C16), m/z308.3 ($^2H_6$-octanoate-C8), m/z269.2 ($^2H_6$-isovaleric-C5), and m/z237.2 ($^2H_5$-propionate-C3). The peak at m/z305.3 represents D3-C8 (8-$^2H_3$-octanoate).

FIG. 6H is a graph depicting a tandem mass spectrometry profile for fibroblasts treated with D3-C8 (8-$^2H_3$-octanoate). The fibroblasts were obtained from a child who suffered from long-chain L-3-hydroxy-acyl-CoA dehydrogenase (LCHAD) deficiency. Test parameters were: parents of 99FB (fast atom bombardment) and MCA acquisition. The peak at m/z305 represents D3-C8 (8-$^2H_3$-octanoate).

FIG. 6I is a graph depicting a tandem mass spectrometry profile for fibroblasts treated with D3-C8 (8-$^2H_3$-octanoate). The fibroblasts were obtained from a child who suffered from medium-chain acyl-CoA dehydrogenase (MCAD) deficiency. Test parameters were: parents of 99FB (fast atom bombardment) and MCA acquisition. The peak at m/z305.2 represents D3-C8 (8-$^2H_3$-octanoate).

Figure 6J:
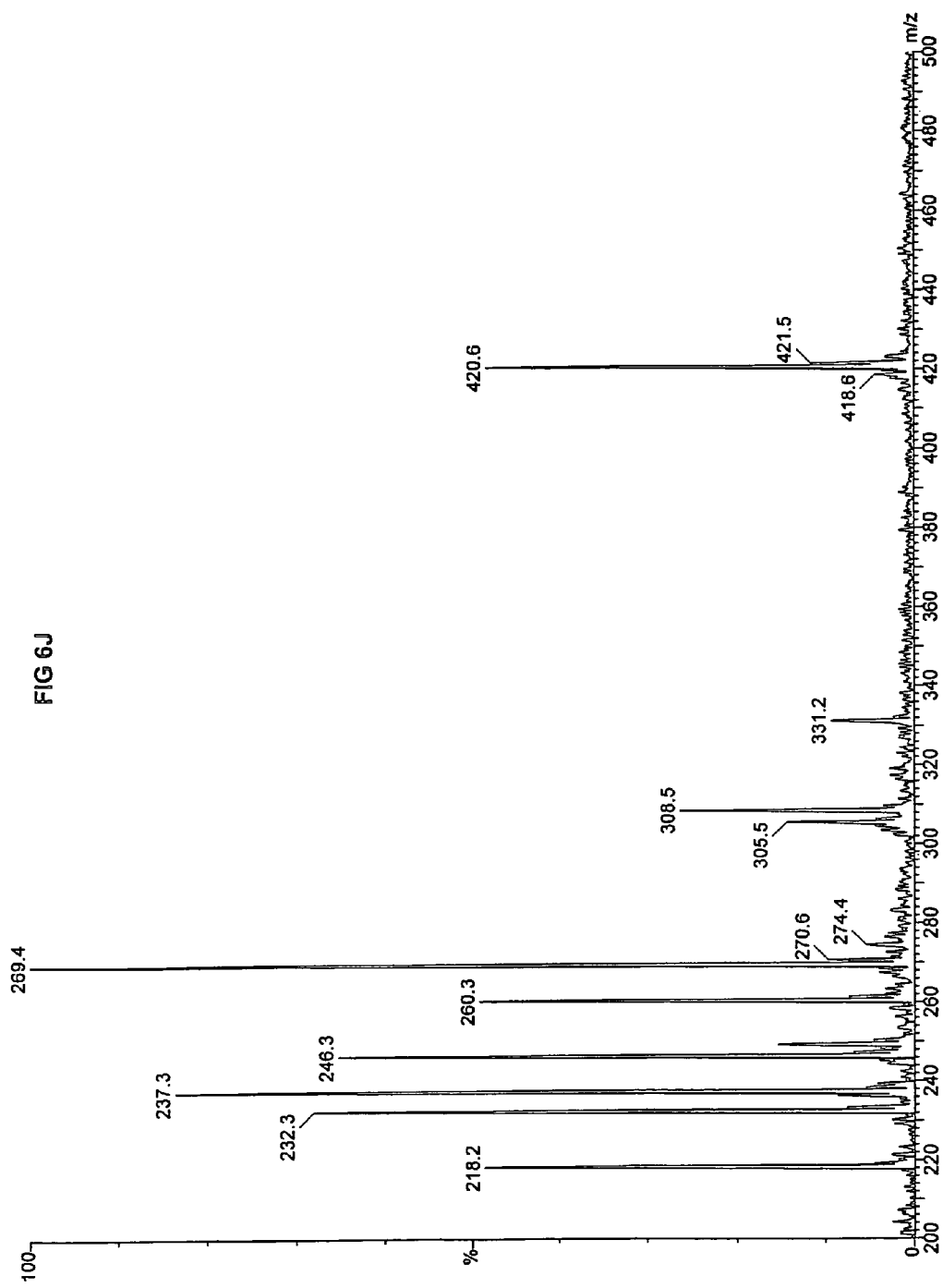
Figure 6K:
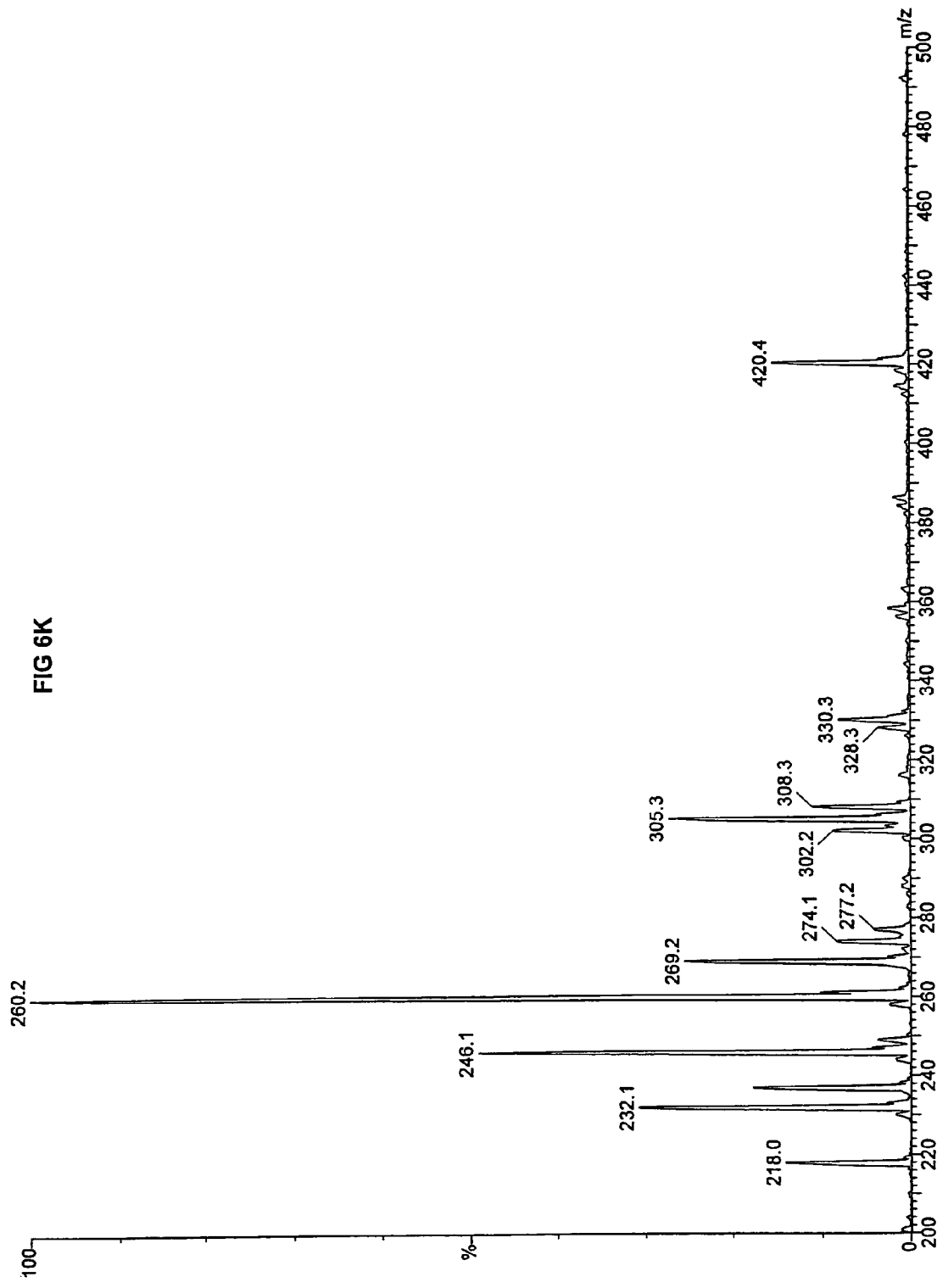
Figure 6L:
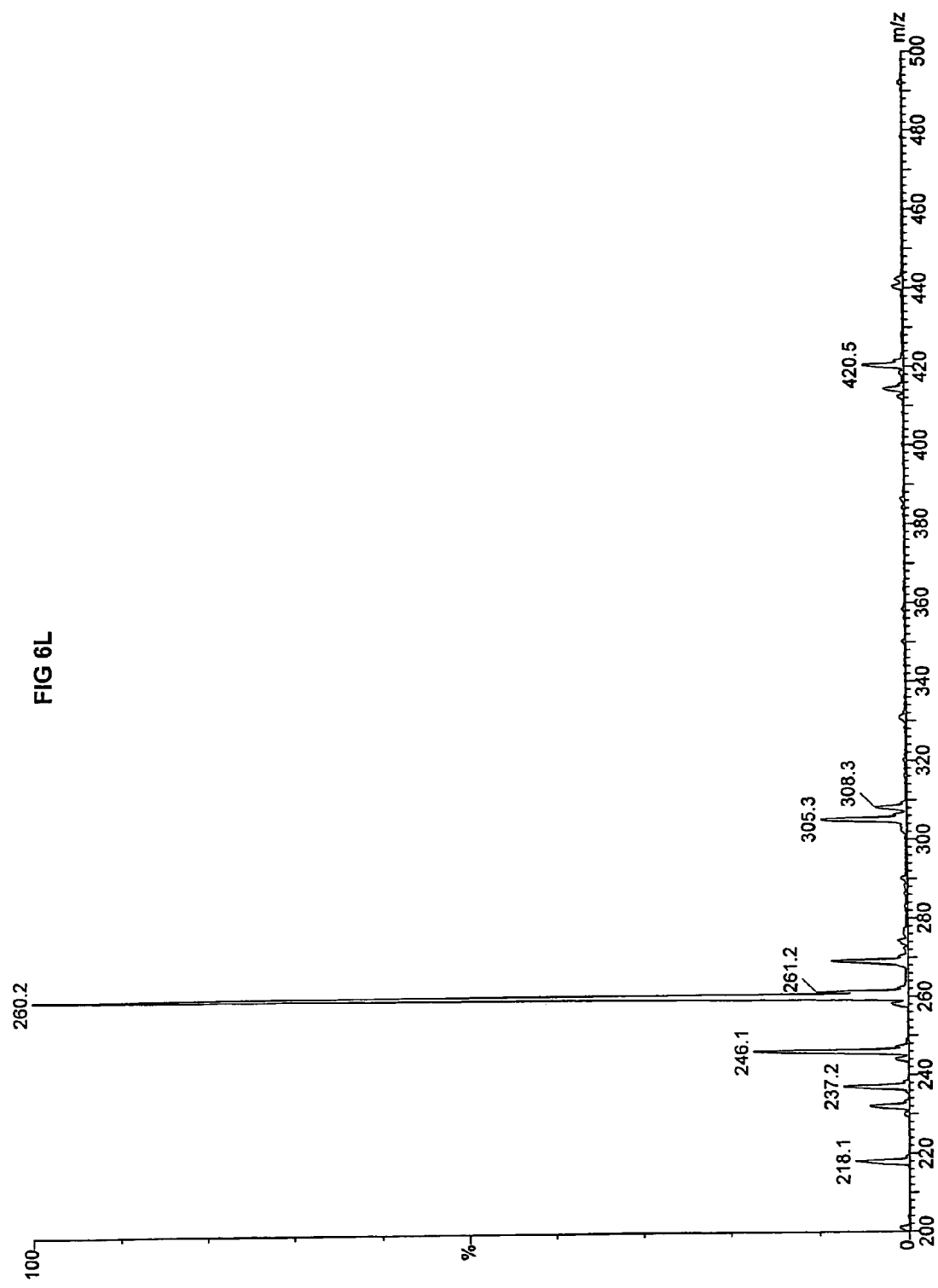

FIG. 6J is a graph depicting a tandem mass spectrometry profile for fibroblasts treated with D3-C8 (8-$^2H_3$-octanoate). The fibroblasts were obtained from a child who suffered from short-chain acyl-CoA dehydrogenase (SCAD) deficiency. Test parameters were: parents of 99FB (fast atom bombardment) and MCA acquisition. Internal standards for the profiles in FIGS. 6J-6L are located at m/z420.4 ($^2H_6$-palmitate-C16), m/z308.1 ($^2H_6$ octanoate-C8), m/z269.2 ($^2H_9$-isovaleric-C5), and m/z237 ($^2H_5$-propionate-C3). The peak at m/z305.0 represents D3-C8 (8-$^2H_3$-octanoate).

FIG. 6K is a graph depicting a tandem mass spectrometry profile for fibroblasts treated with D3-C8 (8-$^2H_3$-octanoate). The fibroblasts were obtained from a child who suffered from electron transfer flavoprotein QO dehydrogenase-mild (ETF-DH mild) deficiency. Test parameters were: parents of 99FB (fast atom bombardment) and MCA acquisition. The peak at m/z305.2 represents D3-C8 (8-$^2$H$_3$-octanoate).

FIG. 6L is a graph depicting a tandem mass spectrometry profile for fibroblasts treated with D3-C8 (8-$^2$H$_3$-octanoate). The fibroblasts were obtained from a child who suffered from electron transfer flavoprotein QO dehydrogenase-severe (ETF-DH severe) deficiency. Test parameters were: parents of 99FB (fast atom bombardment) and MCA acquisition. The peak at m/z305.3 represents D3-C8 (8-$^2$H$_3$-octanoate).

Figure 7A:
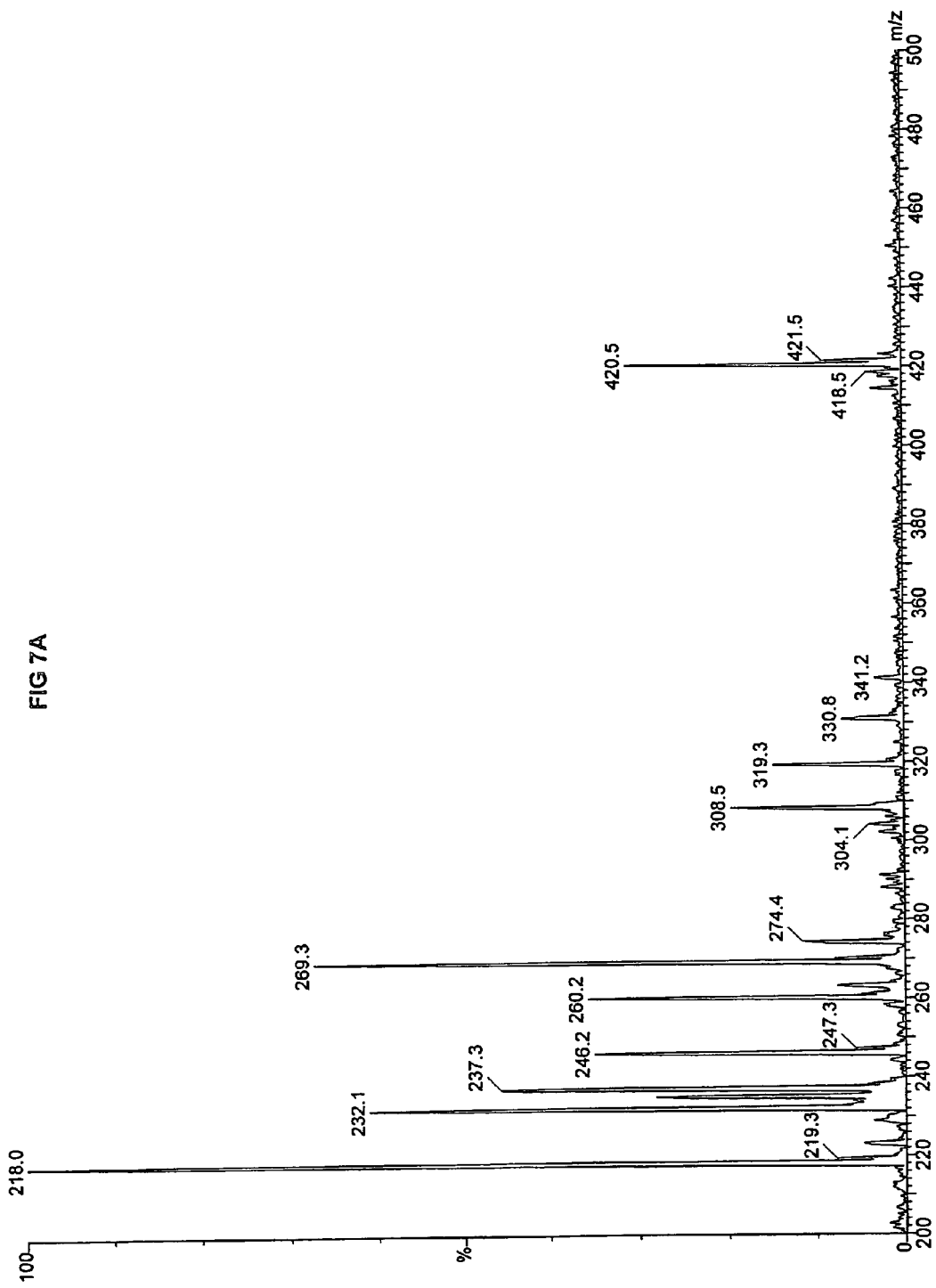
Figure 7B:
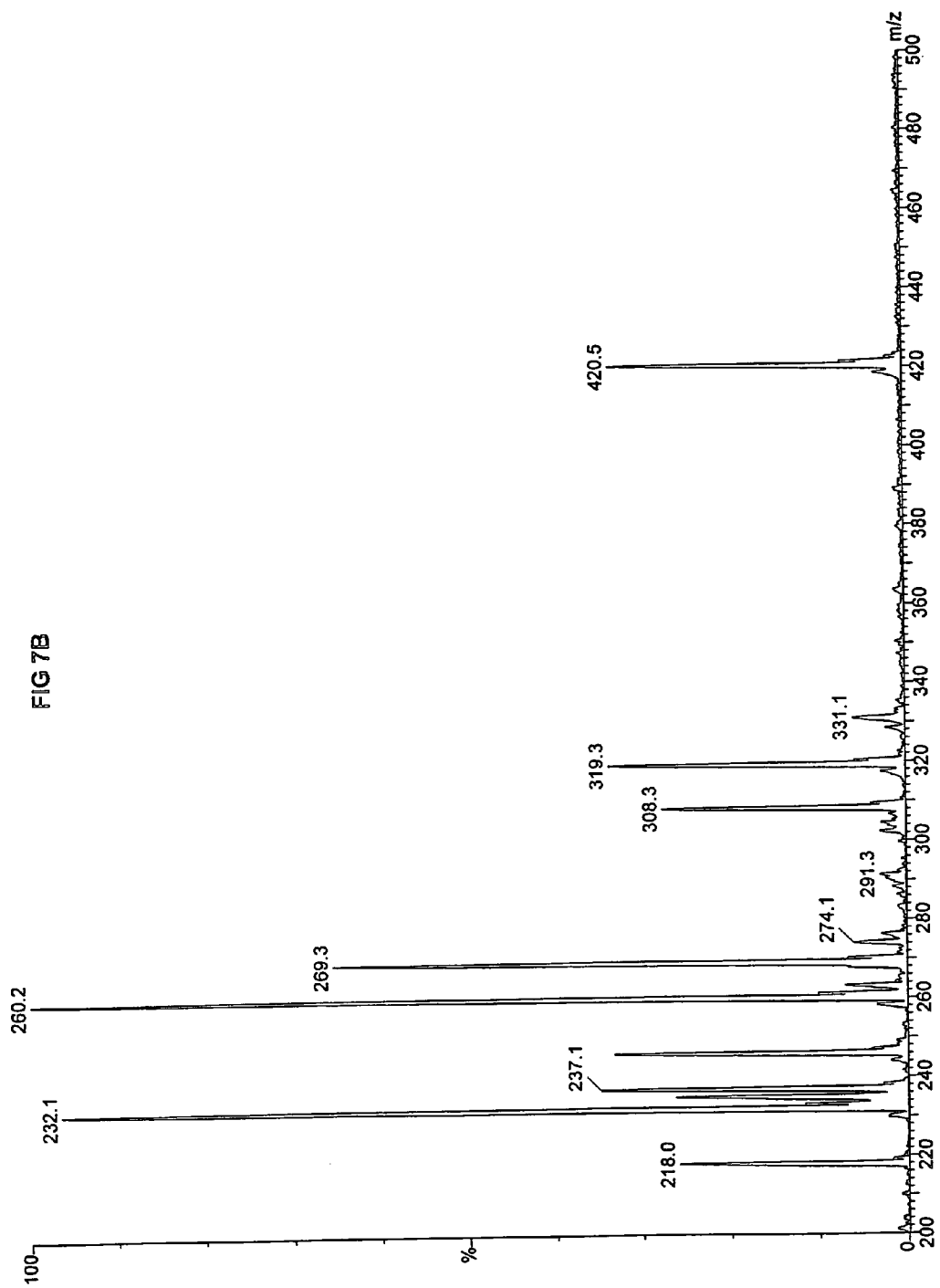

FIG. 7A is a graph depicting a tandem mass spectrometry profile for normal fibroblasts treated with D3-C9 (9-$^2$H$_3$-nonanoate). Test parameters were: parents of 99FB (fast atom bombardment) and MCA acquisition. Internal standards for the profiles in FIGS. 7A-7C are located at m/z420.4 ($^2$H$_6$-palmitate-C16), m/z308.2 ($^2$H$_6$-octanoate-C8), m/z269.2 ($^2$H$_9$-isovaleric-C5), and m/z237.3 ($^2$H$_5$-propionate-C3). The peak at m/z319.3 represents D3-C9 (9-$^2$H$_3$-nonanoate).

FIG. 7B is a graph depicting a tandem mass spectrometry profile for fibroblasts treated with D3-C9 (9-$^2$H$_3$-nonanoate). The fibroblasts were obtained from a child who suffered from carnitine palmitoyltransferase I (CPT I) deficiency. Test parameters were: parents of 99FB (fast atom bombardment) and MCA acquisition. The peak at m/z319.3 represents D3-C9 (9-$^2$H$_3$-nonanoate).

FIG. 7C is a graph depicting a tandem mass spectrometry profile for fibroblasts treated with D3-C9 (9-$^2$H$_3$-nonanoate). The fibroblasts were obtained from a child who suffered from translocase deficiency. Test parameters were: parents of 99FB (fast atom bombardment) and MCA acquisition. The peak at m/z319.3 represents D3-C9 (9-$^2$H$_3$-nonanoate).

Figure 7D:
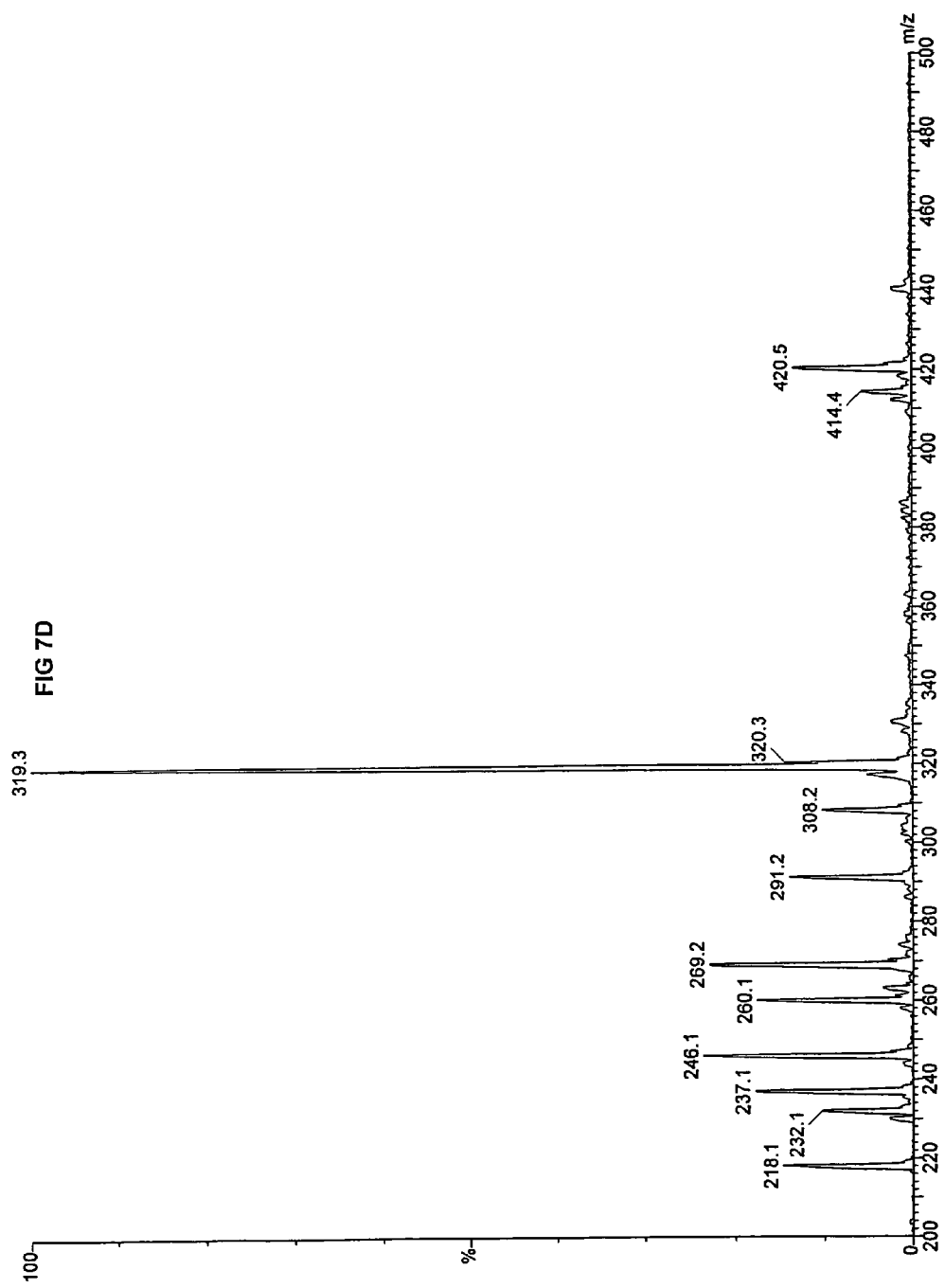
Figure 7E:
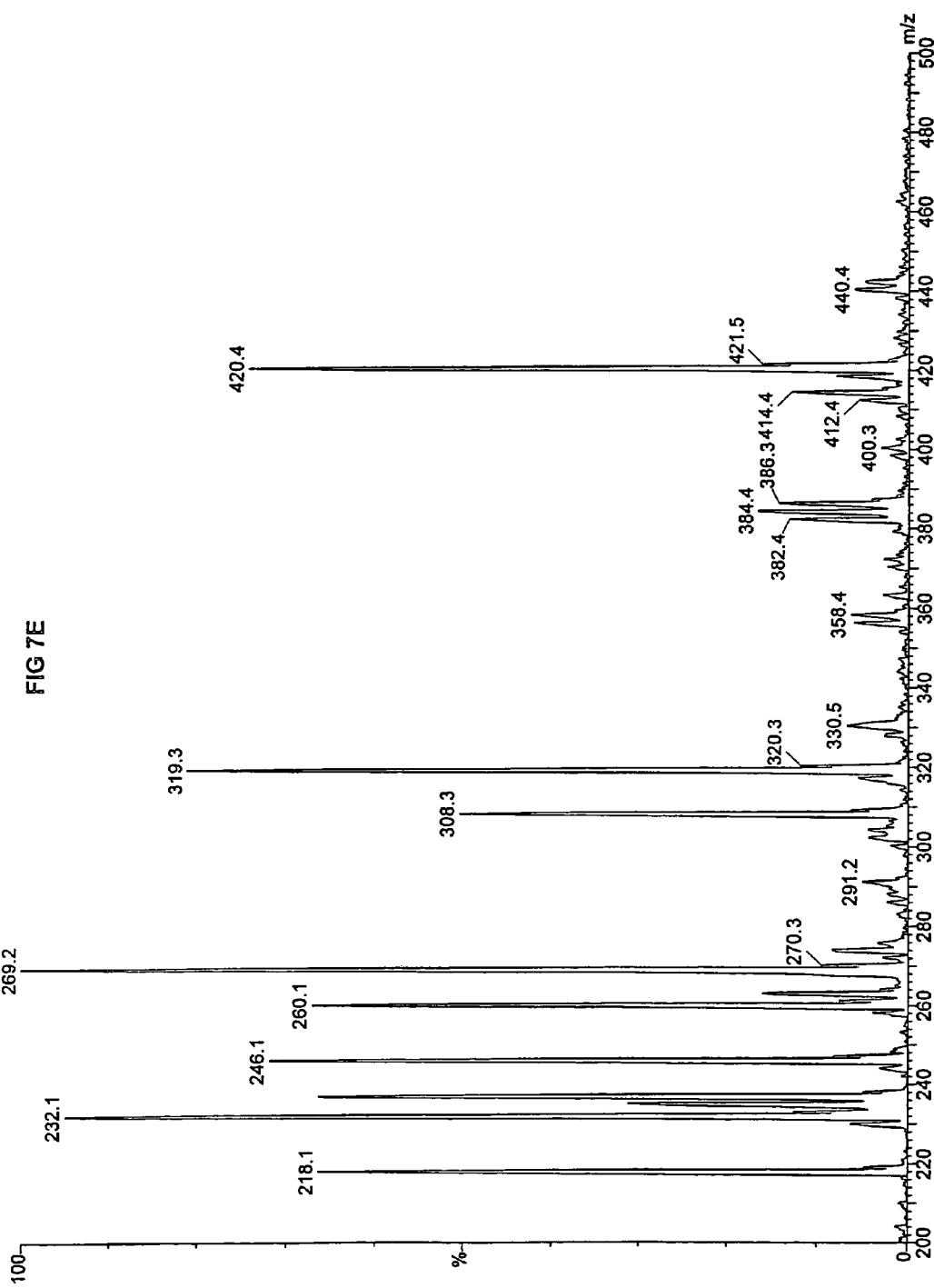
Figure 7F:
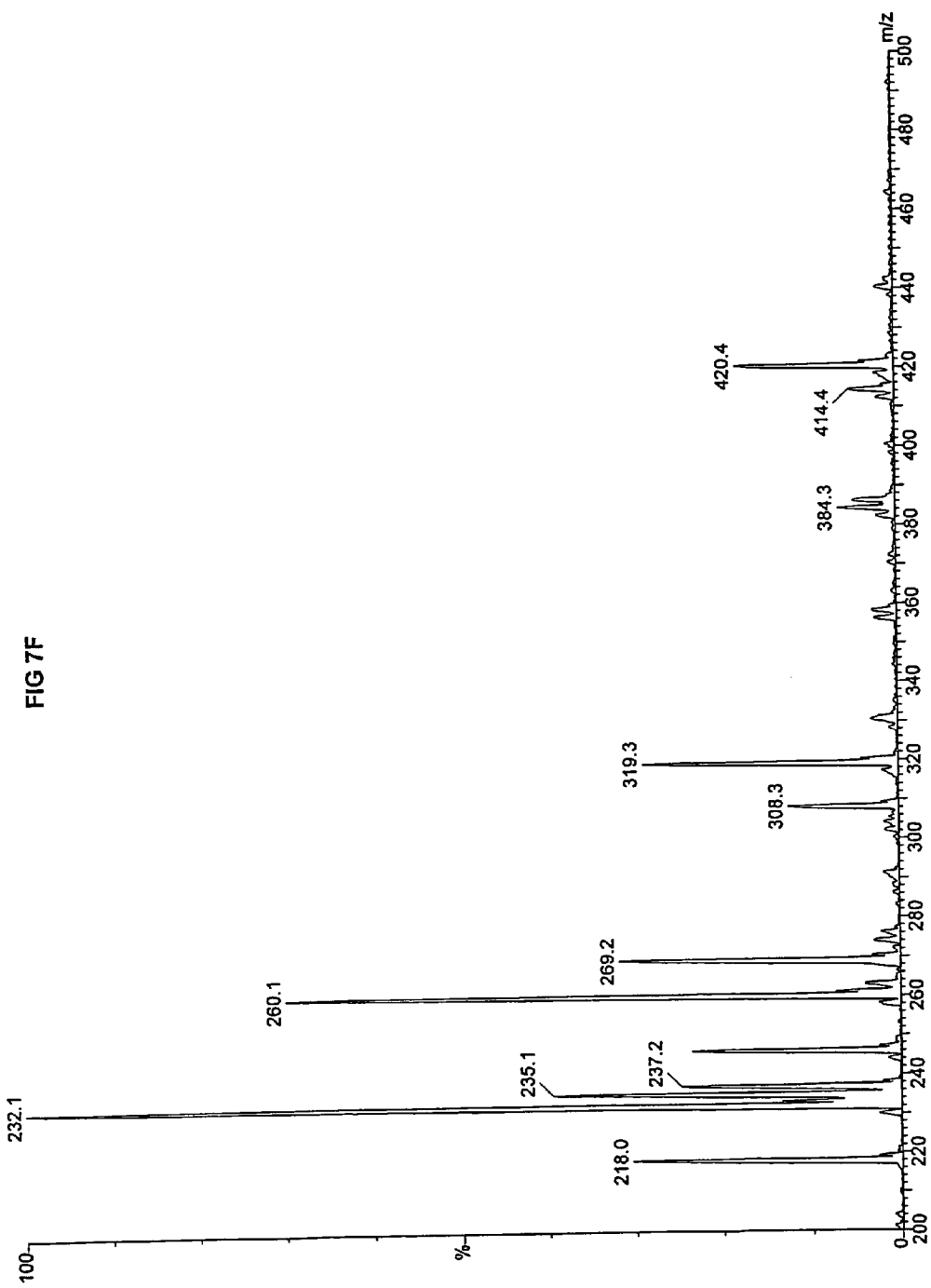

FIG. 7D is a graph depicting a tandem mass spectrometry profile for fibroblasts treated with D3-C9 (9-$^2$H$_3$-nonanoate). The fibroblasts were obtained from a child who suffered from carnitine palmitoyltransferase II (CPT II) deficiency. Test parameters were: parents of 99FB (fast atom bombardment) and MCA acquisition. Internal standards for the profiles in FIGS. 7D-7F are located at m/z420.5 (2H-palmitate-C16), m/z308.3 ($^2$H$_6$-octanoate-C8), m/z269.3 ($^2$H$_9$-isovaleric-C5), and m/z237.1 ($^2$H$_5$-propionate-C3). The peak at m/z319.3 represents D3-C9 (9-$^2$H$_3$-nonanoate).

FIG. 7E is a graph depicting a tandem mass spectrometry profile for fibroblasts treated with D3-C9 (9-$^2$H$_3$-nonanoate). The fibroblasts were obtained from a child who suffered from the "cardiac" form of very-long-chain acyl-CoA dehydrogenase (VLCAD-C) deficiency. Test parameters were: parents of 99FB (fast atom bombardment) and MCA acquisition. The peak at m/z319.3 represents D3-C9 (9-$^2$H$_3$-nonanoate).

FIG. 7F is a graph depicting a tandem mass spectrometry profile for fibroblasts treated with D3-C9 (9-$^2$H$_3$-nonanoate). The fibroblasts were obtained from a child who suffered from the "hypoglycemic" form of very-long-chain acyl-CoA dehydrogenase (VLCAD-H) deficiency. Test parameters were: parents of 99FB (fast atom bombardment) and MCA acquisition. The peak at m/z319.3 represents D3-C9 (9-$^2$H$_3$-nonanoate).

Figure 7G:
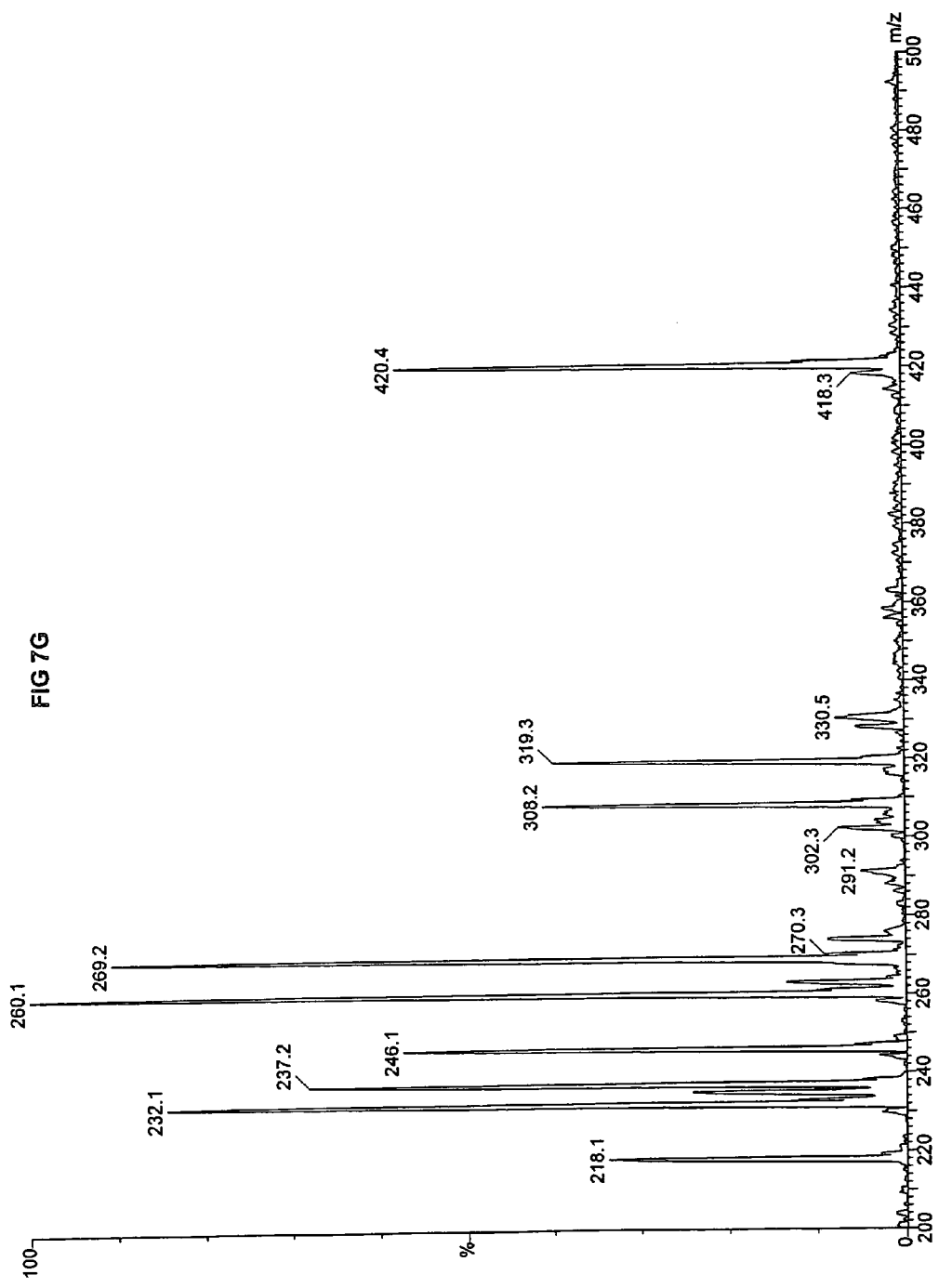

FIG. 7G is a graph depicting a tandem mass spectrometry profile for fibroblasts treated with D3-C9 (9-$^2$H$_3$-nonanoate). The fibroblasts were obtained from a child who suffered from mitchondrial trifunctional protein (TRIFUNCTIONAL) deficiency. Test parameters were: parents of 99FB (fast atom bombardment) and MCA acquisition. Internal standards for the profiles in FIGS. 7G-71 are located at m/z420.5 ($^2$H$_6$-palmitate-C16), m/z308.2 ($^2$H$_6$-octanoate-C8), m/z269.3 ($^2$H$_9$-isovaleric-C5), and m/z237.2 ($^2$H$_5$-propionate-C3). The peak at m/z319.3 represents D3-C9 (9-$^2$H$_3$-nonanoate).

Figure 7H:
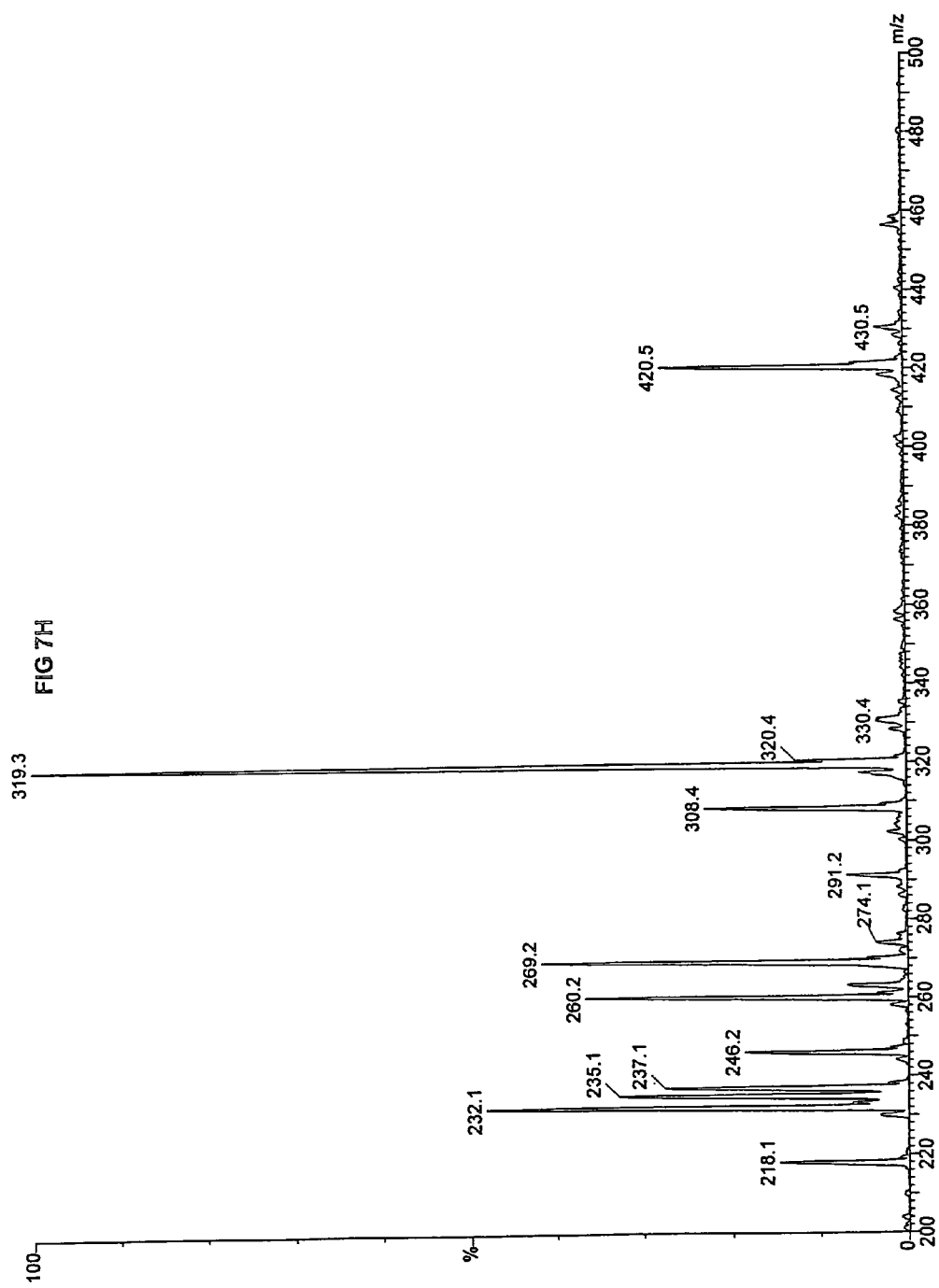

FIG. 7H is a graph depicting a tandem mass spectrometry profile for fibroblasts treated with D3-C9 (9-$^2$H$_3$-nonanoate). The fibroblasts were obtained from a child who suffered from long-chain L-3-hydroxy-acyl-CoA dehydrogenase (LCHAD) deficiency. Test parameters were: parents of 99FB (fast atom bombardment) and MCA acquisition. The peak at m/z319.2 represents D3-C9 (9-$^2$H$_3$-nonanoate).

Figure 7I:
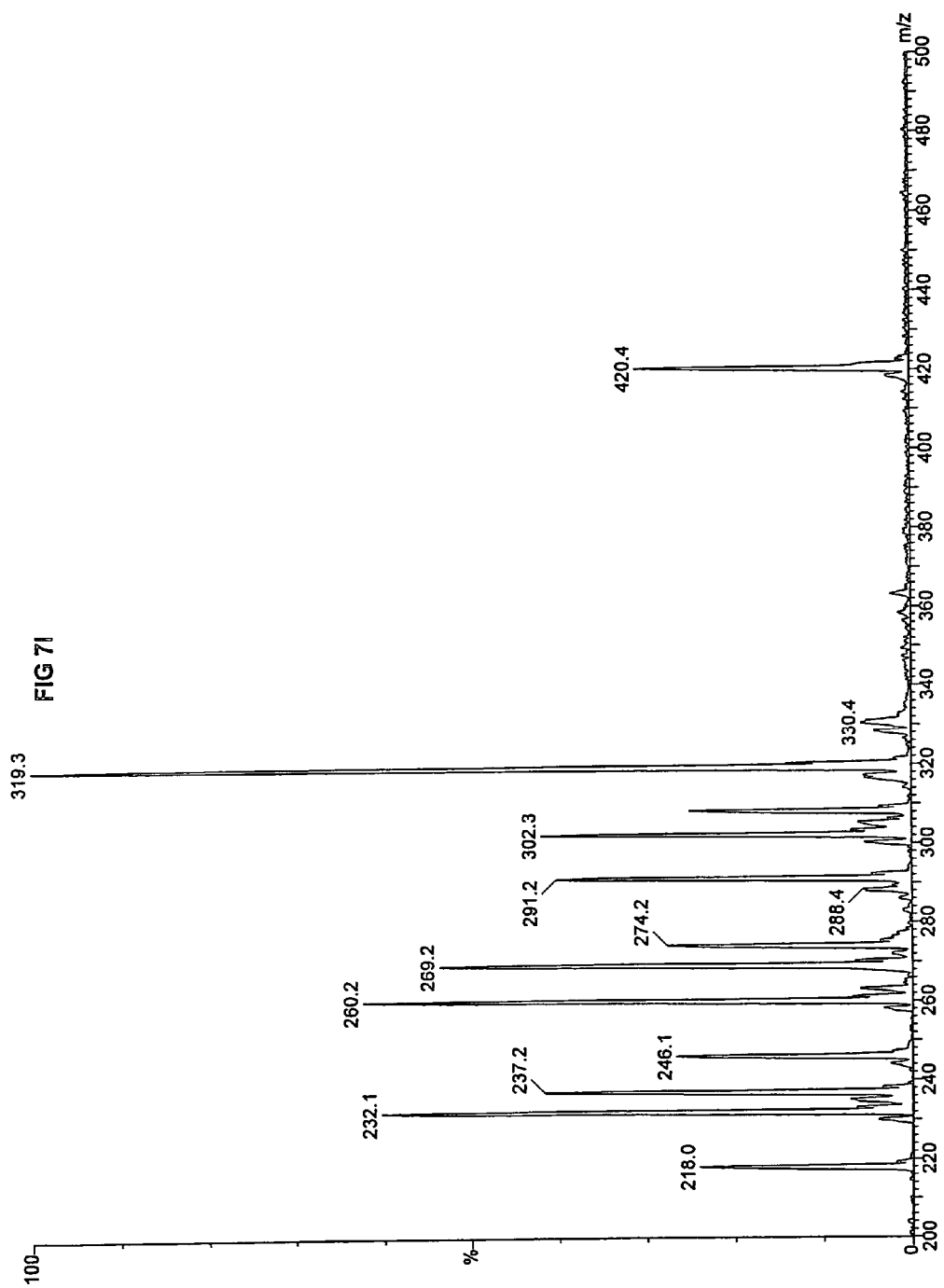

FIG. 7I is a graph depicting a tandem mass spectrometry profile for fibroblasts treated with D3-C9 (9-$^2$H$_3$-nonanoate). The fibroblasts were obtained from a child who suffered from medium-chain acyl-CoA dehydrogenase (MCAD) deficiency. Test parameters were: parents of 99FB (fast atom bombardment) and MCA acquisition. The peak at m/z319.0 represents D3-C9 (9-$^2$H$_3$-nonanoate).

Figure 7J:
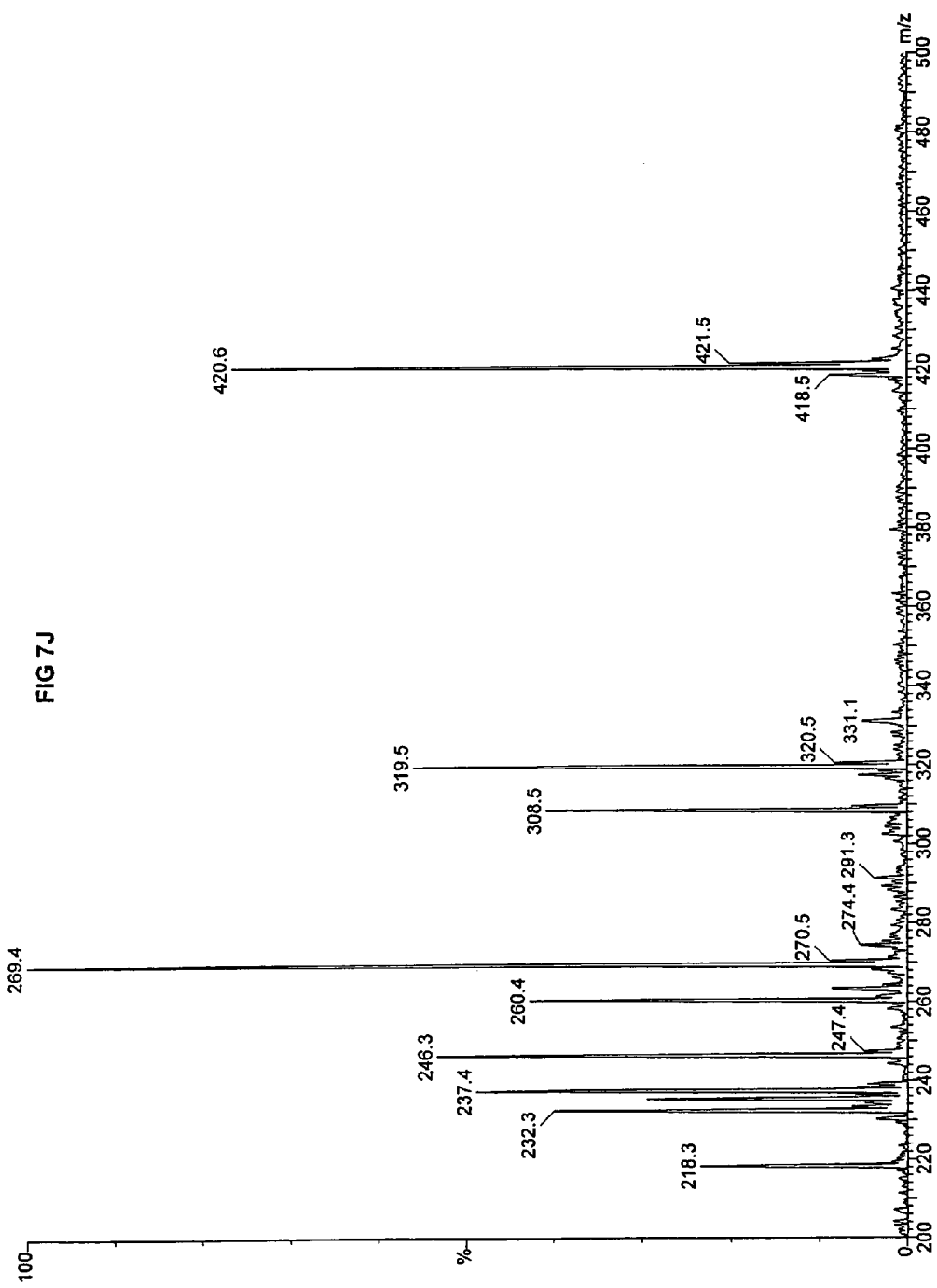
Figure 7K:
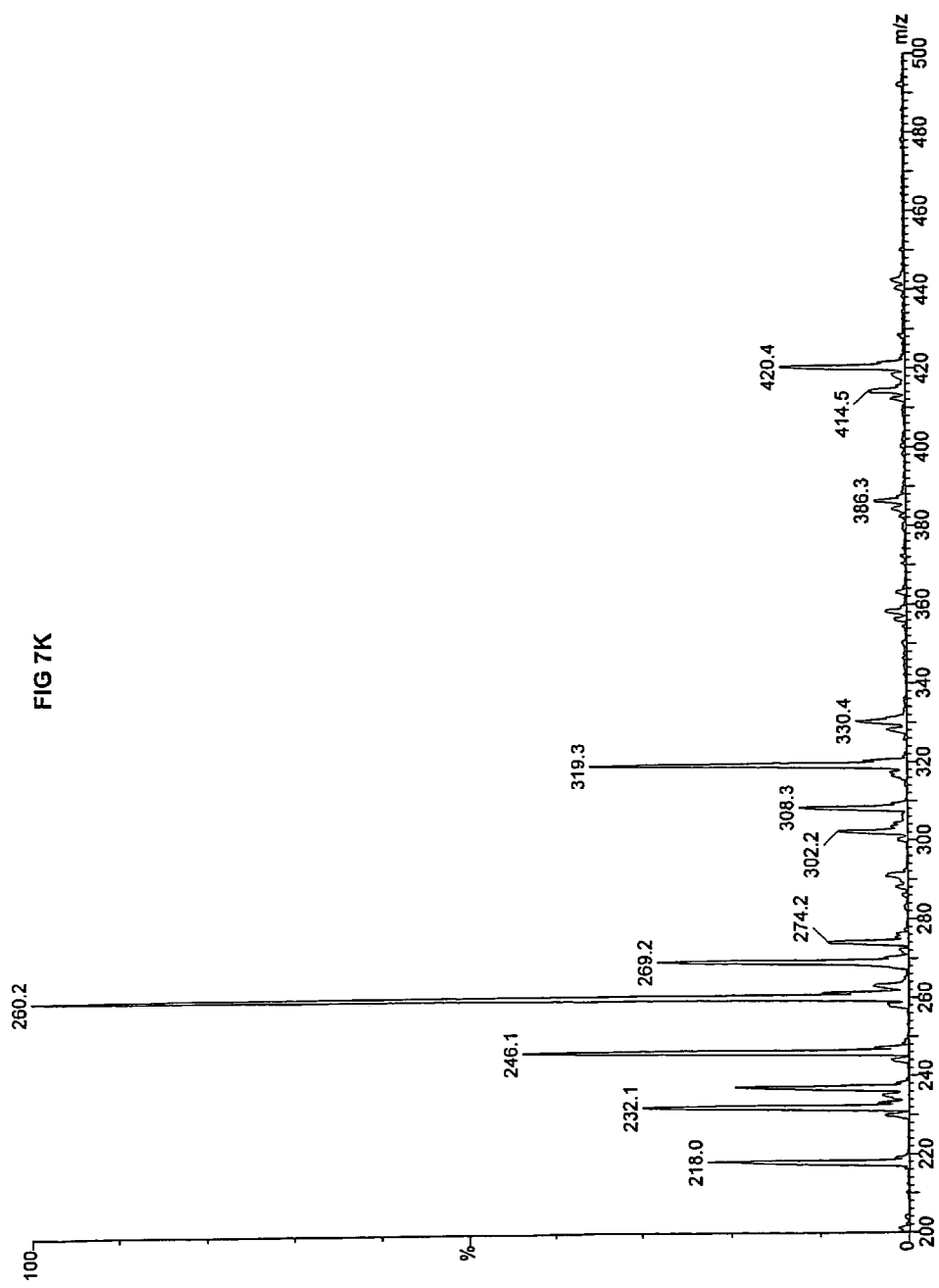
Figure 7L:
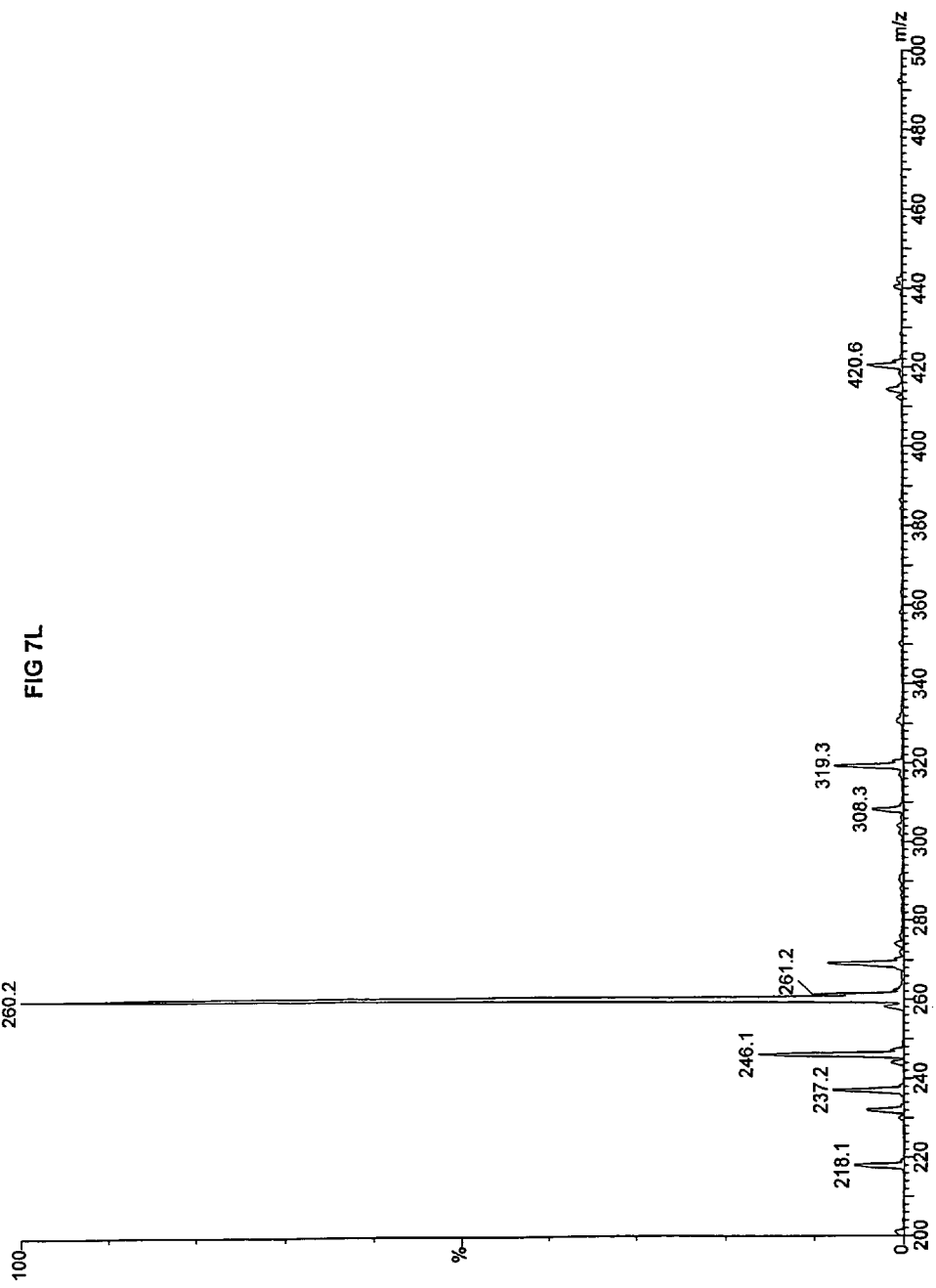

FIG. 7J is a graph depicting a tandem mass spectrometry profile for fibroblasts treated with D3-C9 (9-$^2$H$_3$-nonanoate). The fibroblasts were obtained from a child who suffered from short-chain acyl-CoA dehydrogenase (SCAD) deficiency. Test parameters were: parents of 99FB (fast atom bombardment) and MCA acquisition. Internal standards for the profiles in FIGS. 7J-7L are located at m/z420.4 ($^2$H$_6$-palmitate-C16), m/z308.2 ($^2$H$_6$-octanoate-C8), m/z269.3 ($^2$H$_9$-isovaleric-C5), and m/z237.0 ($^2$H$_5$-propionate-C3). The peak at m/z319.3 represents D3-C9 (9-$^2$H$_3$-nonanoate).

FIG. 7K is a graph depicting a tandem mass spectrometry profile for fibroblasts treated with D3-C9 (9-$^2$H$_3$-nonanoate). The fibroblasts were obtained from a child who suffered from electron transfer flavoprotein QO dehydrogenase-mild (ETF-DH mild) deficiency. Test parameters were: parents of 99FB (fast atom bombardment) and MCA acquisition. The peak at m/z319.3 represents D3-C9 (9-$^2$H$_3$-nonanoate).

FIG. 7L is a graph depicting a tandem mass spectrometry profile for fibroblasts treated with D3-C9 (9-$^2$H$_3$-nonanoate). The fibroblasts were obtained from a child who suffered from electron transfer flavoprotein QO dehydrogenase-severe (ETF-DH severe) deficiency. Test parameters were: parents of 99FB (fast atom bombardment) and MCA acquisition. The peak at m/z319.3 represents D3-C9 (9-$^2$H$_3$-nonanoate).

Figure 8A:
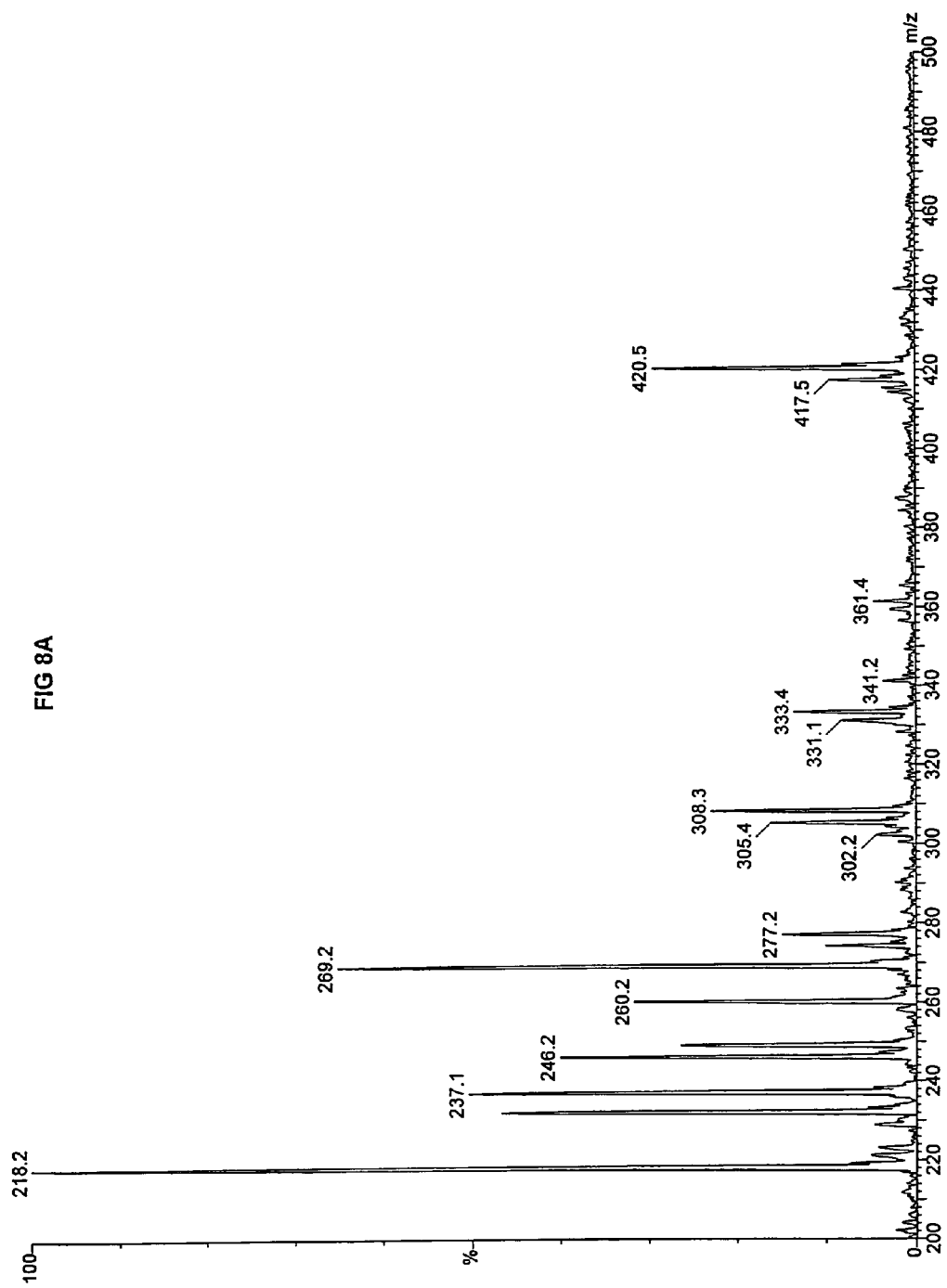
Figure 8B:
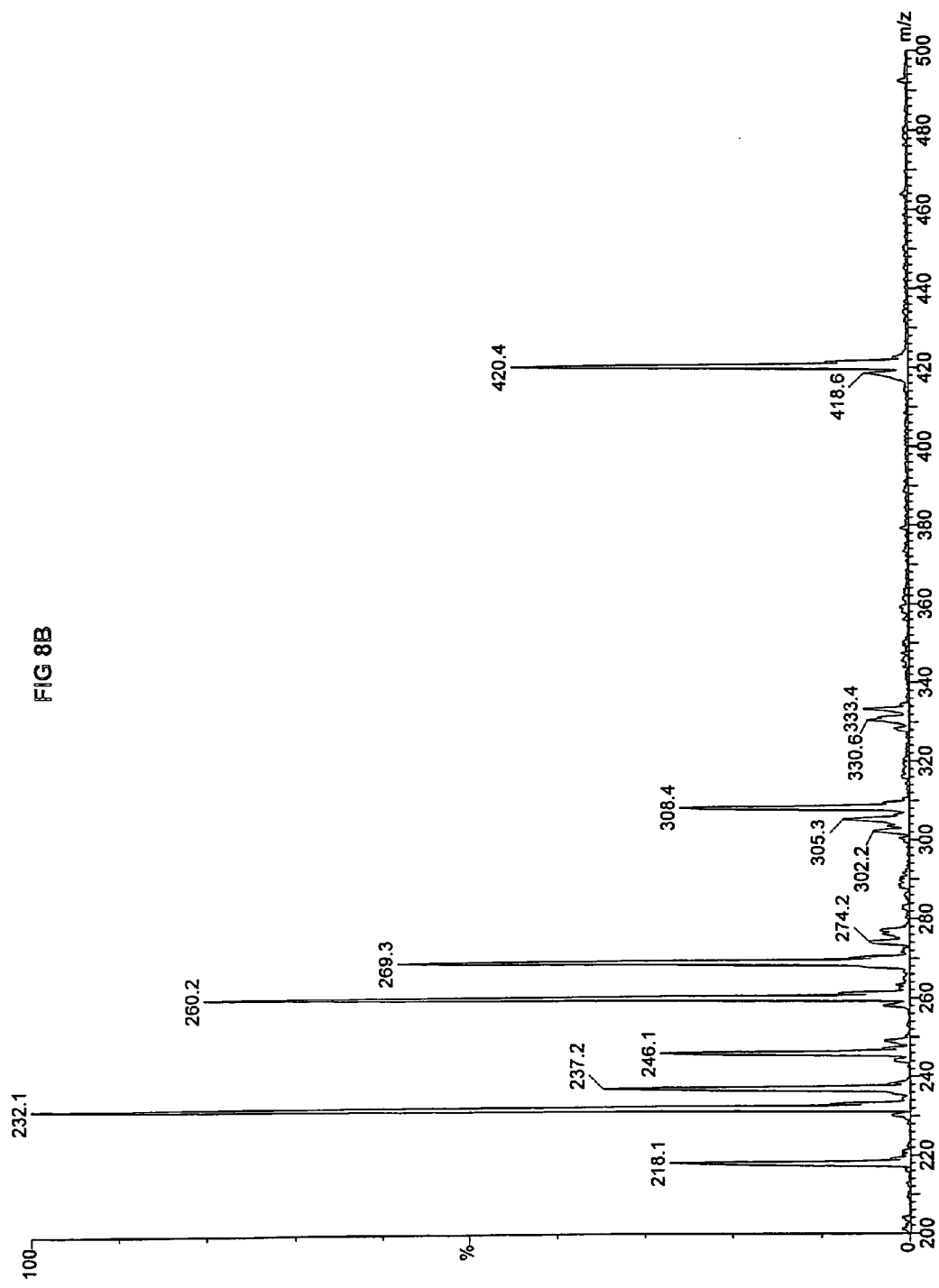
Figure 8C:
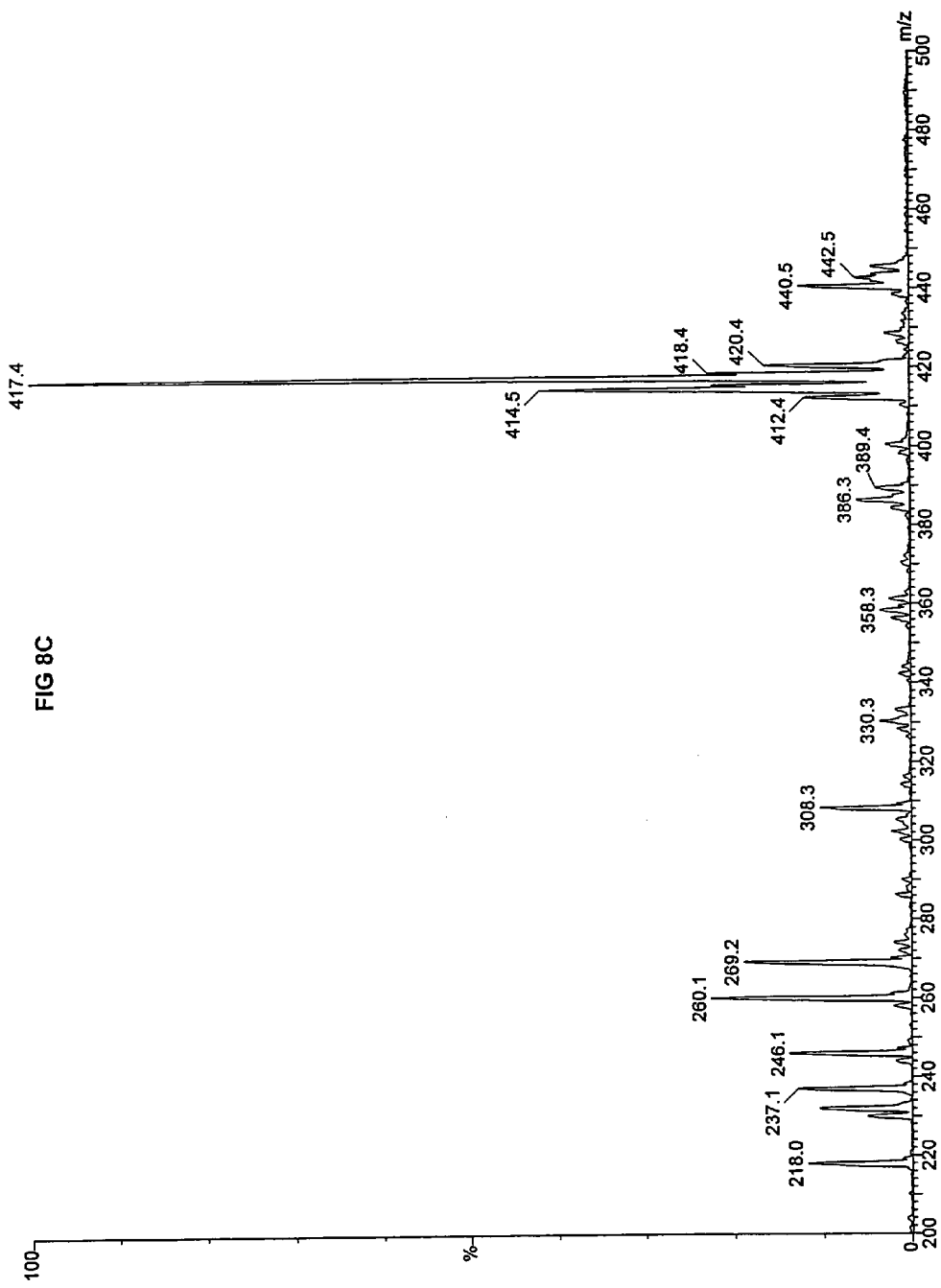

FIG. 8A is a graph depicting a tandem mass spectrometry profile for normal fibroblasts treated with D3-C16 (16-$^2$H$_3$-palmitate). Test parameters were: parents of 99FB (fast atom bombardment) and MCA acquisition. Internal standards for the profiles in FIGS. 8A-8C are located at m/z420.4 ($^2$H$_6$-palmitate-C16), m/z308.2 ($^2$H$_6$-octanoate-C8), m/z269.2 ($^2$H$_9$-isovaleric-C5), and m/z237.1 ($^2$H$_5$-propionate-C3). The peak at m/z417.0 represents D3-C16 (16-$^2$H$_3$-palmitate).

FIG. 8B is a graph depicting a tandem mass spectrometry profile for fibroblasts treated with D3-C16 (16-$^2$H$_3$-palmitate). The fibroblasts were obtained from a child who suffered from carnitine palmitoyltransferase I (CPT I) deficiency. Test parameters were: parents of 99FB (fast atom bombardment) and MCA acquisition. The peak at m/z417.6 represents D3-C16 (16-$^2$H$_3$-palmitate).

FIG. 8C is a graph depicting a tandem mass spectrometry profile for fibroblasts treated with D3-C16 (16-$^2$H$_3$-palmitate). The fibroblasts were obtained from a child who suffered from translocase deficiency. Test parameters were: parents of 99FB (fast atom bombardment) and MCA acquisition. The peak at m/z417.4 represents D3-C16 (16-$^2$H$_3$-palmitate).

Figure 8D:
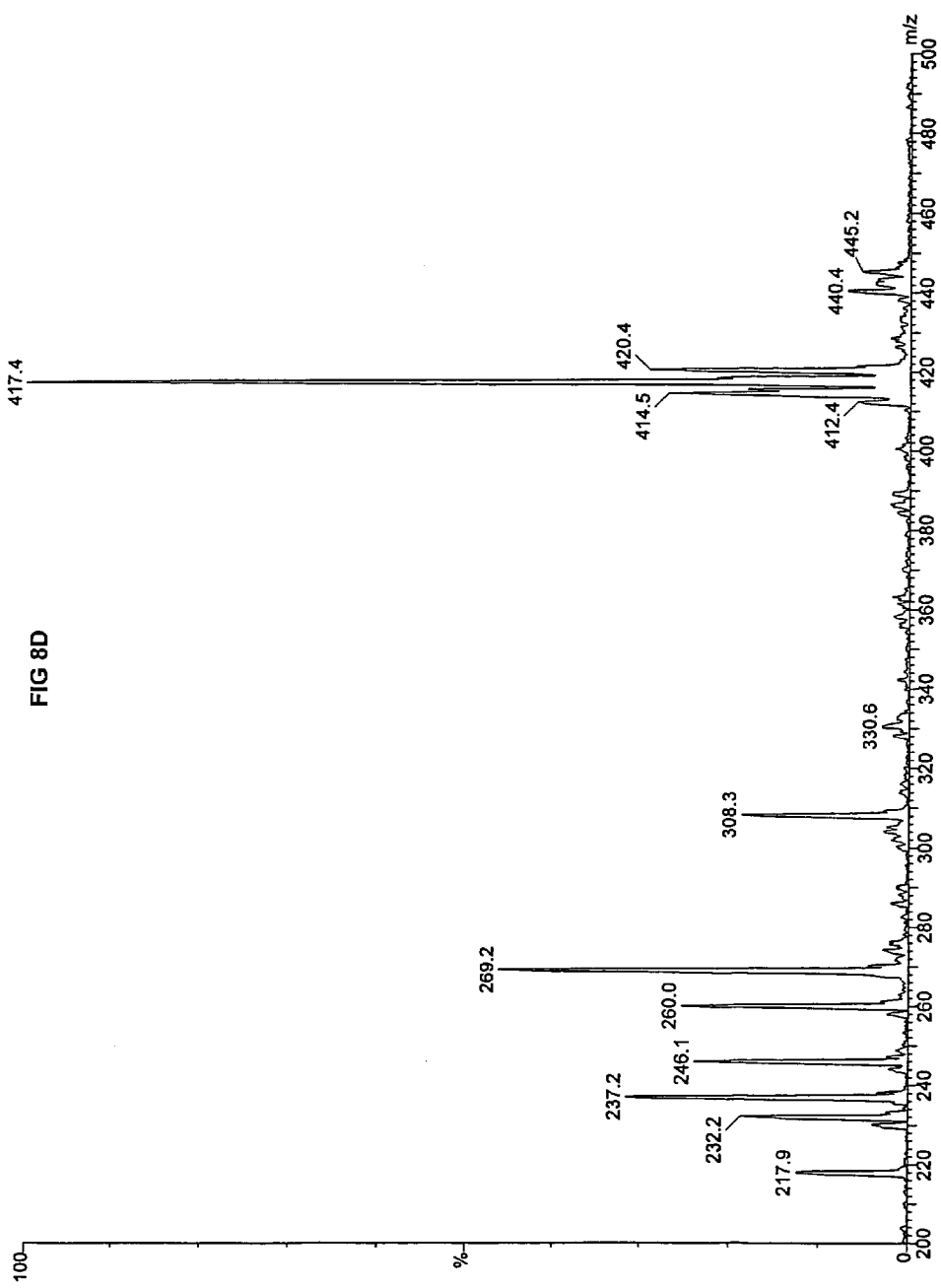
Figure 8E:
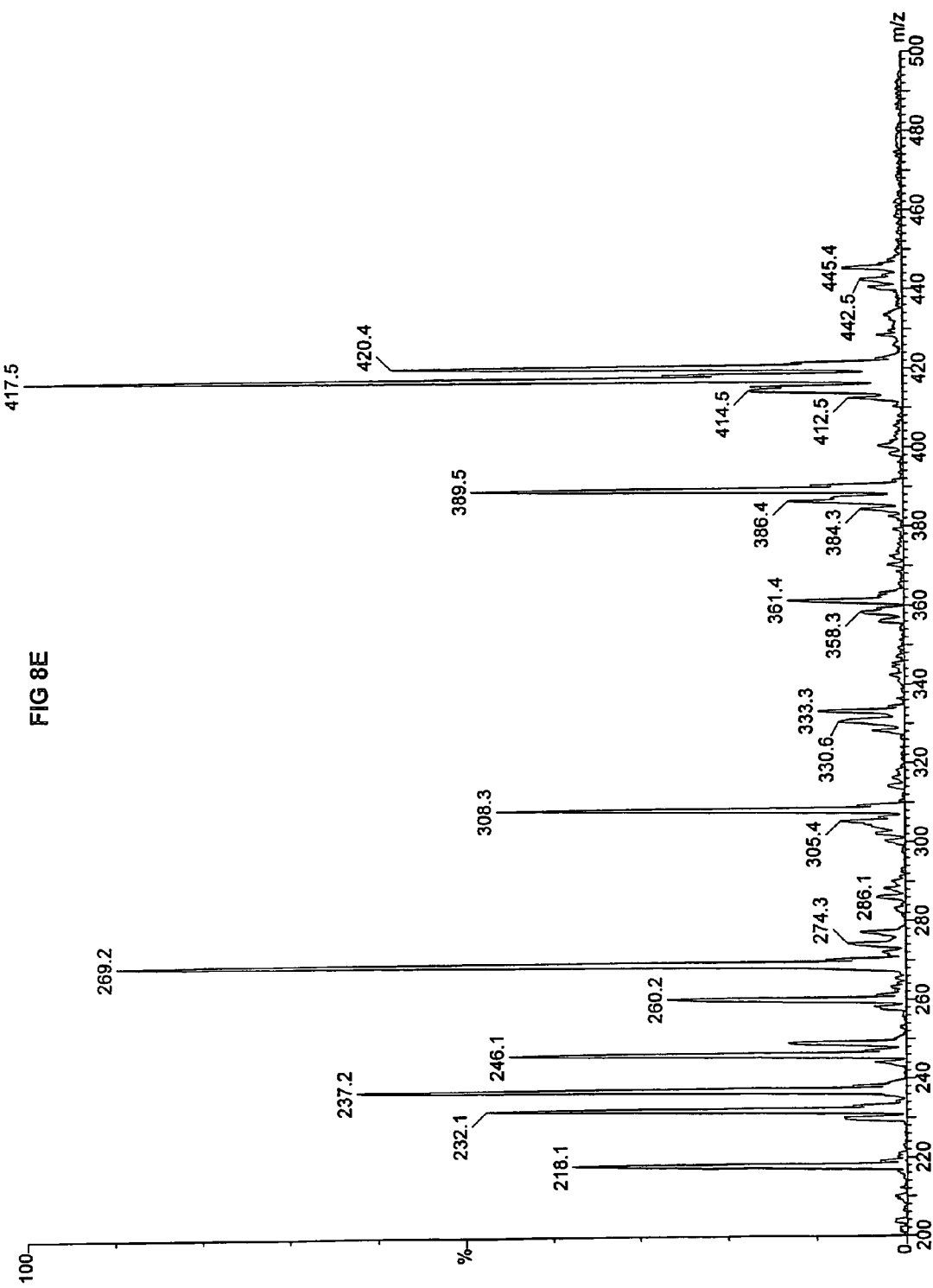
Figure 8F:
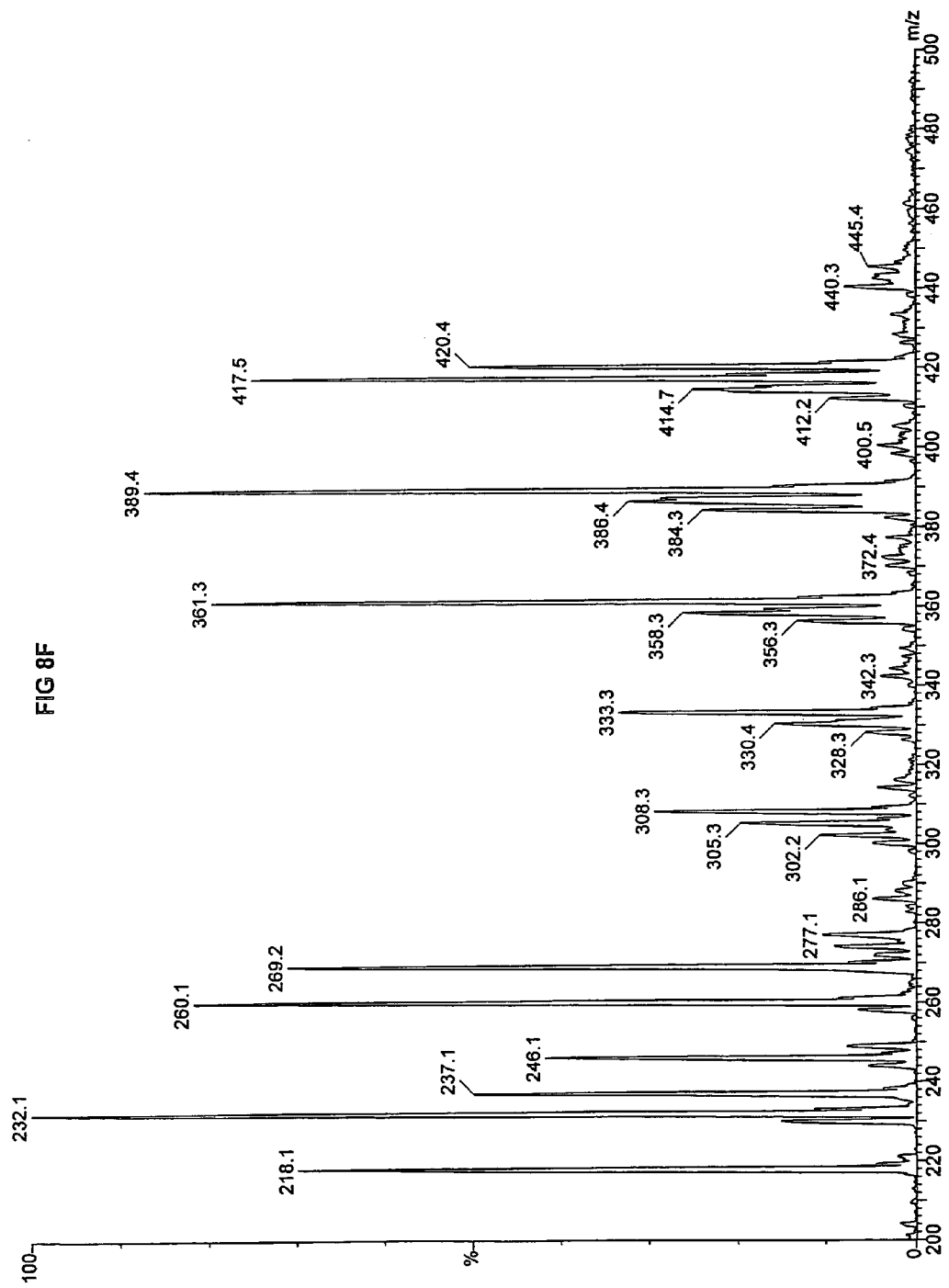

FIG. 8D is a graph depicting a tandem mass spectrometry profile for fibroblasts treated with D3-C16 (16-$^2$H$_3$-palmitate). The fibroblasts were obtained from a child who suffered from carnitine palmitoyltransferase II (CPT II) deficiency. Test parameters were: parents of 99FB (fast atom bombardment) and MCA acquisition. Internal standards for the profiles in FIGS. 8D-8F are located at m/z420.4 ($^2$H$_6$-palmitate-C16), m/z308.2 ($^2$H$_6$-octanoate-C8), m/z269.2 ($^2$H$_9$-isovaleric-C5), and m/z237.2 ($^2$H$_5$-propionate-C3). The peak at m/z417.4 represents D3-C16 (16-$^2$H$_3$-palmitate).

FIG. 8E is a graph depicting a tandem mass spectrometry profile for fibroblasts treated with D3-C 16 (16-$^2$H$_3$-palmitate). The fibroblasts were obtained from a child who suffered from the "cardiac" form of very-long-chain acyl-CoA dehydrogenase (VLCAD-C) deficiency. Test parameters were: parents of 99FB (fast atom bombardment) and MCA acquisition. The peak at m/z417.5 represents D3-C16 (16-$^2$H$_3$-palmitate).

FIG. 8F is a graph depicting a tandem mass spectrometry profile for fibroblasts treated with D3-C16 (16-$^2$H$_3$-palmitate). The fibroblasts were obtained from a child who suffered from the "hypoglycemic" form of very-long-chain acyl-CoA dehydrogenase (VLCAD-H) deficiency. Test parameters were: parents of 99FB (fast atom bombardment) and MCA acquisition. The peak at m/z417.5 represents D3-C1 (16-$^2$H$_3$-palmitate).

Figure 8G:
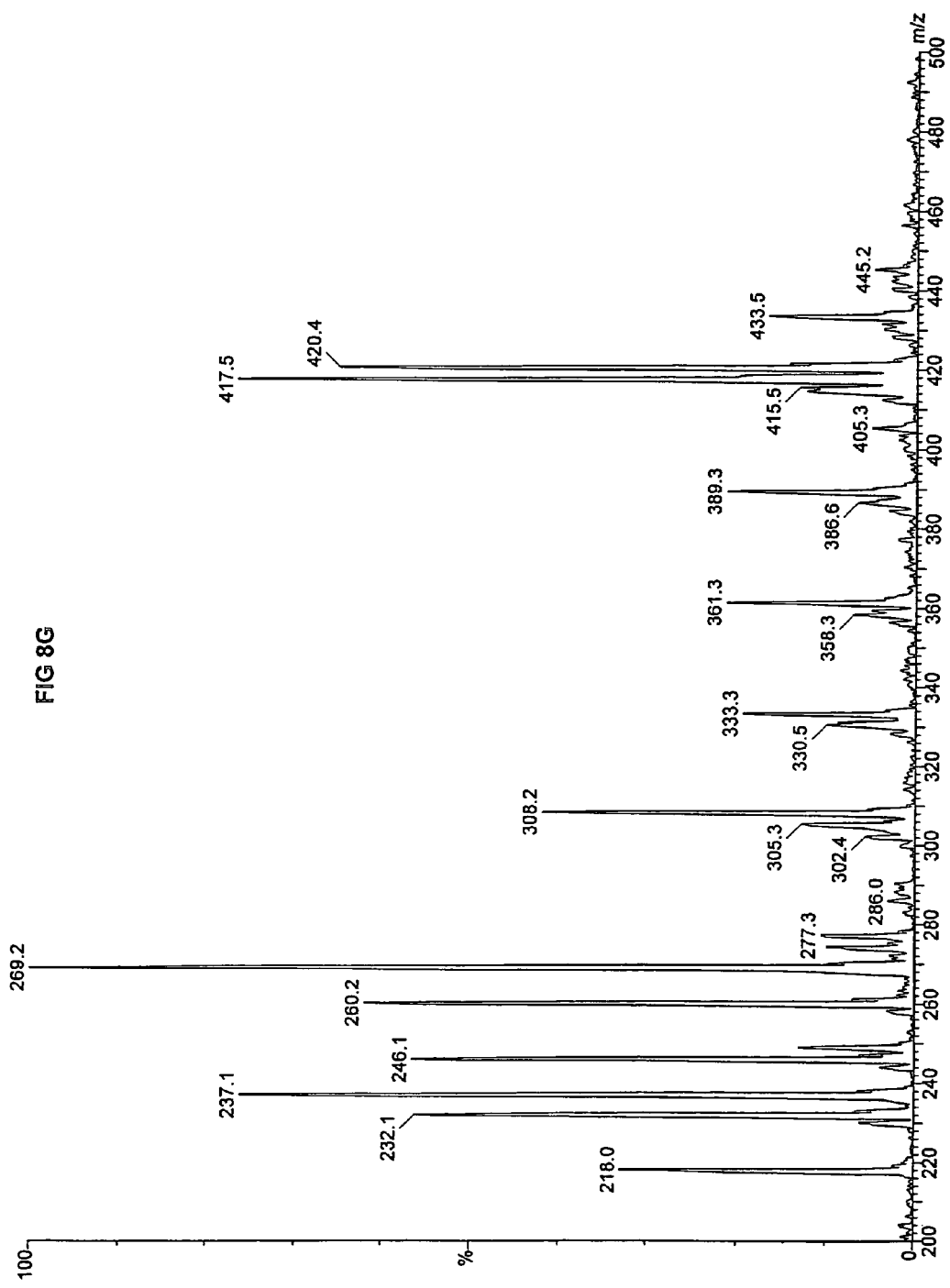
Figure 8H:
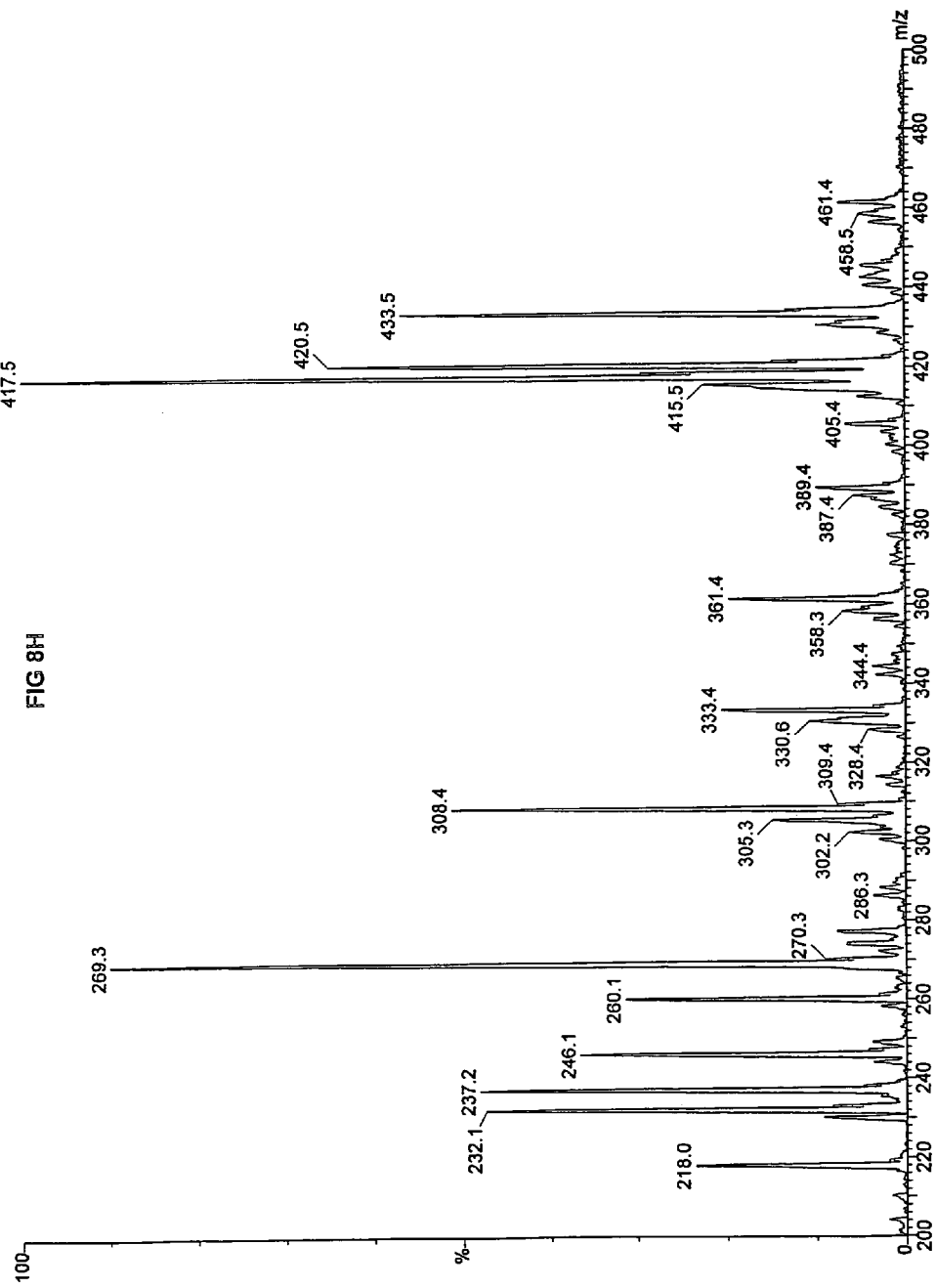
Figure 8I:
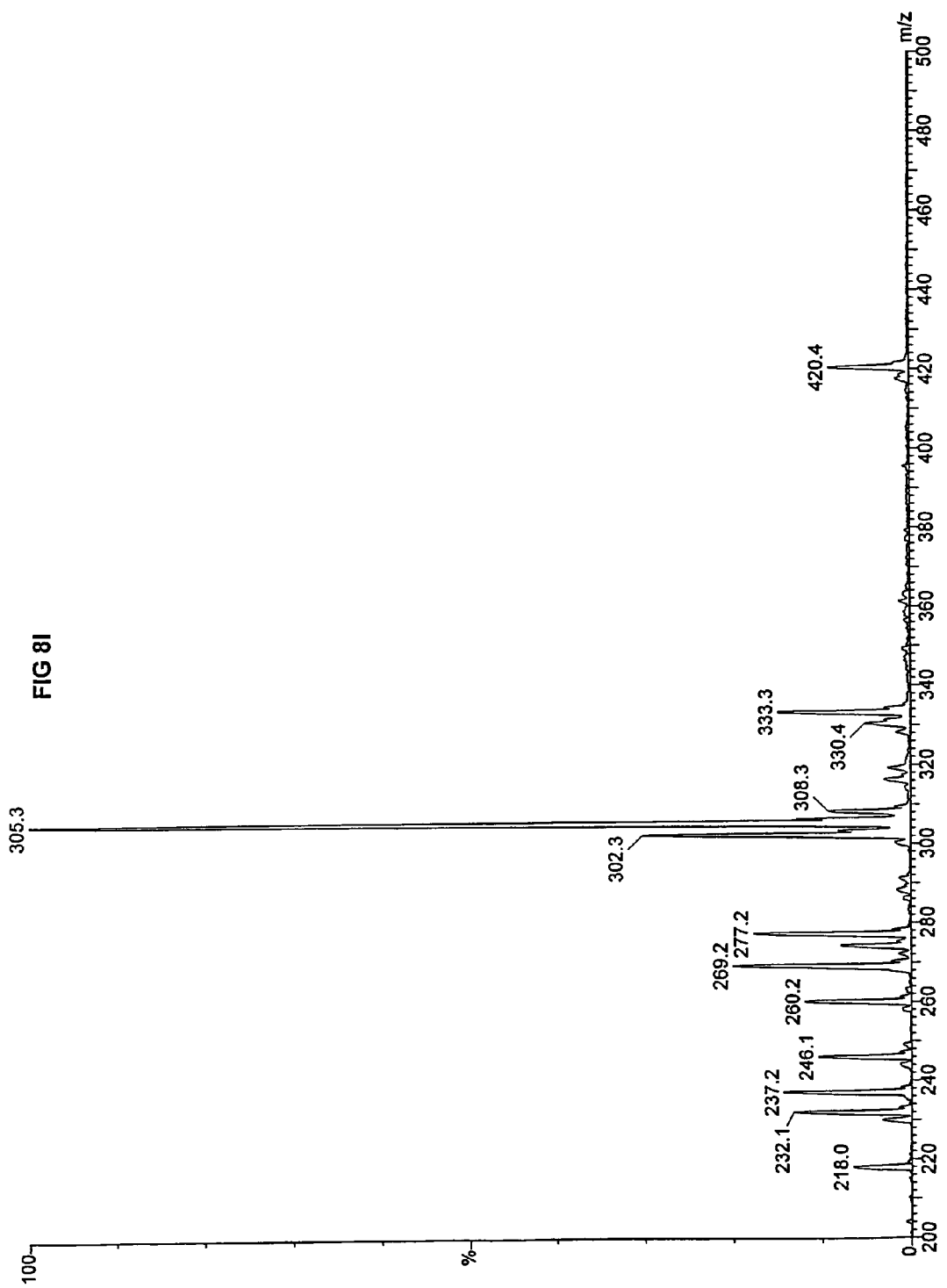

FIG. 8G is a graph depicting a tandem mass spectrometry profile for fibroblasts treated with D3-C16 (16-$^2$H$_3$-palmitate). The fibroblasts were obtained from a child who suffered from mitochondrial trifunctional protein (TRIFUNCTIONAL) deficiency. Test parameters were: parents of 99FB (fast atom bombardment) and MCA acquisition. Internal standards for the profiles in FIGS. 8G-8I are located at m/z420.5 ($^2$H$_6$-palmitate-C16), m/z308.3 ($^2$H$_6$-octanoate-C8), m/z269.2 ($^2$H$_9$-isovaleric-C5), and m/z237.0 ($^2$H$_5$-propionate-C3). The peak at m/z417.4 represents D3-C16 (16-$^2$H$_3$-palmitate).

FIG. 8H is a graph depicting a tandem mass spectrometry profile for fibroblasts treated with D3-C16 (16-$^2$H$_3$-palmitate). The fibroblasts were obtained from a child who suffered from long-chain L-3-hydroxy-acyl-CoA dehydrogenase (LCHAD) deficiency. Test parameters were: parents of 99FB (fast atom bombardment) and MCA acquisition. The peak at m/z417.4 represents D3-C16 (16-$^2$H$_3$-palmitate).

FIG. 8I is a graph depicting a tandem mass spectrometry profile for fibroblasts treated with D3-C16 (16-$^2$H$_3$-palmitate). The fibroblasts were obtained from a child who suffered from medium-chain acyl-CoA dehydrogenase (MCAD) deficiency. Test parameters were: parents of 99FB (fast atom bombardment) and MCA acquisition. The peak at m/z417 represents D3-C16 (16-$^2$H$_3$-palmitate).

Figure 8J:
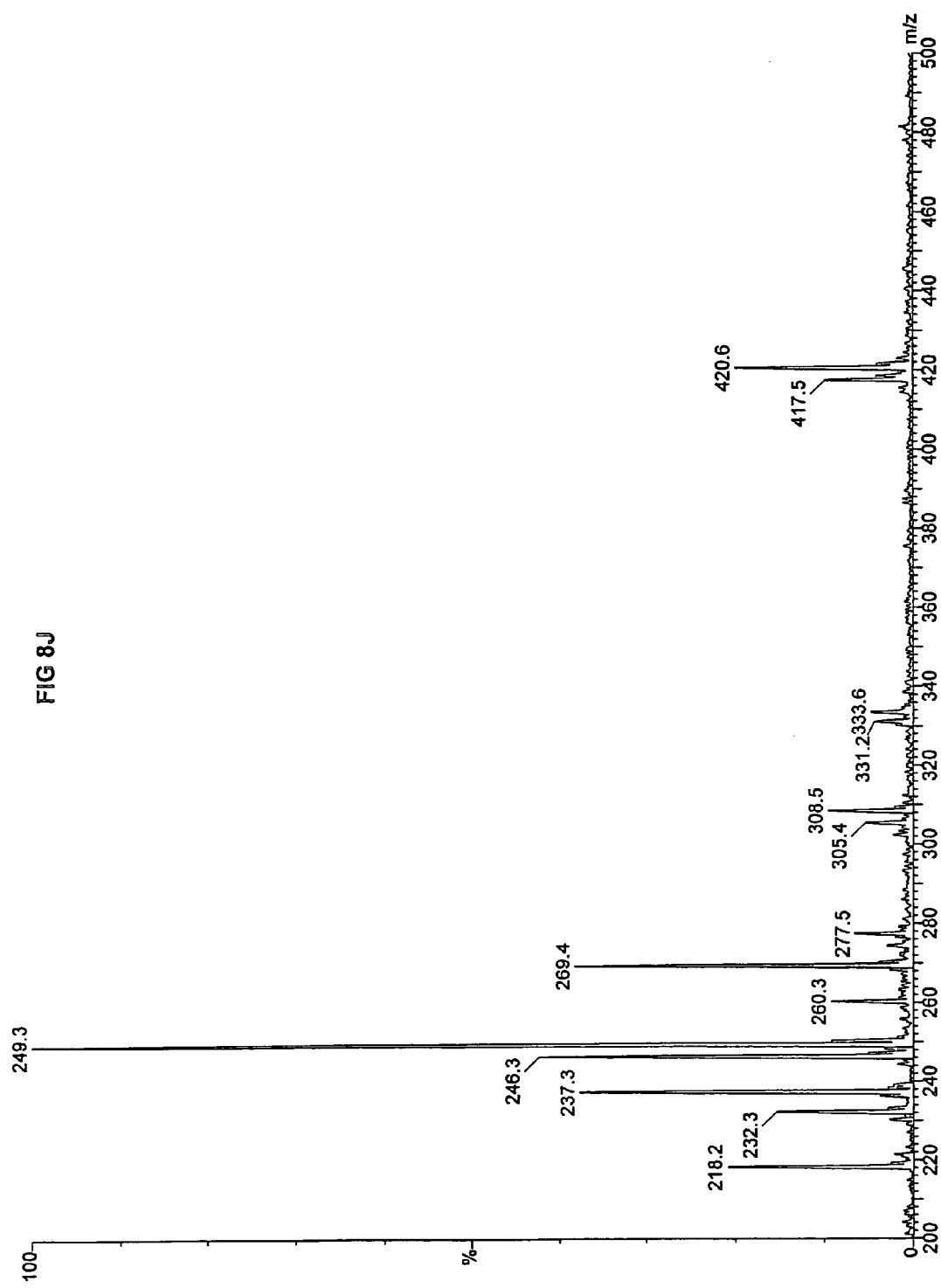
Figure 8K:
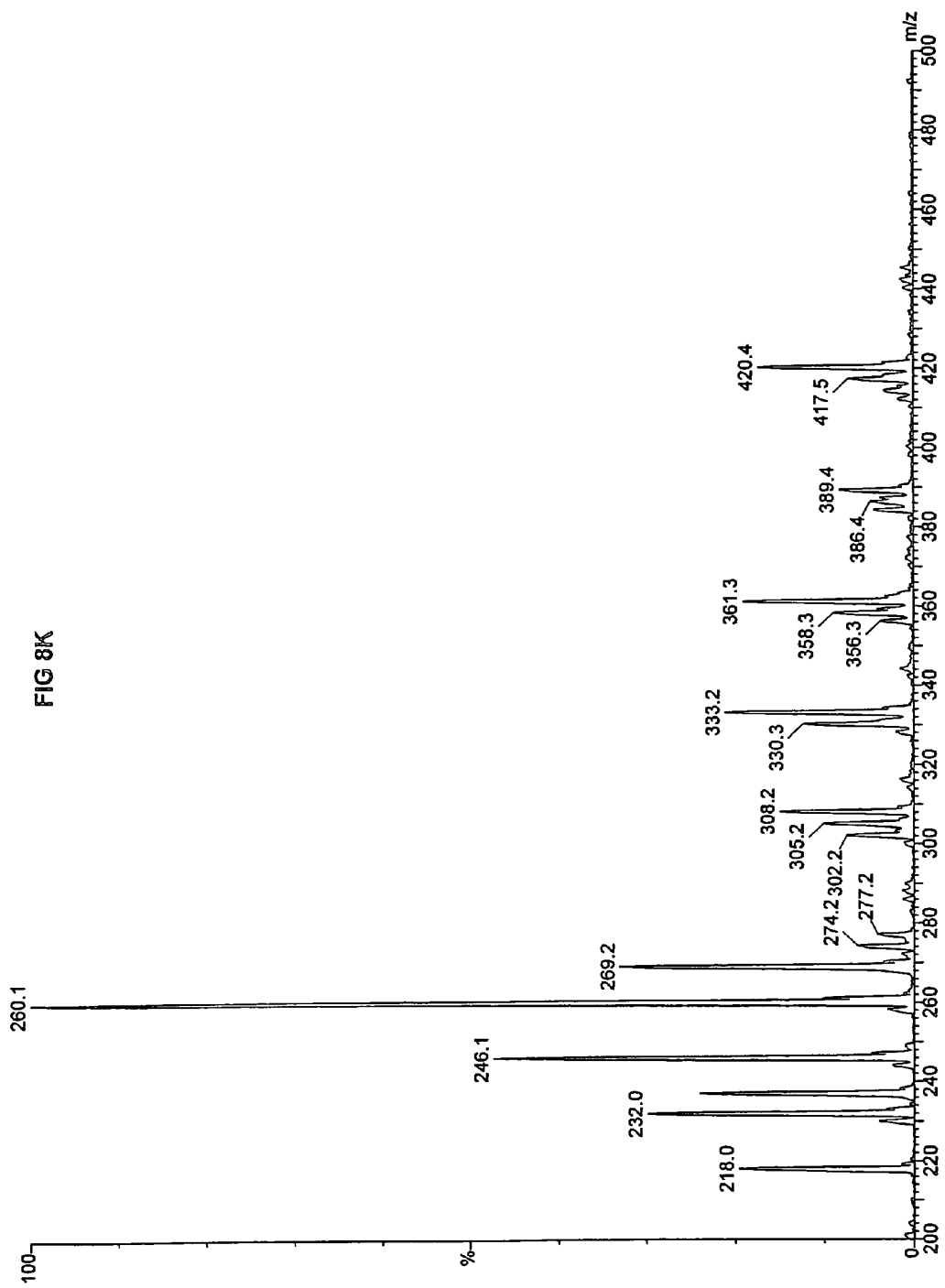
Figure 8L:
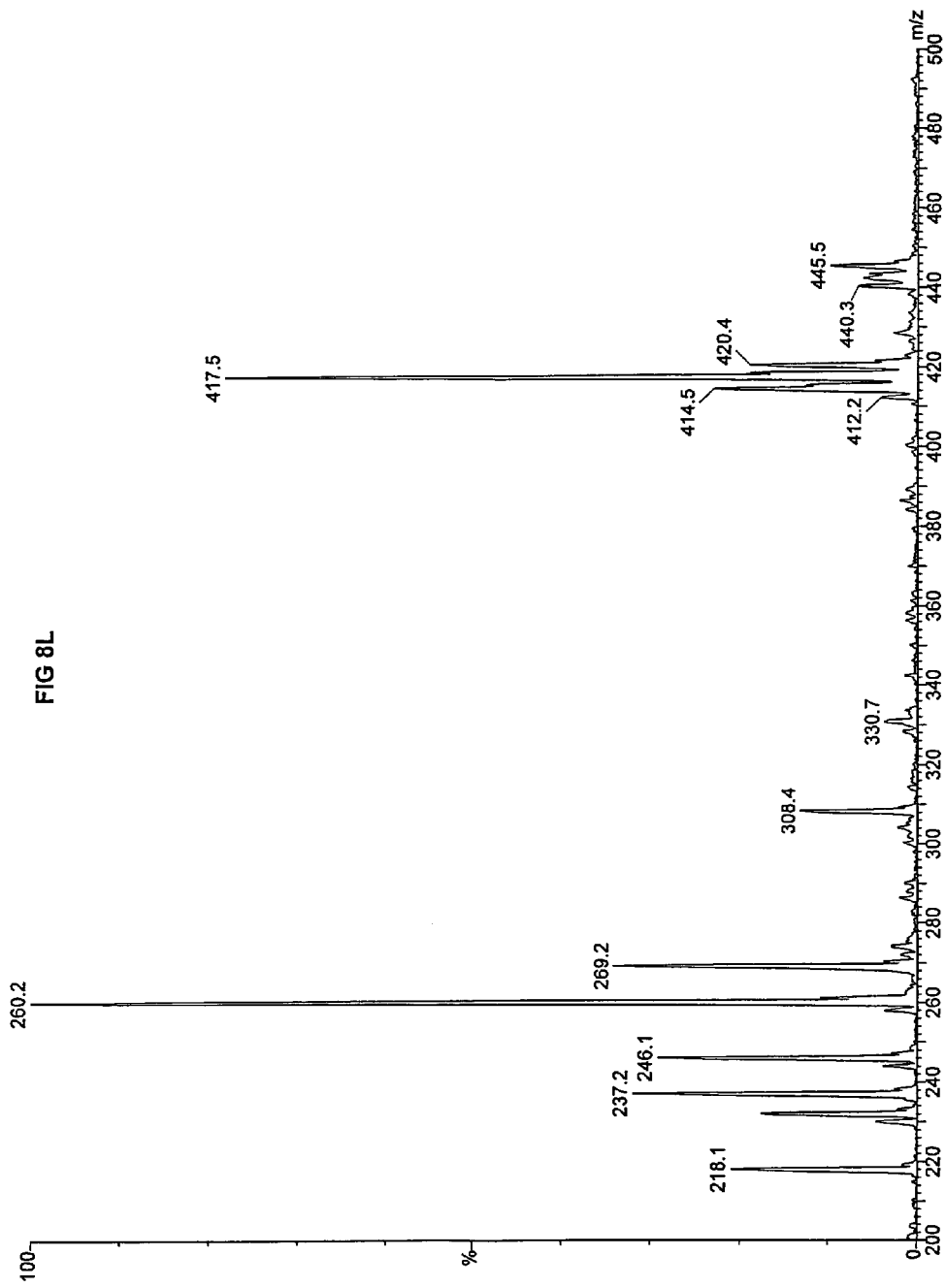

FIG. 8J is a graph depicting a tandem mass spectrometry profile for fibroblasts treated with D3-C16 (16-$^2$H$_3$-palmitate). The fibroblasts were obtained from a child who suffered from short-chain acyl-CoA dehydrogenase (SCAD) deficiency. Test parameters were: parents of 99FB (fast atom bombardment) and MCA acquisition. Internal standards for the profiles in FIGS. 8J-8L are located at m/z420.4 ($^2$H$_6$-palmitate-C16), m/z308 ($^2$H$_6$-octanoate-C8), m/z269.1 ($^2$H$_9$-isovaleric-C5), and m/z237 ($^2$H$_5$-propionate-C3). The peak at m/z417 represents D3-C16 (16-$^2$H$_3$-palmitate).

FIG. 8K is a graph depicting a tandem mass spectrometry profile for fibroblasts treated with D3-C16 (16-H$_3$-palmitate). The fibroblasts were obtained from a child who suffered from electron transfer flavoprotein QO dehydrogenase-mild (ETF-DH mild) deficiency. Test parameters were: parents of 99FB (fast atom bombardment) and MCA acquisition. The peak at m/z417.3 represents D3-C16 (16-$^2$H$_3$-palmitate).

FIG. 8L is a graph depicting a tandem mass spectrometry profile for fibroblasts treated with D3-C16 (16-$^2$H$_3$-palmitate). The fibroblasts were obtained from a child who suffered from electron transfer flavoprotein QO dehydrogenase-severe (ETF-DH severe) deficiency. Test parameters were: parents of 99FB (fast atom bombardment) and MCA acquisition. The peak at m/z417.3 represents D3-C16 (16-$^2$H$_3$-palmitate).

DETAILED DESCRIPTION

It has now been determined that fatty acids having seven carbons (C$_7$) or their triglycerides do not require the usual enzymes needed for transporting long-chain fatty acids into the mitochondrion for energy production, i.e., carnitine/acyl-carnitine translocase, carnitine palmitoyltransferase ("CPT") I and CPT II. Thus, triglycerides composed of seven-carbon fatty acids are useful as a nutritional supplement to overcome fatty acid metabolism deficiencies that require such enzymes. Nutritional supplements or pharmaceutical preparations comprising seven-carbon fatty acids are useful in treatment of inherited metabolic disorders as well as acquired metabolic derangements.

A preferred seven-carbon fatty acid is n-heptanoic acid. n-Heptanoic acid is a saturated straight chain seven-carbon fatty acid with the following structure:

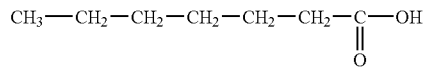

Triheptanoin is a triglyceride made by the esterification of three n-heptanoic acid molecules and glycerol. In regard to therapy, the terms heptanoic acid, heptanoate, and triheptanoin may be used interchangeably in the following description. Also, it will be understood by those skilled in the art that heptanoic acid, heptanoate, and triheptanoin are used throughout the following description as an exemplary seven-carbon fatty acid source of the invention and is intended to be illustrative of the invention, but is not to be construed to limit the scope of the invention in any way. Substituted, unsaturated, or branched heptanoate, as well as other modified seven-carbon fatty acids can be used without departing from the scope of the invention.

Figure 1:
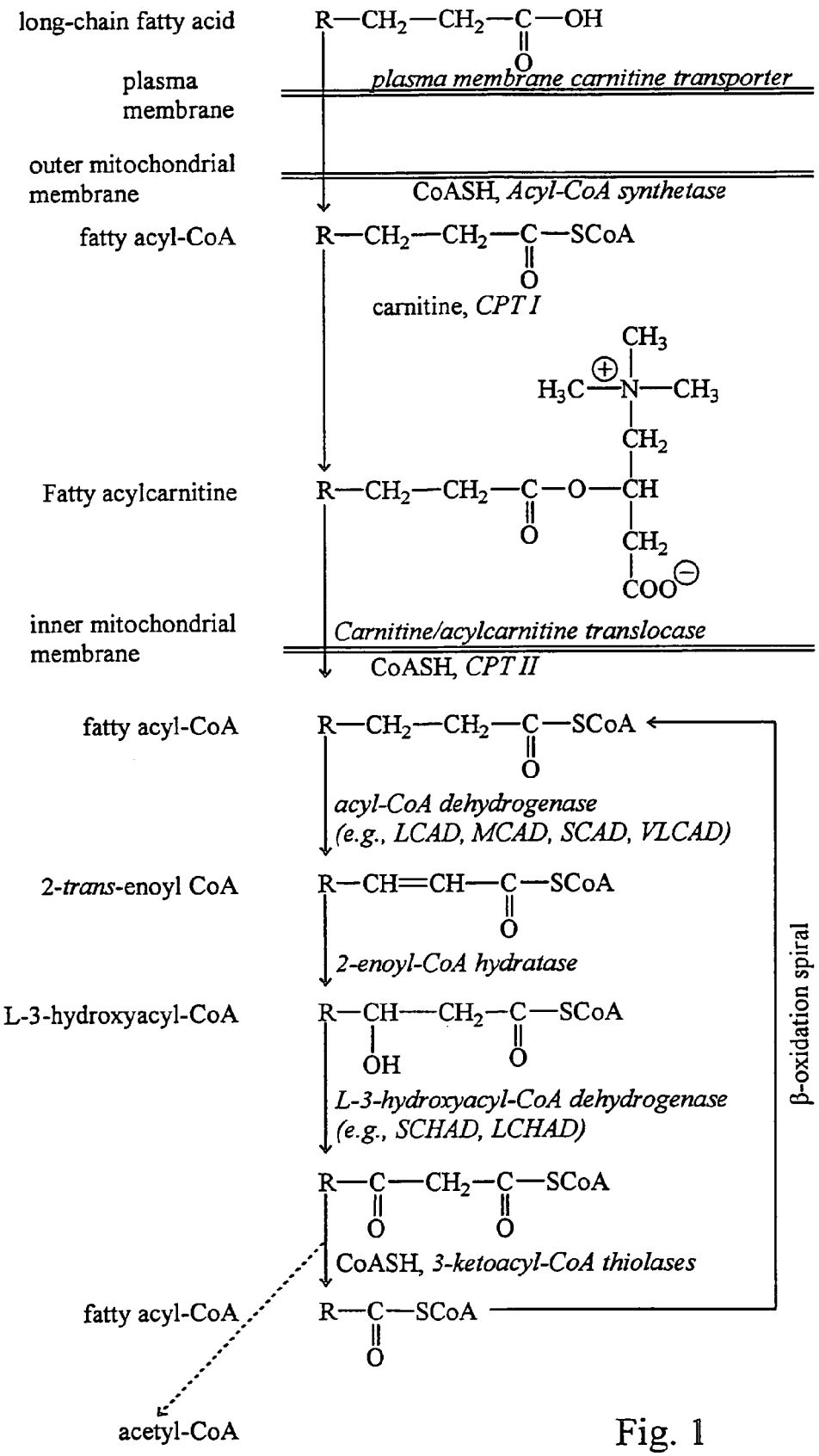
FIG. 1 is a diagram depicting the pathway of mitochondrial β-oxidation for long-chain fatty acids, with the required transporters and enzymes italicized and the three designated membranes represented by double lines.
Figure 2:
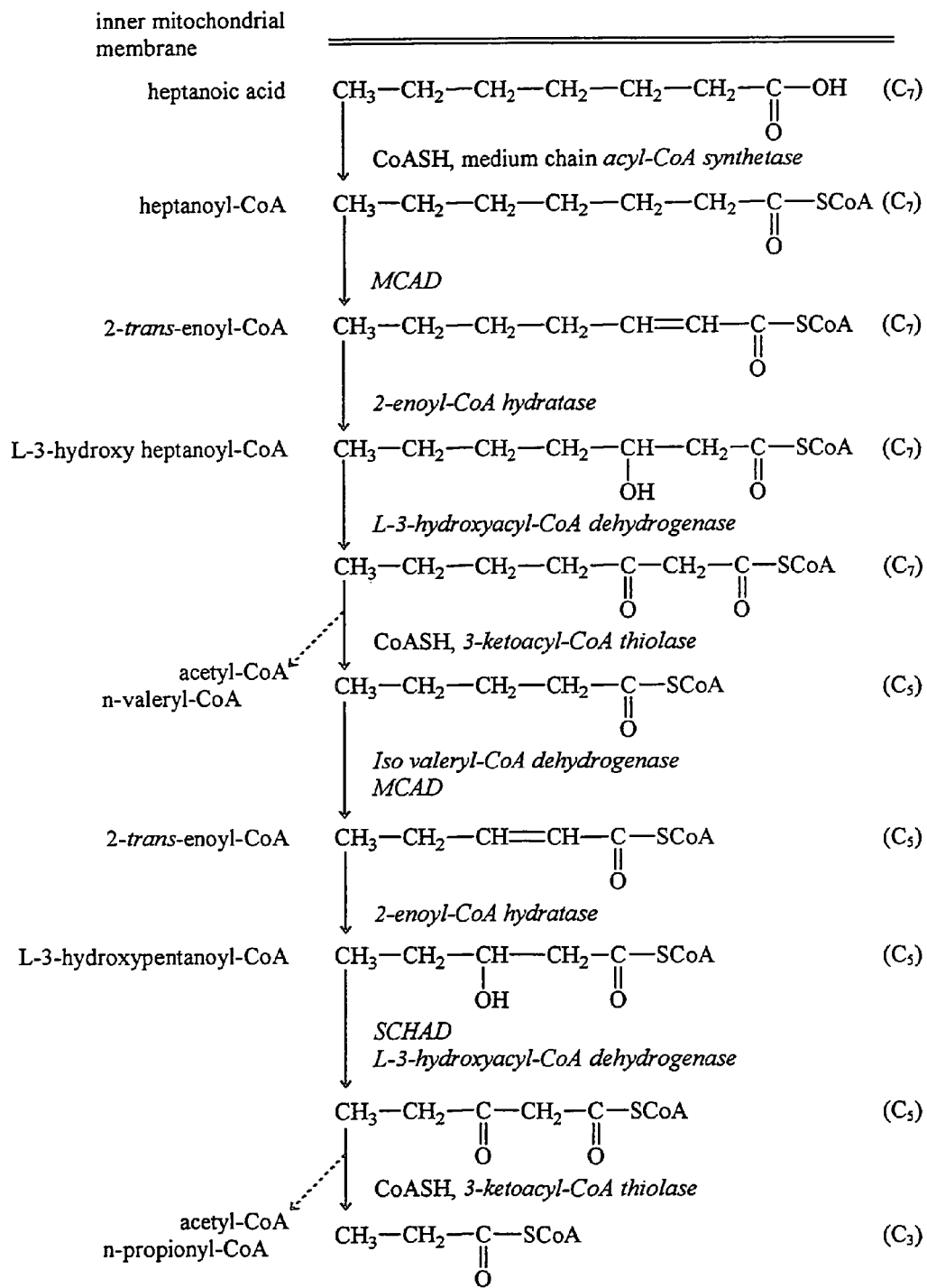
FIG. 2 is a diagram depicting the pathway of mitochondrial β-oxidation for n-heptanoic acid, with the required transporters and enzymes italicized and the designated inner mitochondrial membrane represented by a double line.

Triheptanoin is first broken down into three molecules of heptanoic acid and glycerol. As illustrated in FIG. 2, the heptanoic acid is then broken down through normal β-oxidative procedures to n-valeryl-CoA (C$_5$) and acetyl-CoA (C$_2$) in the first cycle. In the second cycle, the n-valeryl-CoA is then broken down to propionyl-CoA (C$_3$) and acetyl-CoA (C$_2$), both of which are important precursors as fuel for the Kreb's cycle and energy production. Triheptanoin, therefore, is useful as an efficient source of fuel for energy production. Additionally, propionyl-CoA is a direct precursor for glucose production. Consequently, triheptanoin is useful as a dietary supplement for patients susceptible to hypoglycemia, especially for premature infants and the elderly. Triheptanoin can also be utilized as a growth rate stimulant for premature infants, allowing for shorter hospitalizations and thereby reducing medical costs for these infants. Further, since fatty acids are the major fuel for heart tissue and because it has the property of being gluconeogenic, triheptanoin can be used in direct fueling of heart tissue in adults recuperating from cardiac or other high-risk surgery.

Heptanoic acid is found in various fusel oils in appreciable amounts and can be extracted by any means known in the art. It can also be synthesized by oxidation of heptaldehyde with potassium permanganate in dilute sulfuric acid. (Ruhoff, *Org Syn* coll. vol II, 315 (1943)). Heptanoic acid is also commercially available through Sigma Chemical Co. (St. Louis, Mo.).

Triheptanoin can be obtained by the esterification of heptanoic acid and glycerol. by any means known in the art. Triheptanoin is also commercially available through Condea Chemie_GmbH (Witten, Germany), now Sasol (Witten, Germany) as Special Oil 107.

Unsaturated heptanoates can also be utilized as a nutritional supplement to overcome fatty acid metabolism deficiencies. In addition, substituted, unsaturated, and/or branched seven-carbon fatty acids which readily enter the mitochondrion without special transport enzymes can be utilized in the present invention. For example, 4-methylhexanoate, 4-methylhexenoate, and 3-hydroxy-4-methylhexanoate are broken down by normal β-oxidation to 2-methylbutyric acid with final degradation accomplished via the isoleucine pathway. Likewise, 5-methylhexanoate, 5-methylhexenoate, and 3-hydroxy-5-methylhexanoate are broken down by normal β-oxidation to isovaleric acid with final degradation accomplished via the leucine pathway.

The seven-carbon triglycerides of the present invention can be administered orally or parenterally. Preferably, it can be administered via ingestion of a food substance containing a seven-carbon fatty acid source such as triheptanoin at a concentration effective to achieve therapeutic levels. Alternatively, it can be administered as a capsule or entrapped in liposomes, in solution or suspension, alone or in combination with other. nutrients, additional sweetening and/or flavoring agents. Capsules and tablets can be coated with sugar, shellac and other enteric agents as is known.

The method of administration is determined by the age of the patient and degree of fatty acid metabolism deficiency. For the treatment of infants with fatty acid metabolism defects, especially translocase deficiency, triheptanoin is preferably added as a nutritional supplement to a dietary infant formula comprising low fat and/or reduced long-chain fatty acids. Exemplary commercially available infant formulas for use with triheptanoin include Tolerex (Novartis Nutritionals, Minneapolis, Minn.), Vivonex (Ross Laboratories, Columbus, Ohio), and Portagen and Pregestamil (Mead Johnson (Evansville, Ind.). Triheptanoin is added to the formula at a concentration effective for achieving therapeutic results. For children and adult patients requiring a nutritional supplement, e.g., surgery or oncology patients undergoing chemotherapy, triheptanoin is preferably supplied as a nutritional drink or as part of a total parenteral nutrient administration.

For patients suffering from a complete breakdown of the fatty acid metabolic pathway due to an inborn error of metabolism, triheptanoin is utilized at a concentration which provides approximately 15% to 40%, preferably 20% to 35%, and most preferably approximately 25% of the total calories per 24 hours.

For patients in which the fatty acid metabolic pathway is functional at a reduced efficiency (e.g., premature infant, elderly, cardiac patient), triheptanoin is utilized at a concentration which provides approximately 15% to 40%, preferably 20% to 35%, and most preferably approximately 25% of the total calories per 24 hours.

Since propionyl-CoA is a metabolic by-product of triheptanoin oxidation, increased blood levels of propionic acid can result. Moreover, propionyl-CoA can enter into other enzymatic reactions which produce toxic compounds affecting the Kreb's cycle and the urea cycle. Therefore, the administration of a seven-carbon fatty acid such as n-heptanoic acid and/or triheptanoin supplement, especially in patients exhibiting a build-up of serum propionic acid, may require the administration of a carnitine supplement and/or a biotin and vitamin B12 combination. In the presence of excess L-carnitine and the mitochondrial enzyme carnitine acetyltransferase, propionyl-CoA is converted to propionylcarnitine, a non-toxic substance which is excreted in the urine. Biotin is a vitamin cofactor required for the enzyme propionyl-CoA carboxylase which catalyzes the conversion of propionyl-CoA to methylmalonyl-CoA. Cyanocobalamin is a form of vitamin B12 which acts as a cofactor for the enzyme methylmalonyl-CoA mutase which catalyzes the conversion of methylmalonyl-CoA to succinyl-CoA. Succinyl-CoA is readily pulled into the Kreb's cycle. Therefore, excess propionyl-CoA in the patient's blood is removed by conversion to succinyl-CoA.

EXAMPLE 1

Supplementation in Cell Lines

The addition of n-heptanoic acid to cultured cells (fibroblasts) taken from patients with a lethal form of translocase deficiency indicated successful oxidation.

Because a sibling had died at the age of four days from severe translocase deficiency, amniocytes obtained from a fetus were examined for competency in fatty acid metabolism. The tests revealed that the fetus also had severe translocase deficiency.

Figure 3A:
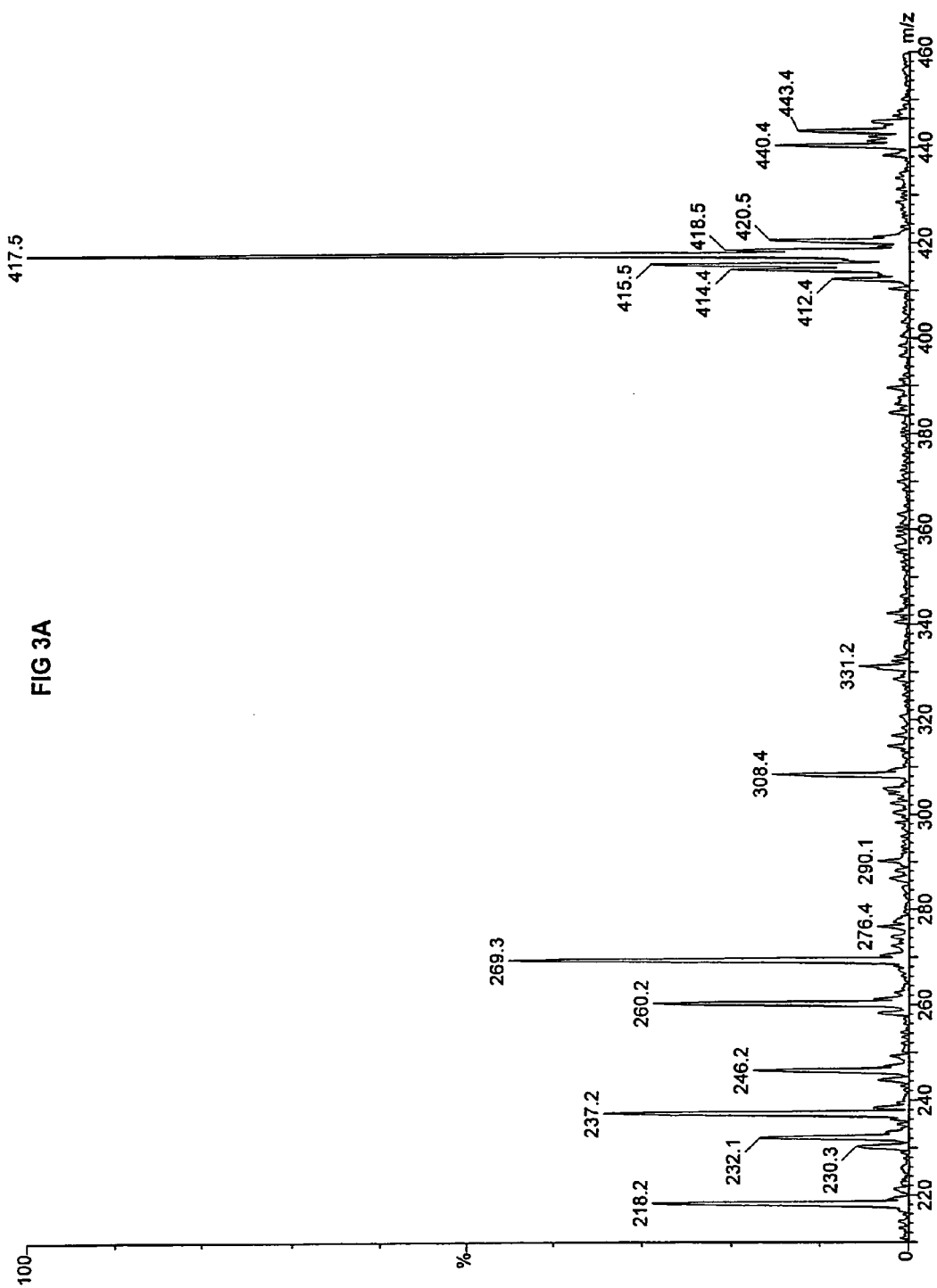
FIG. 3A is a graph depicting a tandem mass spectrometry profile for fibroblasts treated with D3-C16 (16-$^2$H$_3$-palmitate). The fibroblasts were obtained from a deceased child who suffered from severe translocase deficiency. Test parameters were: parents of 99FB (fast atom bombardment) and MCA acquisition.
Figure 3B:
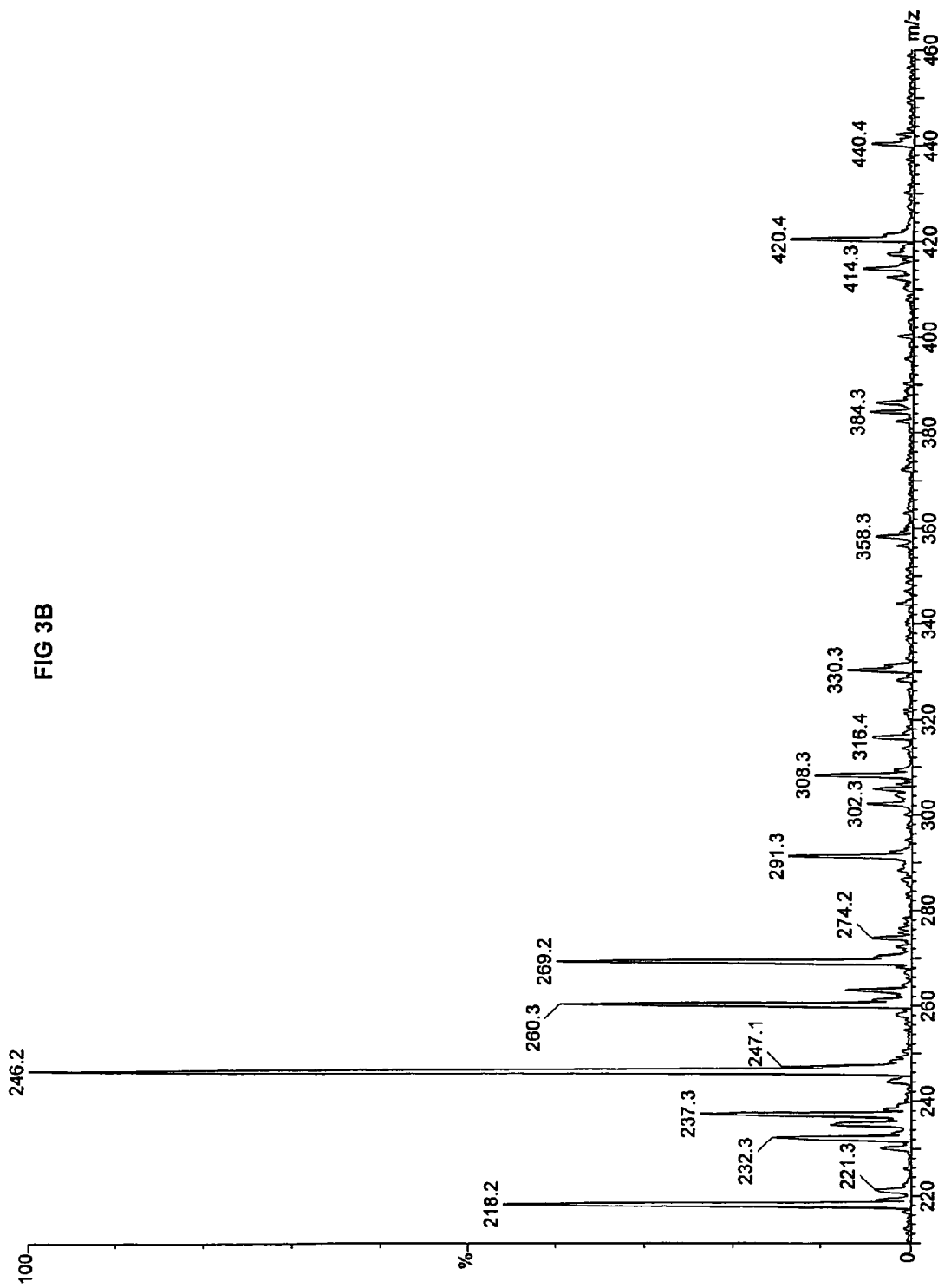
FIG. 3B is a graph depicting a tandem mass spectrometry profile for fibroblasts treated with D3-C7 (7-$^2$H$_3$-heptanoate). The fibroblasts were obtained from the deceased child reported in FIG. 3A who suffered from severe translocase deficiency. Test parameters were: parents of 99FB (fast atom bombardment) and MCA acquisition.
Figure 4A:
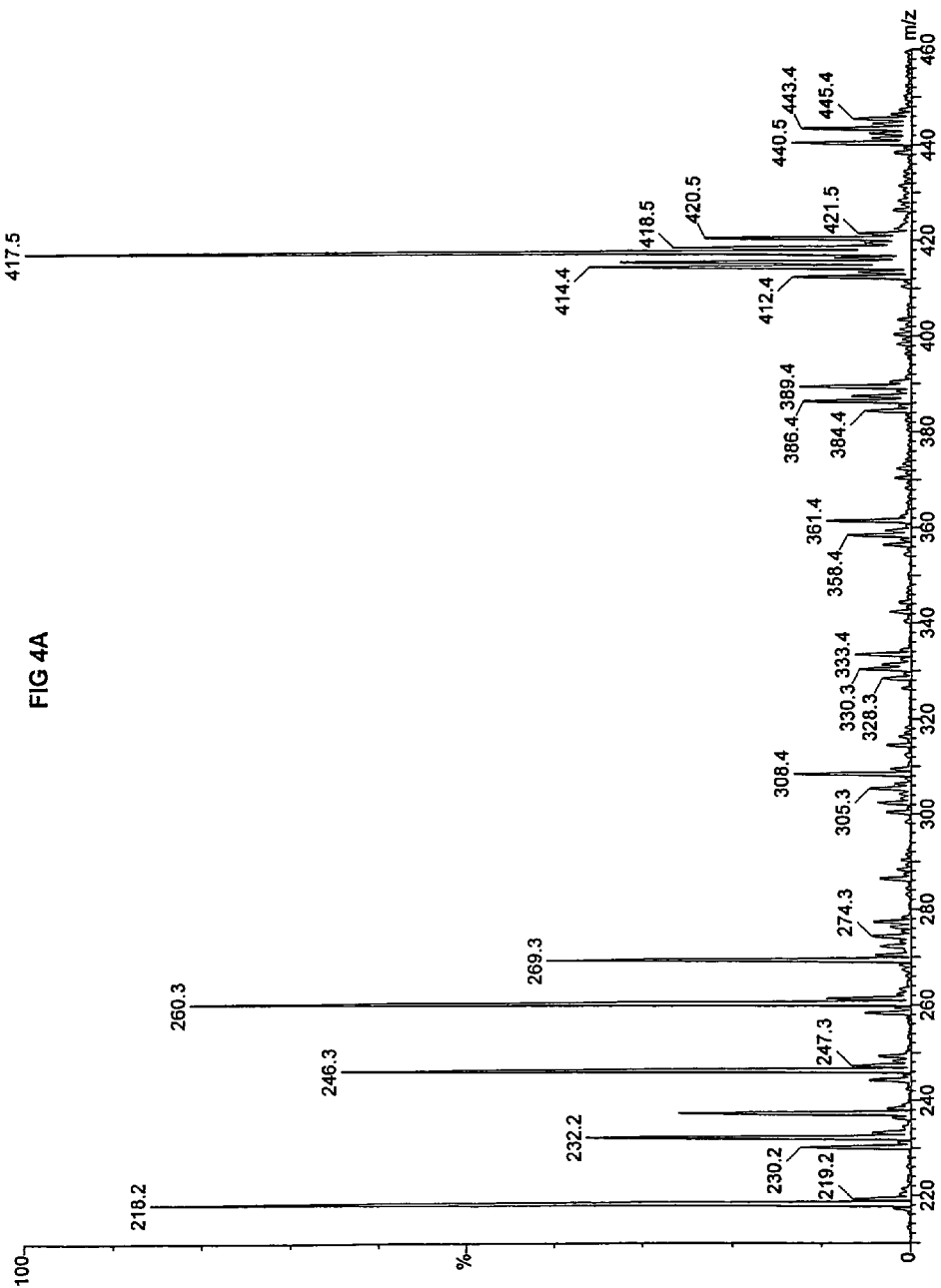
FIG. 4A is a graph depicting a tandem mass spectrometry profile for amniocytes treated with D3-C16 ($^2$H$_3$-palmitate-C16). The amniocytes were obtained from a fetus diagnosed with severe translocase deficiency, whose sibling was the deceased child reported in FIGS. 3A and 3B. Test parameters were: parents of 99FB (fast atom bombardment) and MCA acquisition.
Figure 4B:
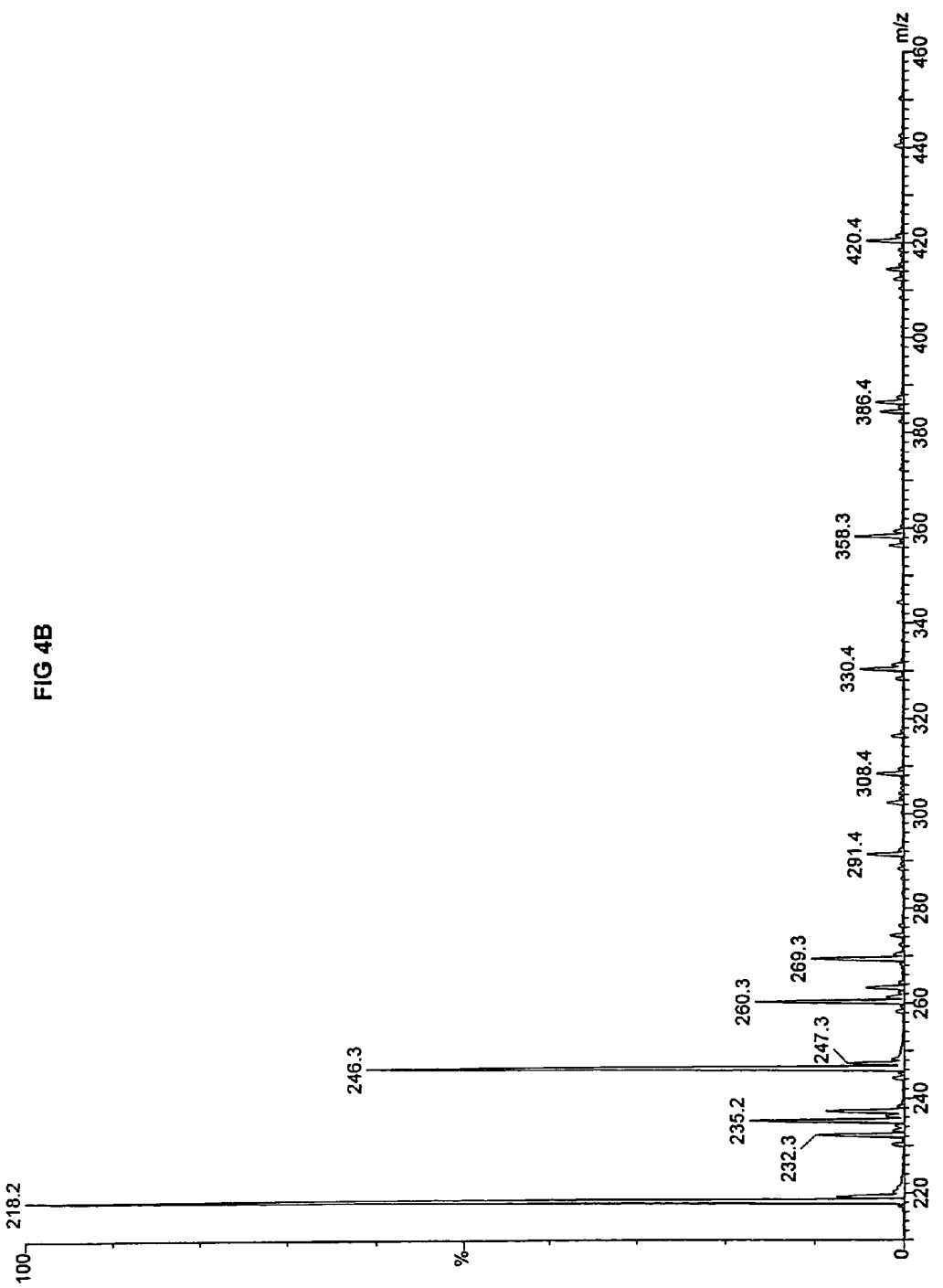
FIG. 4B is a graph depicting a tandem mass spectrometry profile for amniocytes treated with D3-C7 (7-$^2$H$_3$-heptanoate). The amniocytes were obtained from the fetus reported in FIG. 4A who was diagnosed with severe translocase deficiency and whose sibling was the deceased child reported in FIGS. 3A and 3B. Test parameters were: parents of 99FB (fast atom bombardment) and MCA acquisition.

Fibroblasts taken from the deceased sibling and amniocytes taken from the fetus were both evaluated for fatty acid metabolism of n-heptanoic acid ($C_7$) using a tandem mass spectrometry assay previously reported. (Yang, et al. 1998. "Identification of four novel mutations in patients with carnitine palmitoyltransferase II (CPT II) deficiency," *Mol Genet Metab* 64:229-236). The mass spectrometry results are presented for palmitate in FIG. 3A and triheptanoin in FIG. 3B for the fibroblasts taken from the deceased sibling, and for palmitate in FIG. 4A and triheptanoin in FIG. 4B for the amniocytes taken from the fetus. Results of the study showed that n-heptanoic acid (FIGS. 3B and 4B) was independent of carnitine/acylcarnitine translocase and readily oxidized to propionyl-CoA despite the translocase deficiency in both cell lines. Based on the successful metabolism of n-heptanoic acid by the two cell lines having severe translocase deficiency, the tandem mass spectrometry assay was performed on fibroblast cell lines taken from normal patients and from patients affected by the following inherited defects of fat oxidation as proven by direct enzyme assay in other collaborating laboratories: carnitine palmitoyltransferase I (CPT I); severe carnitine/acyl carnitine translocase (TRANSLOCASE); carnitine palmitoyltransferase II (CPT II); the "cardiac" form of very-long-chain acyl-CoA dehydrogenase (VLCAD-C); the "hypoglycemic" form of very-long-chain acyl-CoA dehydrogenase (VLCAD-H); the mitochondrial trifunctional protein (TRIFUNCTIONAL); long-chain L-3-hydroxy-acyl-CoA dehydrogenase (LCHAD); medium-chain acyl-CoA dehydrogenase (MCAD); short-chain acyl-CoA dehydrogenase (SCAD); electron transfer flavoprotein QO dehydrogenase-mild (ETF-DH mild); and electron transfer flavoprotein QO dehydrogenase-severe (ETF-DH severe). Each cell line was incubated separately with 7-$^2H_3$-heptanoate (D3-C7), 8-$^2H_3$-octanoate (D3-C8), 9-$^2H_3$-nonanoate (D3-C9), and 16-$^2H_3$-palmitate (D3-C16). The results are given as tandem mass spectrometry in FIGS. 5A-L for D3-C7; FIGS. 6A-L for D3-C8; FIGS. 7A-L for D3-C9; and FIGS. 8A-L for D3-C16.

The normal cell line and eleven abnormal cell lines were analyzed in groups of three. For quantitative purposes, labeled internal standards were included in each analysis and are designated as "IS" on the first profile in each group. The mass numbers for these standards are: m/z420 ($^2H_6$-palmitate-C16), m/z308 ($^2$H$_6$-octanoate-C8), m/z269 ($^2$H$_9$-isovaleric-C5), and m/z237 ($^2$H$_5$-propionate-C3), wherein m/z is the mass:charge ratio.

As shown in FIG. 8A, when normal cells are incubated with D3-C16, a profile of labeled acylcarnitine intermediates can be observed from C16 down to and including C4. The mass numbers for these $^2$H$_3$-labeled acylcarnitines, as methyl esters, are m/z417 (C16), m/z389 (C14), m/z361 (C12), m/z333 (C10), m/z305 (C8), m/z277 (C6), and m/z249 (C4).

When you observe the various cell lines incubated with 16-$^2$H$_3$-palmitate D3-C16 (FIGS. 8A-L), virtually no oxidation occurs in CPT I cells (FIG. 8B), and a minimal amount of palmitoylcarnitine from D3-C16 (m/z417 (C16)) is observed as expected since palmitate cannot be easily converted to palmitoylcarnitine for transport into the mitochondrion. In both TRANSLOCASE (FIG. 8C) and CPT II (FIG. 8D) deficient cell lines, no oxidation occurs but large quantities of labeled palmitoylcarnitine from D3-C16 (m/z417 (C16)) accumulate as a result of the presence of CPT I. The abnormal profiles of labeled acylcarnitines in VLCAD-C (FIG. 8E), VLCAD-H (FIG. 8F), TRIFUNCTIONAL (FIG. 8G), LCHAD (FIG. 8H), ETF-DH-mild (FIG. 8K), and ETF-DH-severe (FIG. 8L) cell lines reflect accumulations corresponding to the carbon chain length specificity of the missing enzyme activity. In MCAD (FIG. 8I), oxidation clearly proceed down to the level of C8 (m/z305.3), at which point there is a marked accumulation reflecting the substrate specificity of the missing MCAD enzyme. Similarly, in SCAD (FIG. 8J), oxidation stops at m/z249 ($^2$H$_3$-butylcarnitine-C4). These results indicate that CPT I, translocase, CPT II, VLCAD, trifunctional, LCHAD, SCAD, and ETF-DH are all required for complete oxidation of palmitate.

In the case of D3-C8 (FIGS. 6A-L), the relative accumulation of m/z 305 ($^2$H$_3$-octanoate-C8) indicates a distinct requirement for both translocase (FIG. 6C) and MCAD (FIG. 6I) for complete oxidation. While commercial medium chain triglycerides (MCT), the major component being octanoate, are considered independent of CPT I, translocase, and CPT II, this data for $^2$H$_3$-octanoate-C8 indicates that MCT is not an effective treatment for severe translocase deficiency. Further, the data illustrates that MCT would not be appropriate treatment for MCAD deficiency.

For cell lines treated with odd-carbon substrates D3-C7 (FIGS. 5A-L) and D3-C9 (FIGS. 7A-L), the beneficial effect is based on: (1) the absence of the diagnostic profile which could be produced to some extent from oxidation of unlabeled endogenous lipid in the culture medium; and (2) the relative amounts of m/z235 ($^2$H$_3$-propionate-C3) as the labeled end product of odd-carbon degradation compared to that seen in the normal control cells (FIG. 5A for D3-C7 or FIG. 7A for D3-C9). This relative amount of m/z235 ($^2$H$_3$-propionate-C3) is compared to the level of the internal standards at m/z269 ($^2$H$_9$-isovaleric-C5) and m/z237 ($^2$H$_5$-propionate-C3). For D3-C9, an increase was observed at m/z319 (9-$^2$H$_3$-nonanoate) in TRANSLOCASE, CPT II, and LCHAD cell lines. These results indicate that translocase, CPT II, and LCHAD are all required for complete oxidation of nonanoate.

For D3-C7, the relative amounts of $^2$H$_3$-propionate-C3 (m/z235) produced for the normal cells and CPT I, translocase, CPT II, VLCAD, trifunctional, LCHAD, and SCAD abnormal cell lines (FIGS. 5A-H and J) are either comparable to or in excess of the amount seen in normal cells, indicating that beneficial oxidation of the precursor occurred. One observed exception is MCAD deficiency (FIG. 5I), which is expected as D3-C7 requires MCAD for oxidation, and in its absence, m/z291 ($^2$H$_3$-heptanoylcarnitine-C7) is markedly increased. For ETF-DH, no oxidation of labeled 7-$^2$H$_3$-heptanoate was observed. These results indicate that, with the exception of MCAD and ETF dehydrogenase, n-heptanoic acid-supplemented compositions can be used in the treatment of the following fatty acid defects: translocase deficiency; carnitine palmitoyltransferase I and II deficiencies; L-3-hydroxyacyl-CoA dehydrogenase (LCHAD) deficiency; very-long-chain acyl-CoA dehydrogenase (VLCAD) deficiency; and short chain acyl-CoA dehydrogenase (SCAD) deficiency.

EXAMPLE 2

In Vivo Utilization of Triheptanoin Supplementation in Severe Translocase-Deficient Patient Treatment of the infant with severe neonatal translocase deficiency identified in Example 1 using triheptanoin-supplemented low fat formula was successful. Additionally, there is support for the correlation between the clinical response to triheptanoin therapy and the in vitro mass spectrometry analysis of the infant's amniocytes.

At 38 weeks gestation, delivery of the infant whose amniocytes tested positive for severe translocase deficiency as described in Example 1 was accomplished. Cord blood was analyzed for total and free carnitine levels as well as levels of individual acylcarnitines by tandem mass spectrometry. (Yang, et al. 1998. "Identification of four novel mutations in patients with carnitine palmitoyltransferase II (CPT II) deficiency," *Mol Genet Metab* 64:229-236). Maternal blood at the time of delivery was also assayed for these same levels. Results confirmed that the infant suffered from severe translocase deficiency.

Within the first twelve hours after delivery, a low fat formula supplemented with triheptanoin was fed to the infant via a nasogastric tube. Subsequent feedings with the triheptanoin-supplemented formula were given at the same frequency as any full-term infant. Supplements of carnitine, biotin, and cyanocobalamin were not required.

Arterial blood gases (ABG's), electrolytes, serum urea nitrogen (BUN), creatinine, ammonia, glucose, serum creatine phosphokinase (CPK), ALT, AST, hemoglobin (Hgb), and hematocrit (Hct) were monitored according to standard neonatal intensive care procedures. Acylcarnitines were quantified twice daily by tandem mass spectrometry. Quantitative urine organic acid analysis was performed as well to monitor the amount of dicarboxylic acids present in the urine.

The intervention of triheptanoin-supplemented formula was a total success in suppressing the effects of translocase deficiency. During the infant's hospital stay, the various physiological parameters given above were reported within normal ranges. The infant was discharged from the hospital at 7-8 weeks of age exhibiting perfect dietary management with the triheptanoin-supplemented formula. During continued maintenance on the triheptanoin-supplemented formula, the infant has maintained an average weight gain per day of 35 grams per day, compared to the average weight gain of 20-25 grams per day for the average formula-fed infant. At four and a half months of age, the infant continued to thrive on the triheptanoin-supplemented formula, and no carnitine, biotin, or vitamin B12 supplements had been required.

I claim:

1. A method for treating an adult patient in need of treatment for a cardiac disorder, comprising the steps of:
    identifying a patient in need of treatment for a cardiac disorder; and
    administering to said patient an physiologically effective amount of a n-heptanoic fatty acid selected from hexanoate, 4-methylhexanoate, 4-methylhexenoate, 3-hydroxy-4-methylhexanoate; 5-methylhexanoate, 5-methyhexenoate and 3-hydroxy-5-methylhexanoate to provide relief to said patient from said cardiac disorder selected from cardiac muscle weakness or cardiac myopathy.

2. The method of claim 1, wherein said n-heptanoic fatty acid is bound to a triglyceride comprising at least one selected from 4-methylhexanoate, 4-methylhexenoate, 3-hydroxy-4-methylhexanoate; 5-methylhexanoate, 5-methylhexenoate and 3-hydroxy-5-methylhexanoate.

3. The method of claim 2, wherein said triglyceride comprises three heptanoic acid molecules.

4. The method of any of claims 1, 2, or 3 wherein said cardiac disorder is cardiac muscle weakness.

5. The method of claim 4, wherein said fatty acid is adapted for consumption in one or more doses, and said doses comprise about 15 to about 40% of the dietary caloric requirement for said patient for 24 hours.

6. The method of claim 4, wherein said fatty acid is adapted for consumption in one or more doses, and said doses comprise about 20 to about 35% of the dietary caloric requirement for said patient for 24 hours.

7. The method of claim 4, wherein said fatty acid is administered via enteral administration.

8. The method of claim 4, wherein said fatty acid is administered via parenteral administration.

9. The method of any of claims 1, 2, or 3 wherein said cardiac disorder is cardiac myopathy.

10. The method of claim 9, wherein said fatty acid is adapted for consumption in one or more doses, and said doses comprise about 15 to about 40% of the dietary caloric requirement for said patient for 24 hours.

11. The method of claim 9, wherein said fatty acid is adapted for consumption in one or more doses, and said doses comprise about 20 to about 35% of the dietary caloric requirement for said patient for 24 hours.

12. The method of claim 9, wherein said fatty acid is administered via enteral administration.

13. The method of claim 9, wherein said fatty acid is administered via parenteral administration.

14. The method of any of claims 1, 2, or 3 wherein said cardiac disorder comprises a reduced efficiency of a metabolic pathway of heart tissue.

15. The method of claim 14, wherein said fatty acid is adapted for consumption in one or more doses, and said doses comprise about 15 to about 40% of the dietary caloric requirement for said patient for 24 hours.

16. The method of claim 14, wherein said fatty acid is adapted for consumption in one or more doses, and said doses comprise about 20 to about 35% of the dietary caloric requirement for said patient for 24 hours.

17. The method of claim 14, wherein said fatty acid is administered via enteral administration.

18. The method of claim 14, wherein said fatty acid is administered via parenteral administration.

19. The method of any of claims 1, 2, or 3 wherein said fatty acid is adapted for consumption in one or more doses, and said doses comprise about 15 to about 40% of the dietary caloric requirement for said patient for 24 hours.

20. The method of any of claims 1, 2, or 3 wherein said fatty acid is adapted for consumption in one or more doses, and said doses comprise about 20 to about 35% of the dietary caloric requirement for said patient for 24 hours.

21. The method of any of claims 1, 2, or 3 wherein said fatty acid is administered via enteral administration.

22. The method of any of claims 1, 2, or 3 wherein said fatty acid is administered via parenteral administration.

* * * * *